(12) United States Patent
Edelman

(10) Patent No.: US 11,242,522 B2
(45) Date of Patent: Feb. 8, 2022

(54) REAGENTS, KITS AND METHODS FOR MOLECULAR BARCODING

(71) Applicant: CS GENETICS LIMITED, Cambridge (GB)

(72) Inventor: Lucas Brandon Edelman, Cambridge (GB)

(73) Assignee: CS Genetics Limited, Cambridge (GB)

( * ) Notice: Subject to any disclaimer, the term of this patent is extended or adjusted under 35 U.S.C. 154(b) by 11 days.

(21) Appl. No.: 16/937,225

(22) Filed: Jul. 23, 2020

(65) Prior Publication Data

US 2020/0347382 A1    Nov. 5, 2020

Related U.S. Application Data

(60) Continuation of application No. 16/246,195, filed on Jan. 11, 2019, now Pat. No. 10,731,150, which is a
(Continued)

(30) Foreign Application Priority Data

Jun. 23, 2015 (GB) ..................................... 1511050

(51) Int. Cl.
| | |
|---|---|
| *C12N 15/10* | (2006.01) |
| *C12Q 1/6806* | (2018.01) |
| *C12Q 1/6869* | (2018.01) |

(52) U.S. Cl.
CPC ..... *C12N 15/1065* (2013.01); *C12N 15/1093* (2013.01); *C12Q 1/6806* (2013.01); *C12Q 1/6869* (2013.01)

(58) Field of Classification Search
CPC ............ C12N 15/1065; C12N 15/1093; C12Q 1/6869; C12Q 1/6806; C12Q 2535/122;
(Continued)

(56) References Cited

U.S. PATENT DOCUMENTS

| | | |
|---|---|---|
| 2002/0064779 A1 | 5/2002 | Landegren et al. |
| 2006/0094019 A1 | 5/2006 | Selvin et al. |

(Continued)

FOREIGN PATENT DOCUMENTS

| | | |
|---|---|---|
| WO | WO 2007001986 | 1/2007 |
| WO | WO 2011094669 | 8/2011 |

(Continued)

OTHER PUBLICATIONS

Office Action dated Nov. 30, 2020, Appl. No. CN 201680049082.6, 14 pp.
European Search Report dated Jul. 16, 2020, Appl. No. EP20162828.6, 8 pp.
Examination Report dated Jun. 19, 2020, Appl. No. AU2016281758, 3 pp.

(Continued)

*Primary Examiner* — Robert H Havlin
(74) *Attorney, Agent, or Firm* — Brian E. Davy; Bozicevic, Field & Francis LLP

(57) ABSTRACT

Multimeric barcoding reagents for labelling a target nucleic acid comprise: first and second barcode molecules linked together, wherein each of the barcode molecules comprises a nucleic acid sequence comprising a barcode region; and first and second barcoded oligonucleotides. The multimeric barcoding reagents enable spatial sequencing. A single multimeric barcoding reagent can be used to label sub-sequences of an intact nucleic acid molecule or co-localised fragments of a nucleic acid molecule. The labelled sub-sequences can be sequenced and the sequencing data processed to determine the sequence of sub-sequences from a single intact nucleic acid molecule or from co-localised fragments of a nucleic acid molecule. Corresponding libraries, kits, methods and uses are provided.

7 Claims, 21 Drawing Sheets

Specification includes a Sequence Listing.

Related U.S. Application Data division of application No. 15/738,104, filed as application No. PCT/GB2016/051883 on Jun. 23, 2016, now abandoned.

(58) Field of Classification Search
CPC ........ C12Q 2563/179; C12Q 2565/102; C12Q 2600/16; C40B 40/06
See application file for complete search history.

(56) References Cited

U.S. PATENT DOCUMENTS

| | | |
|---|---|---|
| 2013/0005585 A1 | 1/2013 | Anderson et al. |
| 2013/0130919 A1 | 5/2013 | Chen et al. |
| 2015/0005200 A1 | 1/2015 | Hindson et al. |
| 2015/0284712 A1 | 10/2015 | Kurihara et al. |
| 2016/0244811 A1 | 8/2016 | Edwards |

FOREIGN PATENT DOCUMENTS

| | | |
|---|---|---|
| WO | WO 2012160083 | 11/2012 |
| WO | WO 2013165748 | 11/2013 |
| WO | WO 2014018080 | 1/2014 |
| WO | WO 2014071361 | 5/2014 |
| WO | 2014145820 | 9/2014 |
| WO | WO 2015053943 | 4/2015 |

OTHER PUBLICATIONS

Beaudet et al. (2001) "Homogeneous Assays for Single-Nucleotide Polymorphism Typing Using AlphaScreen," Genome Research, 11:600-608.
Communication under Rule 71(3) dated Jun. 11, 2019, Appl. No. EP16733175.0, 6 pp.
Examination Report dated Jun. 7, 2016, Appl. No. GB1511050.5, 3 pp.
Examination Report dated Sep. 30, 2016, Appl. No. GB1511050.5, 3 pp.
Examination Report dated Apr. 26, 2018, Appl. No. EP16733175.0, 5 pp.
Examination Report dated Dec. 7, 2018, Appl. No. EP16733175.0, 4 pp.
Examination Report dated Feb. 6, 2019, Appl. No. EP16733175.0, 4 pp.
International Preliminary Report on Patentability for Application PCT/GB2016/051883 dated Jan. 4, 2018.
International Search Report and Written Opinion of the International Searching Authority dated Sep. 13, 2016, Int'l. Appl. No. PCT/GB2016/051883, 8 pp.
Search and Examination Report dated Oct. 1, 2015, Appl. No. GB 1511050.5, 10 pp.
Stern et al. (2010) "Self-targeting by CRISPR: gene regulation or autoimmunity?," Trends Genet. 6(8):335-340.
Written Opinion dated Nov. 30, 2018, Appl. No. SG11201710250R, 7 pp.

FIGURE 19

| | Annealed to Genomic DNA Overnight | Annealed to Genomic DNA Overnight, Barcoding Reagents Denatured First | Annealed to Genomic DNA for 3 Hours | Annealed to Genomic DNA for 3 Hours; Barcoding Reagents Denatured First |
|---|---|---|---|---|
| HLA-A_Exon2 | 153 | 62 | 103 | 50 |
| HLA-A_Exon3 | 2548 | 341 | 818 | 106 |
| HLA-A_Exon4 | 489 | 235 | 400 | 108 |
| DQB1_Exon2 | 557 | 627 | 285 | 635 |
| DQB1_Exon3 | 2186 | 1614 | 1085 | 221 |
| BRCA1_US1 | 1771 | 941 | 1047 | 544 |
| BRCA1_SNP7 | 2524 | 1261 | 90 | 43 |
| BRCA1_SNP6 | 731 | 537 | 245 | 339 |
| BRCA1_SNP1 | 10033 | 5787 | 2905 | 1813 |
| BRCA1_DS1 | 4 | 103 | 5 | 0 |
| BRCA_AMP6 | 81 | 69 | 37 | 24 |
| BRCA_AMP7 | 731 | 391 | 40 | 472 |
| On-Target Fraction: | 81 % | 76 % | 82 % | 70 % |

Schematic of Sequence Read from Barcoding of genomic DNA loci
(In 5' to 3' Direction)

REAGENTS, KITS AND METHODS FOR MOLECULAR BARCODING

TECHNICAL FIELD

The present invention relates to molecular barcoding. Provided are multimeric barcoding reagents, libraries of molecular barcoding reagents and kits comprising multimeric barcoding reagents. There are also provided methods relating to the multimeric barcoding reagents and uses of the multimeric barcoding reagents.

BACKGROUND

'Molecular barcoding' was developed to address problems generated by raw error rates intrinsic to DNA sequence machines (synthetic accuracy), and also problems related to counting individual nucleic acid molecules within a sample (molecular counting).

Molecular barcoding generally involves attaching (for example, by ligation or by primer-extension) a unique nucleic acid label (a 'barcode') to several single target molecules (DNA or RNA) in a solution containing a large number of such molecules. These labelled molecules are then sequenced, which for each reveals both the sequence of the molecular barcode, and at least part of the sequence of the labelled target molecule itself.

This barcoding is typically used towards two different ends. First, it can be used to enable 'redundant sequencing'. For example, imagine a nucleic acid sample containing 1000 copies of a particular gene in a DNA sample; 999 of the copies hold sequences identical to each other, but a single copy has a particular single-nucleotide mutation. Without barcoding, the sequencer will be unable to detect this mutated copy, since the sequencer makes random errors at a higher rate than 1:1000—i.e. the mutation is so rare in the population of sequenced molecules that it falls below the sequencer's intrinsic background noise threshold.

However, if the 1000 copies have each been labelled with a unique molecular barcode, and each individual labelled molecule is sequenced several times by the sequencing machine (redundant sequencing), you would observe that every time (or, at least 99% of the time, equivalent to the raw accuracy of the sequencer) that the labelled mutated molecule was redundantly sequenced (i.e, every time the target gene sequence was observed to be labelled with that one particular unique barcode that was attached to the mutated starting molecule), that the same apparent mutation would in fact be observed. By contrast, that particular mutation would only be observed approximately 1% of the time (the raw error rate of the sequencer) when the labelled but non-mutated gene copies were redundantly sequenced, as per their respective alternative barcodes.

The barcode thus serves to identify individual input molecules across all their respective multiple copies within the sequencing reaction, allowing a sequence-detection algorithm to specifically focus on their respective reads within a sequencing dataset, and thus avoiding the large amount of stochastic sequence noise (in the form of sequence errors) that is present across the remainder of the dataset. This thus enables 'synthetic accuracy', through redundant sequencing, which is potentially much higher than the raw accuracy of the sequencer itself.

Barcoding can also be used to enable digital 'molecular counting' of input DNA or RNA molecules. In this process, a large number of unique barcodes are attached to input molecules, for example, cDNA copies that have been made from a particular mRNA species. Each input cDNA molecule is labelled (for example, by primer extension) with a single, unique barcode. The molecules are then sequenced, which, as with redundant sequencing, reveals the unique barcode and at least part of each associated labelled input molecule; these molecules are then also each sequenced more than once.

Instead of using this redundant sequencing to reduce sequencing errors, in molecular counting it is used to digitally quantify how many individual molecules of the given target molecule (cDNA in this case) were present in the original sample, by simply counting the total number of unique barcodes that were sequenced and found to be associated with the particular target. Barcode-directed redundant sequencing in this way reduces the chance that any input molecule is stochastically left unsequenced by the sequencing reaction (since each labelled molecule on average is sequenced several times), whilst retaining an accurate measure of input quantity (since redundantly sequenced starting molecules are only counted once, as discriminated by repeated copies of their unique barcode).

Examples of the use of molecular barcodes are provided in U.S. Pat. Nos. 8,728,766, 8,685,678, 8,722,368, Kinde et al., 2011 (PNAS, 108, 23, 9530-9535) and US 20140227705 A1.

A 'synthetic long read' is generated when a long, contiguous sequence of DNA (longer than the readlength attainable on a DNA sequencer) is converted into two or more shorter 'sub-sequences' that are short enough to be read by a DNA sequencer, and which are somehow labelled such that it can be deduced (after sequencing) that the sub-sequences were generated from the same original long DNA sequence. For example, if you want to sequence a particular human gene which is 1000 nucleotides long, but do so with a short-read DNA sequencer with a readlength of 100 nucleotides, you could separate the long sequence into 10 different sub-sequences of 100 nucleotide length, then label each of these 10 sub-sequences with a synthetic, informative 'label' DNA sequence that identifies each of the 10 sub-sequences as coming from the same original 1000 nucleotide DNA molecule, then perform high-throughput DNA sequencing with these 10 resulting DNA molecules, and thus (for each of the 10 resulting DNA molecules) attain both the 100 nucleotide sub-sequence, and the associated identifying DNA label. With this high-throughput DNA data an algorithm can be used which detects these identifying labels and uses them to associate the 10 different 100-nucleotide sub-sequences with each other as a collective sub-sequence 'grouping', and therewith estimate that the 10 sub-sequences came from a longer, 1000-nucleotide gene, and therewith estimate the total 1000-nucleotide long genetic sequence by 'stitching' the 10 sub-sequences together in silico into a single 1000-nucleotide long gene.

Two main synthetic long read technologies which have been described in the literature: a partitioning-based approach which is described in US 20130079231 A1; and a barcode-copying approach which is described in Casbon et al., 2013 (Nucleic Acids Research, 2013, 41, 10, e112), U.S. Pat. Nos. 8,679,756 and 8,563,274.

'Spatial sequencing' is considered to be the sequencing of nucleic acids with the inclusion of some information about where each sequenced nucleic acid is located within a particular space (for example, within a particular sample, or within a particular cell). However, very few spatial sequencing methods are known. The main known technology is the fluorescent in situ RNA sequencing (FISSEQ) technique. In FISSEQ a sample of cells are cross-linked, and while the cells are still intact, RNA is reverse transcribed into cDNA, and amplified whilst still in the crosslinked cells. Then, each amplified cDNA molecule is sequenced optically whilst still in the cells, with a high-powered and sensitive optical detection system. This method is described in Lee et al., 2014 (Science, 343, 6177, 1360-1363).

The invention addresses two main types of problem in the sequencing field: 1) specific analytic limitations of DNA sequencing machines; and 2) biophysical challenges associated with common types of experimental DNA samples.

Current high-throughput DNA-sequencing machines are powerful platforms used to analyse large amounts of genetic material (from thousands to billions of DNA molecules) and function as systems for both basic research and applied medical applications. However, all current DNA sequencing machines are subject to certain analytic limitations which constrain the scientific and medical applications in which they can be effectively used. The chief such limitations include finite raw readlengths and finite raw accuracy, both of which are described below.

With regard to finite raw readlengths, each DNA sequencing platform is characterised by a typical 'readlength' that it can attain, which is the 'length' in nucleotides of DNA that it can 'read' of each sequenced molecule. For most sequencing machines, this ranges from 100 to ~500 nucleotides.

With regard to finite raw accuracy, each sequencing platform is also characterised by an attainable 'raw accuracy', typically defined as the likelihood that each given nucleotide it sequences has been determined correctly. Typical raw accuracy for the most popular sequencing platforms range between 98 and 99.5%. The related quantity, the 'raw error' rate, is essentially the converse of raw accuracy, and is the per-nucleotide likelihood that the sequencer randomly reports an incorrect nucleotide in a particular sequenced DNA molecule.

In addition, certain common experimental DNA samples pose biophysical challenges for sequencing. These challenges arise from the unique (and troublesome) molecular state of DNA in these samples, which makes it difficult to sequence them or to extract important pieces of genetic information therefrom, irrespective of the sequencing machine employed. For example, Formalin-Fixed Paraffin-Embedded (FFPE) samples are the standard experimental tool for performing molecular pathology from human biopsy specimens. However, the process of creating an FFPE sample—in which the biopsy specimen is fixed (crosslinked and kept physically together and stable at the molecular level) by a harsh chemical, and then embedded in a wax—creates significant damage to the DNA and RNA contained therein. DNA and RNA from FFPE samples is thus heavily fragmented (generally into small fragments between 50 and 200 nucleotides), and also includes sporadic damage to individual nucleotides which makes it essentially impossible to amplify or isolate long, contiguous sequences.

DESCRIPTION

The invention provides multimeric barcoding reagents, libraries of molecular barcoding reagents and kits comprising multimeric barcoding reagents. The invention further provides methods of synthesising a library of nucleic acid barcode molecules from two or more libraries of sub-barcode molecules. The invention further provides methods of assembling a multimeric barcode molecule from two or more barcode molecules and methods of assembling a library of multimeric barcode molecules from two or more libraries of barcode molecules. The invention further provides methods of synthesising a multimeric barcoding reagent and libraries of multimeric barcoding reagents. The multimeric barcoding reagent(s) may be synthesised from the multimeric barcode molecules. The invention further provides methods of preparing a nucleic acid sample for sequencing using one or more multimeric barcoding reagents, methods of sequencing a sample and methods of processing sequencing data. The invention further provides methods of generating a synthetic long read. The invention further provides methods of sequencing two or more co-localised target nucleic acids. The invention further provides methods of sequencing target nucleic acids from an individual cell. The invention further provides uses of the multimeric barcoding reagents, libraries and/or kits. The invention further provides methods for profiling a multimeric barcoding reagent or a library of multimeric barcoding reagents.

Multimeric Barcoding Reagents

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises, optionally in the 5' to 3' direction, a barcode region annealed to the barcode region of the first barcode molecule and a target region capable of annealing or ligating to a first sub-sequence of the target nucleic acid, and wherein the second barcoded oligonucleotide comprises, optionally in the 5' to 3' direction, a barcode region annealed to the barcode region of the second barcode molecule and a target region capable of annealing or ligating to a second sub-sequence of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises a barcode region annealed to the barcode region of the first barcode molecule and a target region capable of ligating to a first sub-sequence of the target nucleic acid, and wherein the second barcoded oligonucleotide comprises a barcode region annealed to the barcode region of the second barcode molecule and a target region capable of ligating to a second sub-sequence of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises in the 5' to 3' direction a barcode region annealed to the barcode region of the first barcode molecule and a target region capable of annealing to a first sub-sequence of the target nucleic acid, and wherein the second barcoded oligonucleotide comprises in the 5' to 3' direction a barcode region annealed to the barcode region of the second barcode molecule and a target region capable of annealing to a second sub-sequence of the target nucleic acid.

Preferably, the barcode molecules comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcode molecules may comprise one or more degenerate nucleotides or sequences. The barcode molecules may not comprise any degenerate nucleotides or sequences.

Preferably the barcoded oligonucleotides comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcoded oligonucleotides may comprise one or more degenerate nucleotides or sequences. The barcoded oligonucleotides may not comprise any degenerate nucleotides or sequences.

The barcode regions may uniquely identify each of the barcode molecules. Each barcode region may comprise a sequence that identifies the multimeric barcoding reagent. For example, this sequence may be a constant region shared by all barcode regions of a single multimeric barcoding reagent. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

Preferably, the barcode region of the first barcoded oligonucleotide comprises a sequence that is complementary and annealed to the barcode region of the first barcode molecule and the barcode region of the second barcoded oligonucleotide comprises a sequence that is complementary and annealed to the barcode region of the second barcode molecule. The complementary sequence of each barcoded oligonucleotide may be at least 5, at least 10, at least 15, at least 20, at least 25, at least 50 or at least 100 contiguous nucleotides.

The target regions may comprise different sequences. Each target region may comprise a sequence capable of annealing to only a single sub-sequence of a target nucleic acid within a sample of nucleic acids. Each target region may comprise one or more random, or one or more degenerate, sequences to enable the target region to anneal to more than one sub-sequence of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The target regions of the barcoded oligonucleotides (which are not annealed to the multimeric barcode molecule(s)) may be non-complementary to the multimeric barcode molecule(s).

The barcoded oligonucleotides may comprise a linker region between the adapter region and the target region. The linker region may comprise one or more contiguous nucleotides that are not annealed to the multimeric barcode molecule and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

The barcode molecules of a multimeric barcode molecule may be linked on a nucleic acid molecule. The barcode molecules of a multimeric barcode molecule may be comprised within a (single) nucleic acid molecule. A multimeric barcode molecule may be a single-stranded nucleic acid molecule (e.g. single-stranded DNA) comprising two or more barcode molecules. Such a single-stranded nucleic acid molecule provides the backbone to which single-stranded barcoded oligonucleotides may be annealed.

The barcode molecules may be linked by attachment to a solid support (e.g. a bead). For example, barcode molecules of known sequence may be linked to beads. A solution of soluble beads (e.g. superparamagnetic beads or styrofoam beads) may be functionalised to enable attachment of two or more barcode molecules. This functionalisation may be enabled through chemical moieties (e.g. carboxylated groups), and/or protein-based adapters (e.g. streptavidin) on the beads. The functionalised beads may be brought into contact with a solution of barcode molecules under conditions which promote the attachment of two or more barcode molecules to each bead in the solution. Optionally, the barcode molecules are attached through a covalent linkage, or through a (stable) non-covalent linkage such as a streptavidin-biotin bond, or a (stable) oligonucleotide hybridisation bond.

The multimeric barcoding reagent may be configured such that: each of the barcode molecules comprises a nucleic acid sequence comprising in the 5' to 3' direction an adapter region and a barcode region; the first barcoded oligonucleotide comprises, optionally in the 5' to 3' direction, a barcode region annealed to the barcode region of the first barcode molecule, an adapter region annealed to the adapter region of the first barcode molecule and a target region capable of annealing to a first sub-sequence of the target nucleic acid; and the second barcoded oligonucleotide comprises, optionally in the 5' to 3' direction, a barcode region annealed to the barcode region of the second barcode molecule, an adapter region annealed to the adapter region of the second barcode molecule and a target region capable of annealing to a second sub-sequence of the target nucleic acid.

The adapter region of each barcode molecule may comprise a constant region. Optionally, all adapter regions of a multimeric barcoding reagent are substantially identical. The adapter region may comprise at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The multimeric barcoding reagent may comprise: at least 5, at least 10, at least 20, at least 25, at least 50, at least 75, at least 100, at least 200, at least 500, at least 1000, at least 5000, or at least 10,000 barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 unique or different barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 unique or different barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 5, at least 10, at least 20, at least 25, at least 50, at least 75, at least 100, at least 200, at least 500, at least 1000, at least 5000, or at least 10,000 barcode regions, wherein each barcode region is as defined herein; and a barcoded oligonucleotide annealed to each barcode region, wherein each barcoded oligonucleotide is as defined herein. Preferably, the multimeric barcoding reagent comprises at least 5 barcode regions, wherein each barcode region is as defined herein; and a barcoded oligonucleotide annealed to each barcode region, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 unique or different barcode regions, wherein each barcode region is as defined herein; and a barcoded oligonucleotide annealed to each barcode region, wherein each barcoded oligonucleotide is as defined herein. Preferably, the multimeric barcoding reagent comprises at least 5 unique or different barcode regions, wherein each barcode region is as defined herein; and a barcoded oligonucleotide annealed to each barcode region, wherein each barcoded oligonucleotide is as defined herein.

FIG. 1 shows a multimeric barcoding reagent, including first (D1, E1, and F1) and second (D2, E2, and F2) barcode molecules, which each include a nucleic acid sequence comprising a barcode region (E1 and E2). These first and second barcode molecules are linked together, for example by a connecting nucleic acid sequence (S). The multimeric barcoding reagent also comprises first (A1, B1, C1, and G1) and second (A2, B2, C2, and G2) barcoded oligonucleotides. These barcoded oligonucleotides each comprise a barcode region (B1 and B2) and a target region (G1 and G2).

The barcode regions within the barcoded oligonucleotides may each contain a unique sequence which is not present in other barcoded oligonucleotides, and may thus serve to uniquely identify each such barcode molecule. The target regions may be used to anneal the barcoded oligonucleotides to sub-sequences of target nucleic acids, and then may be used as primers for a primer-extension reaction or an amplification reaction e.g. a polymerase chain reaction.

Each barcode molecule may optionally also include a 5' adapter region (F1 and F2). The barcoded oligonucleotides may then also include a 3' adapter region (C1 and C2) that is complementary to the 5' adapter region of the barcode molecules.

Each barcode molecule may optionally also include a 3' region (D1 and D2), which may be comprised of identical sequences within each barcode molecule. The barcoded oligonucleotides may then also include a 5' region (A1 and A2) which is complementary to the 3' region of the barcode molecules. These 3' regions may be useful for manipulation or amplification of nucleic acid sequences, for example sequences that are generated by labeling a nucleic acid target with a barcoded oligonucleotide. The 3' region may comprise at least 4, at least 5, at least 6, at least 8, at least 10, at least 15, at least 20, at least 25, at least 50, at least 100, or at least 250 nucleotides. Preferably, the 3' region comprises at least 4 nucleotides. Preferably each 3' region comprises deoxyribonucleotides, optionally all of the nucleotides in an 3' region are deoxyribonucleotides. One or more of the deoxyribonucleotides may be a modified deoxyribonucleotide (e.g. a deoxyribonucleotide modified with a biotin moiety or a deoxyuracil nucleotide). Each 3' region may comprise one or more universal bases (e.g. inosine), one or modified nucleotides and/or one or more nucleotide analogues.

The invention further provides a library of multimeric barcoding reagents comprising first and second multimeric barcoding reagents as defined herein, wherein the barcode regions of the first multimeric barcoding reagent are different to the barcode regions of the second multimeric barcoding reagent.

The invention provides a library of multimeric barcoding reagents comprising at least 10 multimeric barcoding reagents for labelling a target nucleic acid for sequencing, wherein each multimeric barcoding reagent comprises: first and second barcode molecules comprised within a (single) nucleic acid molecule, wherein each of the barcode molecules comprises a nucleic acid sequence comprising a barcode region; and first and second barcoded oligonucleotides, wherein the first barcoded oligonucleotide comprises, optionally in the 5' to 3' direction, a barcode region complementary and annealed to the barcode region of the first barcode molecule and a target region capable of annealing or ligating to a first sub-sequence of the target nucleic acid, and wherein the second barcoded oligonucleotide comprises, optionally in the 5' to 3' direction, a barcode region complementary and annealed to the barcode region of the second barcode molecule and a target region capable of annealing or ligating to a second sub-sequence of the target nucleic acid.

The barcode regions of the first and second barcode molecules of each multimeric barcoding reagent may be different to the barcode regions of at least 9 other multimeric barcoding reagents in the library.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 5 multimeric barcoding reagents as defined herein. Preferably, the barcode regions of each of the multimeric barcoding reagents may be different to the barcode regions of the other multimeric barcoding reagents.

The barcode regions of each multimeric barcoding reagent may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. Preferably, the barcode regions of each multimeric barcoding reagent are different to the barcode regions of at least 999 (i.e. $10^3$-1) other multimeric barcoding reagents in the library.

Methods of Preparing a Nucleic Acid Sample for Sequencing

The invention may be used to prepare a range of different nucleic acid samples for sequencing. The target nucleic acids may be DNA molecules (e.g. genomic DNA molecules) or RNA molecules (e.g. mRNA molecules). The target nucleic acids may be from any sample. For example, an individual cell (or cells), a tissue, a bodily fluid (e.g. blood, plasma and/or serum), a biopsy or a formalin-fixed paraffin-embedded (FFPE) sample.

The invention provides a method of preparing a nucleic acid sample for sequencing, wherein the method comprises the steps of: contacting the nucleic acid sample with a multimeric barcoding reagent as defined herein; annealing the target region of the first barcoded oligonucleotide to a first sub-sequence of a target nucleic acid, and annealing the target region of the second barcoded oligonucleotide to a second sub-sequence of the target nucleic acid; and extending the first and second barcoded oligonucleotides to produce first and second different barcoded target nucleic acid molecules, wherein each of the barcoded target nucleic acid molecules comprises at least one nucleotide synthesised from the target nucleic acid as a template.

In any method of preparing a nucleic acid sample for sequencing, either the nucleic acid molecules within the nucleic acid sample, and/or the multimeric barcoding reagents, may be present at particular concentrations within the solution volume, for example at concentrations of at least 100 nanomolar, at least 10 nanomolar, at least 1 nanomolar, at least 100 picomolar, at least 10 picomolar, or at least 1 picomolar. The concentrations may be 1 picomolar to 100 nanomolar, 10 picomolar to 10 nanomolar, or 100 picomolar to 1 nanomolar. Alternative higher or lower concentrations may also be used.

The method of preparing a nucleic acid sample for sequencing may comprise contacting the nucleic acid sample with a library of multimeric barcoding reagents as defined herein, and wherein: the barcoded oligonucleotides of the first multimeric barcoding reagent anneal to sub-sequences of a first target nucleic acid and first and second different barcoded target nucleic acid molecules are produced, wherein each barcoded target nucleic acid molecule comprises at least one nucleotide synthesised from the first target nucleic acid as a template; and the barcoded oligonucleotides of the second multimeric barcoding reagent anneal to sub-sequences of a second target nucleic acid and first and second different barcoded target nucleic acid molecules are produced, wherein each barcoded target nucleic acid molecule comprises at least one nucleotide synthesised from the second target nucleic acid as a template.

Each barcoded target nucleic acid molecule may comprise at least 5, at least 10, at least 25, at least 50, at least 100, at least 250, at least 500, at least 1000, at least 2000, at least 5000, or at least 10,000 nucleotides synthesised from the target nucleic acid as template. Preferably, each barcoded target nucleic acid molecule comprises at least 5 nucleotides synthesised from the target nucleic acid as template.

The target nucleic acid may in an intact nucleic acid molecule, co-localised fragments of a nucleic acid molecule, or nucleic acid molecules from a single cell. Preferably, the target nucleic acid is a single intact nucleic acid molecule, two or more co-localised fragments of a single nucleic acid molecule, or two or more nucleic acid molecules from a single cell.

The method of preparing a nucleic acid sample for sequencing may comprise producing at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules.

In the method the barcoded oligonucleotides may be isolated from the nucleic acid sample after annealing to the sub-sequences of the target nucleic acid and before the barcoded target nucleic acid molecules are produced. Additionally or alternatively, the barcoded target nucleic acid molecules may be isolated from the nucleic acid sample.

The step of extending the barcoded oligonucleotides may be performed while the barcoded oligonucleotides are annealed to the barcode molecules.

FIG. 2 shows a method of preparing a nucleic acid sample for sequencing, in which a multimeric barcoding reagent defined herein (for example, as illustrated in FIG. 1) is used to label and extend two or more nucleic acid sub-sequences in a nucleic acid sample. In this method, a multimeric barcoding reagent is synthesised which incorporates at least a first (A1, B1, C1, and G1) and a second (A2, B2, C2, and G2) barcoded oligonucleotide, which each comprise both a barcode region (B1 and B2) and a target region (G1 and G2 respectively).

A nucleic acid sample comprising a target nucleic acid is contacted or mixed with the multimeric barcoding reagent, and the target regions (G1 and G2) of two or more barcoded oligonucleotides are allowed to anneal to two or more corresponding sub-sequences within the target nucleic acid (H1 and H2). Following the annealing step, the first and second barcoded oligonucleotides are extended (e.g. with the target regions serving as primers for a polymerase) into the sequence of the target nucleic acid, such that at least one nucleotide of a sub-sequence is incorporated into the extended 3' end of each of the barcoded oligonucleotides. This method creates barcoded target nucleic acid molecules, wherein two or more sub-sequences from the target nucleic acid are labeled by a barcoded oligonucleotide.

Alternatively, the method may further comprise the step of dissociating the barcoded oligonucleotides from the barcode molecules before annealing the target regions of the barcoded oligonucleotides to sub-sequences of the target nucleic acid.

FIG. 3 shows a method of preparing a nucleic acid sample for sequencing, in which a multimeric barcoding reagent described herein (for example, as illustrated in FIG. 1) is used to label and extend two or more nucleic acid sub-sequences in a nucleic acid sample, but wherein the barcoded oligonucleotides from the multimeric barcoding reagent are dissociated from the barcode molecules prior to annealing to (and extension of) target nucleic acid sequences. In this method, a multimeric barcoding reagent is synthesised which incorporates at least a first (A1, B1, C1, and G1) and a second (A2, B2, C2, and G2) barcoded oligonucleotide, which each comprise a barcode region (B1 and B2) and a target region (G1 and G2).

A nucleic acid sample comprising a target nucleic acid is contacted with the multimeric barcoding reagent, and then the barcoded oligonucleotides are dissociated from the barcode molecules. This step may be achieved, for example, through exposing the reagent to an elevated temperature (e.g. a temperature of at least 35° C., at least 40° C., at least 45° C., at least 50° C., at least 55° C., at least 60° C., at least 65° C., at least 70° C., at least 75° C., at least 80° C., at least 85° C., or at least 90° C.) or through a chemical denaturant, or a combination thereof. This step may also denature double-stranded nucleic acids within the sample itself. The barcoded oligonucleotides may then be allowed to for diffuse for a certain amount of time (e.g. at least 5 seconds, at least 15 seconds, at least 30 seconds, at least 60 seconds, at least 2 minutes, at least 5 minutes, at least 15 minutes, at least 30 minutes, or at least 60 minutes) (and correspondingly, to diffuse a certain physical distance within the sample).

The conditions of the reagent-sample mixture may then be changed to allow the target regions (G1 and G2) of two or more barcoded oligonucleotides to anneal to two or more corresponding sub-sequences within the target nucleic acid (H1 and H2). This could comprise, for example, lowering the temperature of the solution to allow annealing (for example, lowering the temperature to less than 90° C., less than 85° C., less than 70° C., less than 65° C., less than 60° C., less than 55° C., less than 50° C., less than 45° C., less than 40° C., less than 35° C., less than 30° C., less than 25° C., or less than 20° C.). Following this annealing step (or for example, following a purification/preparation step), the first and second barcoded oligonucleotides are extended (e.g. with the target regions serving as primers for a polymerase) into the sequence of the target nucleic acid, such that at least one nucleotide of a sub-sequence is incorporated into the extended 3' end of each of the barcoded oligonucleotides.

This method creates barcoded target nucleic acid molecules wherein two or more sub-sequences from the nucleic acid sample are labeled by a barcoded oligonucleotide. In addition, the step of dissociating the barcoded oligonucleotides and allowing them to diffuse through the sample holds advantages for particular types of samples. For example, cross-linked nucleic acid samples (e.g. formalin-fixed, paraffin-embedded (FFPE) samples) may be amenable to the diffusion of relatively small, individual barcoded oligonucleotides. This method may allow labeling of nucleic acid samples with poor accessibility (e.g. FFPE samples) or other biophysical properties e.g. where target nucleic acid sub-sequences are physically far away from each other.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

Prior to contacting the nucleic acid sample with a multimeric barcoding reagent, or library of multimeric barcoding reagents, as defined herein, a coupling sequence may be added to the 5' end or 3' end of two or more target nucleic acids of the nucleic acid sample (e.g. a FFPE DNA sample). In this method, the target regions may comprise a sequence that is complementary to the coupling sequence. The coupling sequence may comprise a homopolymeric 3' tail (e.g. a poly(A) tail). The coupling sequence may be added by a terminal transferase enzyme. In the method in which the coupling sequence comprises a poly(A) tail, the target regions may comprise a poly(T) sequence. Such coupling sequences may be added following a high-temperature incubation of the nucleic acid sample, to denature the nucleic acids contained therein prior to adding a coupling sequence.

Alternatively, a coupling sequence could be added by digestion of a target nucleic acid sample (e.g. an FFPE DNA sample) with a restriction enzyme, in which case a coupling sequence may be comprised of one or more nucleotides of a restriction enzyme recognition sequence. In this case, a coupling sequence may be at least partially double-stranded, and may comprise a blunt-ended double-stranded DNA sequence, or a sequence with a 5' overhang region of 1 or more nucleotides, or a sequence with a 3' overhang region of 1 or more nucleotides. In these cases, target regions in multimeric barcoding reagents may then comprise sequences that are either double-stranded and blunt-ended (and thus able to ligate to blunt-ended restriction digestion products), or the target regions may contain 5' or 3' overhang sequences of 1 or more nucleotides, which make them cohesive (and thus able to anneal with and ligate to) against said restriction digestion products.

The method may comprise preparing two or more independent nucleic acid samples for sequencing, wherein each nucleic acid sample is prepared using a different library of multimeric barcoding reagents (or a different library of multimeric barcode molecules), and wherein the barcode regions of each library of multimeric barcoding reagents (or multimeric barcode molecules) comprise a sequence that is different to the barcode regions of the other libraries of multimeric barcoding reagents (or multimeric barcode molecules). Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcoding reagents (or multimeric barcode molecules) that was used in its preparation and thereby to identify the nucleic acid sample from which it was prepared.

The invention provides a method of preparing a nucleic acid sample for sequencing, wherein the method comprises the steps of: (a) contacting the nucleic acid sample with a multimeric barcoding reagent, wherein each barcoded oligonucleotide comprises in the 5' to 3' direction a target region and a barcode region, and first and second target primers; (b) annealing the target region of the first barcoded oligonucleotide to a first sub-sequence of a target nucleic acid and annealing the target region of the second barcoded oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; and (e) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different, and wherein each of the barcoded target nucleic acid molecules comprises at least one nucleotide synthesised from the target nucleic acid as a template.

In the method, steps (b) and (c) may be performed at the same time.

Methods of Synthesising a Library of Nucleic Acid Barcode Molecules

The invention further provides a method of synthesising a library of nucleic acid barcode molecules comprising: contacting a first library of single-stranded sub-barcode molecules with a second library of single-stranded sub-barcode molecules, wherein each sub-barcode molecule comprises in the 5' to 3' direction a sub-barcode region and a downstream region, and wherein the downstream regions of sub-barcodes molecules from the first library are capable of annealing to the downstream regions of sub-barcode molecules from the second library; annealing the downstream region of a first sub-barcode molecule from the first library to the downstream region of a first sub-barcode molecule from the second library, and annealing the downstream region of a second sub-barcode molecule from the first library to the downstream region of a second sub-barcode molecule from the second library; and extending the 3' ends of the sub-barcode molecules to produce first and second double-stranded barcode molecules.

Each sub-barcode molecule may further comprise an upstream region, and therefore comprise in the 5' to 3' direction an upstream region, a sub-barcode region and a downstream region.

Preferably each sub-barcode molecule comprises or consists of deoxyribonucleotides. One or more of the deoxyribonucleotides may be a modified deoxyribonucleotide (e.g. a deoxyribonucleotide modified with a biotin moiety or a deoxyuracil nucleotide). Preferably each sub-barcode region comprises or consists of deoxyribonucleotides. One or more of the deoxyribonucleotides may be a modified deoxyribonucleotide (e.g. a deoxyribonucleotide modified with a biotin moiety or a deoxyuracil nucleotide). Each sub-barcode region may comprise at least 2, at least 3, at least 4, at least 5, at least 10, at least 15, at least 20, at least 25 or at least 50 nucleotides. Preferably, each sub-barcode region comprises at least 2 nucleotides.

The first and second libraries of sub-barcode molecules may each comprise at least 10, at least 50, at least 100, at least 250, at least 500, at least $10^3$, at least $10^4$ or at least $10^5$ different sub-barcode molecules. The sub-barcode region of each sub-barcode molecule in the first library may be different to one or more (or all) of the other sub-barcode regions of the other sub-barcode molecules of the first library. The sub-barcode region of each sub-barcode molecule in the second library may be different to one or more (or all) of the other sub-barcode regions of the other sub-barcode molecules of the second library.

The method may be used to synthesise a library of at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$ or at least $10^{12}$ different barcode molecules. Preferably, the method is used to synthesise a library of at least 100 different barcode molecules.

Each barcode molecule may comprise at least 2, at least 3, at least 4, at least 5, at least 10, at least 15, at least 20 or at least 25 sub-barcode molecules. Preferably, each barcode molecule comprises at least 2 sub-barcode molecules.

Each barcode molecule may comprise at least 2, at least 3, at least 4, at least 5, at least 10, at least 15, at least 20 or at least 25 sub-barcode regions. Preferably, each barcode molecule comprises at least 2 sub-barcode regions.

The method may further comprise the step of dissociating the first and second double-stranded barcode molecules to produce first and second single-stranded barcode molecules.

FIG. 4 shows a method of creating a library of barcode molecules from sub-barcode libraries. In the method a first (L1, M1, N1) and second (L2, M2, N2) sub-barcode molecule from a first sub-barcode library are mixed with a first (O1, P1, Q1) and second (O2, P2, Q2) sub-barcode molecule from a second sub-barcode library. Each sub-barcode molecule from the first sub-barcode library includes a sub-barcode region (M1 and M2), each of which may be different to one or more (or all) of the other sub-barcode regions of the other sub-barcode molecules of the library. Each sub-barcode molecule from the first sub-barcode library also includes an upstream region (L1 and L2) and a downstream region (N1 and N2); the upstream and/or the downstream regions may be identical in all sub-barcode molecules of the first sub-barcode library.

Each sub-barcode molecule from the second sub-barcode library includes a sub-barcode region (P1 and P2), each of which may be different to one or more (or all) of the other sub-barcode regions of the other sub-barcode molecules of the library. Each sub-barcode molecule from the second sub-barcode library also includes an upstream region (O1 and O2) and a downstream region (Q1 and Q2); the upstream and/or the downstream regions may be identical in all sub-barcode molecules of the second sub-barcode library.

In this method, the downstream regions of the sub-barcode molecules of the second library (Q1 and Q2) are complementary to the downstream regions of the sub-barcode molecules of the first library (N1 and N2). After mixing, the downstream regions Q1 and Q2 are allowed to anneal to the downstream regions N1 and N2 to produce partially-duplex nucleotide molecules (the annealing step). The 3' ends of each molecule are then extended with a polymerase and a primer-extension reaction to create first and second barcode molecules. Each barcode molecule being a double-stranded, combined barcode molecule comprising the sub-barcode region of a molecule from the first sub-barcode library on the same nucleic acid molecule as a sub-barcode region of a molecule from the second sub-barcode library. The first barcode molecule and the second barcode molecule may form part of a larger barcode molecule library.

This method may be further repeated to combine third, fourth, or further sub-barcode libraries into barcode molecule libraries, wherein the addition of further sub-barcode molecules (from further sub-barcode libraries) into established barcode molecules (from a barcode molecule) involves an annealing step and then an extension step as illustrated in FIG. 4 for first and second sub-barcode libraries.

By this method, it is possible to create a complex library of barcode molecules with a comparatively small number of sub-barcode molecules. Since each sub-barcode combination step forms a combinatoric reaction, the number of potential barcode molecules scales exponentially as a function of the number of input sub-barcode molecules.

The invention further provides a method of synthesising a library of nucleic acid barcode molecules comprising: contacting a first library of sub-barcode molecules with a second library of sub-barcode molecules, wherein each sub-barcode molecule comprises a sub-barcode region; and ligating a first sub-barcode molecule from the first library to a first sub-barcode molecule from the second library to form a first barcode molecule, and ligating a second sub-barcode molecule from the first library to a second sub-barcode molecule from the second library to form a second barcode molecule.

Preferably each sub-barcode molecule comprises or consists of deoxyribonucleotides. One or more of the deoxyribonucleotides may be a modified deoxyribonucleotide (e.g. a deoxyribonucleotide modified with a biotin moiety or a deoxyuracil nucleotide). Preferably each sub-barcode region comprises or consists of deoxyribonucleotides. One or more of the deoxyribonucleotides may be a modified deoxyribonucleotide (e.g. a deoxyribonucleotide modified with a biotin moiety or a deoxyuracil nucleotide). Each sub-barcode region may comprise at least 2, at least 3, at least 4, at least 5, at least 10, at least 15, at least 20 or at least 25 nucleotides. Preferably, each sub-barcode region comprises at least 2 nucleotides.

The first and second libraries of sub-barcode molecules may each comprise at least 10, at least 50, at least 100, at least 250, at least 500, at least $10^3$, at least $10^4$ or at least $10^5$ different sub-barcode molecules. The sub-barcode region of each sub-barcode molecule in the first library may be different to one or more (or all) of the other sub-barcode regions of the other sub-barcode molecules of the first library. The sub-barcode region of each sub-barcode molecule in the second library may be different to one or more (or all) of the other sub-barcode regions of the other sub-barcode molecules of the second library.

The method may be used to synthesise a library of at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$ or at least $10^{12}$ different barcode molecules. Preferably, the method is used to synthesise a library of at least 100 different barcode molecules.

Each barcode molecule may comprise at least 2, at least 3, at least 4, at least 5, at least 10, at least 15, at least 20 or at least 25 sub-barcode molecules. Preferably, each barcode molecule comprises at least 2 sub-barcode molecules.

Each barcode molecule may comprise at least 2, at least 3, at least 4, at least 5, at least 10, at least 15, at least 20 or at least 25 sub-barcode regions. Preferably, each barcode molecule comprises at least 2 sub-barcode regions.

The sub-barcode molecules of the first and second libraries may be single-stranded nucleic acids or double-stranded nucleic acids.

Each sub-barcode molecule of the first library may further comprise an upstream region and therefore comprise in the 5' to 3' direction the upstream region and the sub-barcode region.

Each sub-barcode molecule of the second library may further comprise a downstream region and therefore comprises in the 5' to 3' direction the sub-barcode region and the downstream region.

FIG. 5 shows a method of synthesising a library of barcode molecules from sub-barcode libraries by ligation. In this method a first (L1, M1, N1) and second (L2, M2, N2) sub-barcode molecule from a first sub-barcode library are mixed with a first (O1, P1, Q1) and second (O2, P2, Q2) sub-barcode molecule from a second sub-barcode library. Each sub-barcode molecule from the first sub-barcode library includes a sub-barcode region (M1 and M2), each of which may be different to one or more (or all) of the other sub-barcode regions of the other sub-barcode molecules of the library. Each sub-barcode molecule from the first sub-barcode library also includes an upstream region (L1 and L2) and a downstream region (N1 and N2); the upstream and/or the downstream regions may be identical in all sub-barcode molecules of the first sub-barcode library. Each sub-barcode molecule may be synthesised to include a 5'-terminal phosphate group.

Each sub-barcode molecule from the second sub-barcode library includes a sub-barcode region (P1 and P2), each of which may be different to one or more (or all) of the other sub-barcode regions of the other sub-barcode molecules of the library. Each sub-barcode molecule from the second sub-barcode library also includes an upstream region (O1 and O2) and a downstream region (Q1 and Q2); the upstream and/or the downstream regions may be identical in all sub-barcode molecules of the second sub-barcode library.

In this method, a first and second sub-barcode molecule from a first sub-barcode library are mixed with a first and second sub-barcode molecule from a second sub-barcode library, and then a first sub-barcode molecule from the first sub-barcode library is ligated to a first sub-barcode molecule from the second sub-barcode library to form a first barcode molecule, and a second sub-barcode molecule from the first sub-barcode library is ligated to a second sub-barcode molecule from the second sub-barcode library to form a second barcode molecule, wherein this ligation is performed by a single stranded ligase enzyme. The first barcode molecule and the second barcode molecule may form part of a larger barcode molecule library.

This process may be further repeated to combine third, fourth, or further sub-barcode libraries into barcode molecule libraries, wherein the addition of further sub-barcode molecules (from further sub-barcode libraries) into established barcode molecules (from a barcode molecule library) involves a ligation step as illustrated in FIG. 5 for first and second sub-barcode libraries.

By this method, it is possible to create a complex library of barcode molecules with a comparatively small number of sub-barcode molecules. Since each sub-barcode combination step forms a combinatoric reaction, the number of potential barcode molecules scales exponentially as a function of the number of input sub-barcode molecules.

The invention further provides a method of synthesising a library of nucleic acid barcode molecules comprising: contacting a first library of sub-barcode molecules with a second library of sub-barcode molecules, wherein each sub-barcode molecule comprises a sub-barcode region; and ligating a first sub-barcode molecule from the first library to a first sub-barcode molecule from the second library to form a first barcode molecule, and ligating a second sub-barcode molecule from the first library to a second sub-barcode molecule from the second library to form a second barcode molecule. The method preferably requires that: (a) each sub-barcode molecule of the first library further comprises an upstream region, and wherein each sub-barcode molecule of the first library comprises in the 5' to 3' direction the upstream region and the sub-barcode region; (b) each sub-barcode molecule of the second library further comprises a downstream region, and wherein each sub-barcode molecule of the second library comprises in the 5' to 3' direction the sub-barcode region and the downstream region; (c) the first barcode molecule comprises in the 5'-3' direction the upstream region of the first sub-barcode molecule of the first library, the sub-barcode region of the first sub-barcode molecule of the first library, the sub-barcode region of the first sub-barcode molecule of the second library and the downstream region of the first sub-barcode molecule of the second library; and (d) the second barcode molecule comprises in the 5'-3' direction the upstream region of the second sub-barcode molecule of the first library, the sub-barcode region of the second sub-barcode molecule of the first library, the sub-barcode region of the second sub-barcode molecule of the second library and the downstream region of the second sub-barcode molecule of the second library.

Preferably the upstream region of each sub-barcode molecule of the first library comprises an upstream recognition site for a restriction endonuclease, optionally wherein the upstream recognition site is adjacent to the sub-barcode region. The recognition site of the restriction endonuclease may be positioned 1, 2, less than 3, less than 4, less than 5 or less than 10 nucleotides upstream of the sub-barcode region of the sub-barcode molecule. Additionally or alternatively, the downstream region of each sub-barcode molecule of the second library comprises a downstream recognition site for a restriction endonuclease, optionally wherein the downstream recognition site is adjacent to the sub-barcode region. The recognition site of the restriction endonuclease may be positioned 1, 2, less than 3, less than 4, less than 5 or less than 10 nucleotides downstream of the sub-barcode region of the sub-barcode molecule.

The method may further comprise the step of cleaving the barcode molecules at the upstream recognition site and/or the downstream recognition site using a restriction endonuclease. Preferably the barcode molecules are amplified e.g. by PCR before being cleaved. Preferably the amplified products are modified by reaction with a uracil DNA glycosylase enzyme.

The method may further comprise the steps of: (a) contacting the barcode molecules cleaved at the downstream recognition site with a further library of sub-barcode molecules, wherein each sub-barcode molecule of the further library comprises in the 5' to 3' direction a sub-barcode region and a downstream region; and (b) ligating the first barcode molecule cleaved at the downstream recognition site to a first sub-barcode molecule of the further library to form a first extended barcode molecule, and ligating the second barcode molecule cleaved at the downstream recognition site to a second sub-barcode molecule of the further library to form a second extended barcode molecule. The first extended barcode molecule comprises in the 5'-3' direction the upstream region of the first sub-barcode molecule of the first library, the sub-barcode region of the first sub-barcode molecule of the first library, the sub-barcode region of the first sub-barcode molecule of the second library, the sub-barcode region of the first sub-barcode molecule of the further library and the downstream region of the first sub-barcode molecule of the further library. The second extended barcode molecule comprises in the 5'-3' direction the upstream region of the second sub-barcode molecule of the first library, the sub-barcode region of the second sub-barcode molecule of the first library, the sub-barcode region of the second sub-barcode molecule of the second library, the sub-barcode region of the second sub-barcode molecule of the further library and the downstream region of the second sub-barcode molecule of the further library.

The downstream region of each sub-barcode molecule of the further library may comprise a downstream recognition site for a restriction endonuclease, optionally wherein the downstream recognition site is adjacent to the sub-barcode region. The recognition site of the restriction endonuclease may be positioned 1, 2, less than 3, less than 4, less than 5 or less than 10 nucleotides downstream of the sub-barcode region of the sub-barcode molecule.

The method may further comprise the steps of: (a) contacting the barcode molecules cleaved at the upstream recognition site with a further library of sub-barcode molecules, wherein each sub-barcode molecule of the further library comprises in the 5' to 3' direction an upstream region and a sub-barcode region; and (b) ligating the first barcode molecule cleaved at the upstream recognition site to a first sub-barcode molecule of the further library to form a first extended barcode molecule, and ligating the second barcode molecule cleaved at the upstream recognition site to a second sub-barcode molecule of the further library to form a second extended barcode molecule. The first extended barcode molecule comprises in the 5'-3' direction the upstream region of the first sub-barcode molecule of the further library, the sub-barcode region of the first sub-barcode molecule of the further library, the sub-barcode region of the first sub-barcode molecule of the first library, the sub-barcode region of the first sub-barcode molecule of the second library and the downstream region of the first sub-barcode molecule of the second library. The second extended barcode molecule comprises in the 5'-3' direction the upstream region of the second sub-barcode molecule of the further library, the sub-barcode region of the second sub-barcode molecule of the further library, the sub-barcode region of the second sub-barcode molecule of the first library, the sub-barcode region of the second sub-barcode molecule of the second library and the downstream region of the second sub-barcode molecule of the second library.

The upstream region of each sub-barcode molecule of the further library may comprise an upstream recognition site for a restriction endonuclease, optionally wherein the upstream recognition site is adjacent to the sub-barcode region. The recognition site of the restriction endonuclease may be positioned 1, 2, less than 3, less than 4, less than 5 or less than 10 nucleotides upstream of the sub-barcode region of the sub-barcode molecule.

The method may further comprise the steps of: (a) cleaving the extended barcode molecules at the downstream recognition site or the upstream recognition site of the sub-barcode molecule of the further library; and (b) ligating the cleaved extended barcode molecules with a further library of sub-barcode molecules by the steps defined herein. Steps (a) and (b) may be repeated at least 2, at least 3, at least 4, at least 5, at least 6, at least 7, at least 8, at least 9, at least 10, or at least 25 times. Preferably the extended barcode molecules are amplified e.g. by PCR before being cleaved. Preferably the amplified products are modified by reaction with a uracil DNA glycosylase enzyme.

FIG. 6 shows a method of synthesising a library of barcode molecules by ligation and cleavage. In this method the ends of two different sub-barcode molecules are ligated to each other in a double-stranded ligation reaction to create concatenated first and second barcode molecules, and wherein these ligated molecules are subsequently cleaved with a restriction enzyme to allow sub-barcode regions from two or more sub-barcode molecules to be ligated directly to the sub-barcode regions of the cleaved first and second barcode molecules. This method enables sub-barcode regions to be ligated together without intervening non-barcode (constant) sequence.

In this method, a first (L1, M1) and second (L2, M2) sub-barcode molecule from a first sub-barcode library are mixed with a first (P1, Q1) and second (P2, Q2) sub-barcode molecule from a second sub-barcode library. These first and second sub-barcode molecules exist in double-stranded form, with a blunt end on the end to be ligated. Each sub-barcode molecule from the first sub-barcode library includes a sub-barcode region (M1 and M2), each of which may be different to one or more (or all) of the other sub-barcode regions of the other sub-barcode molecules of the library. Each sub-barcode molecule from the first sub-barcode library also includes an upstream region (L1 and L2) which may be the same in each molecule of the library. Each sub-barcode molecule may be synthesised to include a 5'-terminal phosphate group.

Each sub-barcode molecule from the second sub-barcode library includes a sub-barcode region (P1 and P2), each of which may be different to one or more (or all) of the other sub-barcode regions of the other sub-barcode molecules of the library. Each sub-barcode molecule from the second sub-barcode library also includes a downstream region (Q1 and Q2) which may be the same in each molecule of the library.

In this method, a first and second sub-barcode molecule from a first sub-barcode library are mixed with a first and second sub-barcode molecule from a second sub-barcode library, and a first sub-barcode molecule from the first sub-barcode library is ligated to a first sub-barcode molecule from the second sub-barcode library to form a first barcode molecule, and a second sub-barcode molecule from the first sub-barcode library is ligated to a second sub-barcode molecule from the second sub-barcode library to form a second barcode molecule, wherein this ligation is a blunt-ended ligation performed by a double-stranded ligase enzyme. Optionally, following this ligation step, an amplification reaction may be performed on the ligation products (i.e. the first and second barcode molecules), for example by using primers located within the L and Q regions. These primers may include one or more deoxyuracil nucleotides to enable subsequent modification by a DNA glycosylase enzyme following amplification, to prevent amplification of carried-over but unligated template molecules in subsequent amplification steps.

Following ligation (and amplification if performed), a restriction endonuclease (e.g. Mlyl) is used to cleave the products. The recognition site for the restriction endonuclease (e.g. Mlyl) may be included within the L1 and L2 regions such that the enzyme cleaves at the nucleotide bond directly between the first (L1-M1) and second (L2-M2) junctions between the upstream region and the sub-barcode region. This reaction creates a blunt end on the first (M1) and second (M2) barcode molecules.

The first and second barcode molecules with blunt ends are then ligated to first (T1-U1) and second (T2-U2) sub-barcode molecules of a further library of sub-barcode molecules to form first and second extended barcode molecules. Each sub-barcode molecule from the further sub-barcode library includes a sub-barcode region (U1 and U2), each of which may be different to one or more (or all) of the other sub-barcode regions of the other sub-barcode molecules of the library. Each sub-barcode molecule from the further sub-barcode library also includes an upstream region (T1 and T2) which may be the same in each molecule of the library.

This process may be repeated to combine third, fourth, or further libraries of sub-barcode molecules into barcode molecule libraries, wherein each step involves a ligation step to combine two or more sub-barcode molecules from a further library with two or more extended barcode molecules, wherein each ligation step involves ligation of an additional sub-barcode molecule to an existing blunt-end extended barcode molecule which has been created by a restriction endonuclease mediated cleavage reaction (e.g. using Mlyl). Subsequent steps may also include the addition of further adapter sequences, for use in amplifying, further ligating, or further manipulating the (extended) barcode molecules.

A further method of synthesising a library of nucleic acid barcode molecules requires that each sub-barcode molecule of the first library is double-stranded and comprises in the 5' to 3' direction an upstream region and a sub-barcode region. In this method, prior to the step of contacting a first library of sub-barcode molecules with a second library of sub-barcode molecules, the first library of sub-barcode molecules is ligated to a double-stranded downstream adapter molecule comprising a downstream adapter region to produce a library of ligation products, wherein the ligation may be achieved by blunt-ended ligation, such that each molecule then comprises, in the 5' to 3' direction, the upstream region of a first sub-barcode molecule, and then the sub-barcode region of the first sub-barcode molecule, and then the downstream adapter region. The downstream adapter molecule may comprise a 5' phosphate group on the 5' end that is ligated to the sub-barcode molecule in said ligation reaction. The method may further comprise amplifying the library of ligation products to produce a library of amplified products, wherein the upstream region of each sub-barcode molecule comprises a forward priming sequence and the downstream adapter region comprises a reverse priming sequence, and wherein the step of amplifying is performed using a forward primer that anneals to the forward priming sequence and a reverse primer that anneals to the reverse priming sequence, optionally wherein the step of amplifying is by PCR. The method may further comprise modifying the library of amplified products by reaction with a uracil DNA glycosylase enzyme, wherein the forward primer and/or the reverse primer comprises at least one deoxyuracil nucleotide. The upstream region of each sub-barcode molecule may comprise a recognition site of a restriction endonuclease, and wherein the recognition site is positioned such that cleavage at the recognition site by a restriction endonuclease (e.g. Mlyl) occurs adjacent to the sub-barcode region of the sub-barcode molecule. The recognition site of the restriction endonuclease may be positioned 1, 2, less than 3, less than 4, less than 5 or less than 10 nucleotides upstream of the sub-barcode region of the sub-barcode molecule. The method may further comprise cleaving the library of ligation products or the library of amplified products at the recognition site using a restriction endonuclease to produce a library of cleaved products, optionally wherein the cleavage step is performed after the step of modification by reaction with a uracil DNA glycosylase enzyme.

The method then requires the following steps: contacting the library of cleaved products (i.e. a modified from of the first library of sub-barcode molecules) with a second library of sub-barcode molecules, wherein each sub-barcode molecule of the second library is double-stranded and comprises in the 5' to 3' direction an upstream region and a sub-barcode region; and ligating a first product from the library of cleaved products to a first sub-barcode molecule from the second library to form a first barcode molecule, and ligating a second product from the library of cleaved products to a second sub-barcode molecule from the second library to form a second barcode molecule. The upstream region of each sub-barcode molecule of the second library may comprise a recognition site of a restriction endonuclease (e.g. Mlyl), and the recognition site may be positioned such that cleavage at the recognition site by a restriction endonuclease occurs adjacent to the sub-barcode region of the sub-barcode molecule. The recognition site of the restriction endonuclease may be positioned 1, 2, less than 3, less than 4, less than 5 or less than 10 nucleotides upstream of the sub-barcode region of the first sub-barcode molecule.

In the method, the steps of cleaving and ligation may be repeated 1, 2, 3, 4, or 5 times, wherein each repeat involves the use of a further library of sub-barcode molecules, and optionally wherein each repeat comprises repeating the step of amplification, and further optionally wherein each repeat comprises repeating the step of DNA glycosylase modification.

In the method the last ligation step may comprise the ligation of a double-stranded upstream adapter molecule comprising an upstream adapter region to the library of cleaved products to produce a library of ligation products. The method may further comprise amplifying the library of ligation products using a forward primer that anneals to a forward priming sequence in the upstream adapter region and a reverse primer that anneals to the reverse priming sequence in the downstream adapter region to form a library of amplification products.

Methods of Assembling a Multimeric Barcode Molecule from Barcode Molecules

The invention further provides a method of assembling a library of multimeric barcode molecules from a library of nucleic acid barcode molecules produced by the methods described herein. The method comprises annealing a forward splint primer to the library of ligation products or library of amplification products, wherein the forward splint primer comprises in the 5' to 3' direction a sequence complementary to the reverse primer defined herein, and a sequence substantially identical to the forward primer defined herein, and wherein the 3' end of the forward splint primer is extended to incorporate sequence from the ligation products or amplification products, and optionally wherein the extension reaction is performed using a DNA polymerase.

The method may further comprise annealing a forward termination primer to the ligation products or amplification products, wherein the forward termination primer comprises in the 5' to 3' direction a forward reagent amplification sequence and a sequence substantially identical to the forward primer defined herein, and wherein the 3' end of the forward termination primer is extended to incorporate sequence from the ligation products or amplification products, and optionally wherein the extension reaction is performed using a DNA polymerase.

The method may further comprise annealing a reverse splint primer to the ligation products or amplification products, wherein the reverse splint primer comprises in the 5' to 3' direction a sequence complementary to the forward primer defined herein and a sequence substantially identical to the reverse primer defined herein, and wherein the 3' end of the reverse splint primer is extended to incorporate sequence from the ligation products or amplification products, and optionally wherein the extension reaction is performed using a DNA polymerase.

In any method(s) of synthesising multimeric barcode molecules from barcode molecules that involves forward splint primer(s) and/or reverse splint primer(s), the forward splint primer(s) and/or the reverse splint primer(s) may comprise one or more nucleotides which are not complementary to sequences within the barcode molecules (e.g., are not the same or complementary to the forward primer sequence or the reverse primer sequence of the barcode molecules). The forward splint primer(s) and/or the reverse splint primer(s) may also comprise one or more nucleotide regions that include randomised or degenerate nucleotides (i.e. wherein a given nucleotide position within the splint primer can be occupied by two or more of the four canonical deoxyribonucleotides A/T/G/C); this region of degenerate nucleotides may be located 5' of the 3'-priming region of the splint primer.

The method may further comprise annealing a reverse termination primer to the ligation products or amplification products, wherein the reverse termination primer comprises in the 5' to 3' direction a reverse reagent amplification sequence and a sequence substantially identical to the reverse primer defined herein, and wherein the 3' end of the reverse termination primer is extended to incorporate sequence from the ligation products or amplification products, and optionally wherein the extension reaction is performed using a DNA polymerase.

Following the annealing and extension of the primers, an overlap-extension amplification reaction may be performed with two or more molecules from the annealing and extension process to produce a library of multimeric barcode molecules, optionally wherein the amplification reaction is performed by polymerase chain reaction, wherein each multimeric barcode molecule comprises the barcode regions from at least two barcode molecules.

The method may further comprise amplifying the multimeric barcode molecules using a forward primer substantially identical to the forward reagent amplification sequence and a reverse primer substantially identical to the reverse reagent amplification sequence, wherein the amplification reaction includes at least 1, at least 5, at least 10, at least 15, at least 20, or at least 30 cycles of amplification, optionally wherein the amplification is performed by polymerase chain reaction.

The library of multimeric barcode molecules may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different multimeric barcode molecules. Preferably, the library of multimeric barcode molecules comprises at least 5 barcode molecules.

The method may further comprise a nucleic acid size-selection step to isolate multimeric barcode molecules of a defined length, optionally wherein the length is 900 to 1100 nucleotides, 4500 to 5500 nucleotides or 9000 to 11000 nucleotides. Further optionally wherein the length is approximately 1000 nucleotides, approximately 5000 nucleotides, or approximately 10,000 nucleotides.

The method may further comprise performing one or more primer extension cycles on the amplified multimeric barcode molecules using either a single forward primer substantially identical to the forward reagent amplification sequence, or a single reverse primer substantially identical to the reverse reagent amplification sequence.

The method may comprise the incorporation of one or more modified deoxyribonucleotides during the primer extension cycles, for example a deoxyribonucleotide modified with a biotin moiety or a deoxyuracil nucleotide.

The invention further provides a method of assembling a multimeric barcode molecule from two or more barcode molecules comprising: (a) contacting a first barcode molecule with a first primer and contacting a second barcode molecule with a second primer, wherein each barcode molecule comprises a first strand comprising in the 5' to 3' direction a 5' region, a barcode region and a 3' region; (b) annealing the first primer to the 3' region of the first barcode molecule and the second primer to the 3' region of the second barcode molecule; (c) extending the first primer to synthesise a second strand comprising a sequence complementary to the first strand of the first barcode molecule to form a first double-stranded barcode molecule, and extending the second primer to synthesise a second strand comprising a sequence complementary to the first strand of the second barcode molecule to form a second double-stranded barcode molecule; and (d) ligating the first double-stranded barcode molecule to the second double-stranded barcode molecule.

FIG. 7 shows a method of assembling a multimeric barcode molecule (a precursor to a multimeric barcoding reagent) from two or more barcode molecules. In this method, first (D1, E1, and F1) and second (D2, E2, and F2) single-stranded barcode molecules, which each include a nucleic acid sequence comprising a barcode region (E1 and E2), are first converted into a double-stranded form, by the annealing and then extension of a primer (DS) at its 5' end. This DS primer may be synthesised to include a 5'-terminal phosphate group, to enable a subsequent ligation reaction. This process creates a first and second double-stranded copy of the original first and second barcode molecules respectively.

These double-stranded barcode molecules are then linked together with a double-stranded ligation reaction, to create 'concatenated' molecules containing the first and second barcode molecules and their constituent barcode regions (E1 and E2), linked by a connecting nucleic acid sequence. Optionally, this process may be repeated to concatenate more than two double-stranded barcode molecules into a contiguous, concatenated sequence. Also optionally, this ligation reaction may be conducted at a high concentration of the individual double-stranded barcode molecules, such that concatamerisation of a large number of individual double-stranded barcode molecules into contiguous, concatenated sequences is favoured.

These molecules may then be ligated to first (V) and second (W) amplification adapters using a further double-stranded ligation reaction. These amplification adapters may incorporate sequences for forward and reverse primers respectively, to allow universal amplification of the concatamerised barcode molecules. The first or second strand of these amplified molecules may then be further processed to create functionalised multimeric barcoding reagents, for example as shown in FIG. 9 and FIG. 10.

The invention further provides a method of assembling a double-stranded multimeric barcode molecule from two or more single-stranded barcode molecules, wherein each barcode molecule comprises in the 5' to 3' direction a 5' region, a barcode region and a 3' region, the method comprising: (a) contacting the first barcode molecule with a reverse splint primer, wherein the reverse splint primer comprises a 5' region complementary to the 5' region of the second barcode molecule and a 3' region complementary to the 3' region of the first barcode molecule, and contacting the second barcode molecule with a reverse termination primer, wherein the reverse termination primer comprises a 3' region complementary to the 3' region of the second barcode molecule; (b) annealing the 3' region of the reverse splint primer to the 3' region of the first barcode molecule and annealing the 3' region of the reverse termination primer to the 3' region of the second barcode molecule; (c) extending the reverse splint primer to synthesise a first extension product comprising a sequence complementary to the first barcode molecule, and extending the reverse termination primer to synthesise a second extension product comprising a sequence complementary to the second barcode molecule; (d) contacting the first extension product with a forward termination primer, wherein the forward termination primer comprises a 3' region substantially identical to the 5' region of the first barcode molecule; (e) annealing the 3' region of the forward termination primer to the 3' region of the first extension product; (f) extending the forward termination primer to synthesise a third extension product comprising a sequence complementary to the first extension product; (g) annealing the second and third extension products; and (h) extending the second and the third extension products at the 3' ends to form a double-stranded multimeric barcode molecule that comprises a first strand comprising the sequence of the first barcode molecule linked to the sequence of the second barcode molecule, and a second strand that is complementary to the first strand.

The invention further provides a method of assembling a double-stranded multimeric barcode molecule from two or more single-stranded barcode molecules, wherein each barcode molecule comprises in the 5' to 3' direction a 5' region, a barcode region and a 3' region, the method comprising: (a) contacting the first barcode molecule with a reverse splint primer, wherein the reverse splint primer comprises a 5' region complementary to the 5' region of the second barcode molecule and a 3' region complementary to the 3' region of the first barcode molecule, and contacting the second barcode molecule with a reverse termination primer, wherein the reverse termination primer comprises a 3' region complementary to the 3' region of the second barcode molecule; (b) annealing the 3' region of the reverse splint primer to the 3' region of the first barcode molecule and annealing the 3' region of the reverse termination primer to the 3' region of the second barcode molecule; (c) extending the reverse splint primer to synthesise a first extension product comprising a sequence complementary to the first barcode molecule, and extending the reverse termination primer to synthesise a second extension product comprising a sequence complementary to the second barcode molecule; (d) contacting the first extension product with a forward termination primer, wherein the forward termination primer comprises a 3' region substantially identical to the 5' region of the first barcode molecule, and contacting the second extension product with a forward splint primer, wherein the forward splint primer comprises a 5' region substantially identical to the 3' region of the first barcode molecule and a 3' region substantially identical to the 5' region of the second barcode molecule; (e) annealing the 3' region of the forward termination primer to the 3' region of the first extension product and annealing the 3' region of the forward splint primer to the 3' region of the second extension product; (f) extending the forward termination primer to synthesise a third extension product comprising a sequence complementary to the first extension product, and extending the second extension product using the forward splint primer to synthesise a fourth extension product comprising a sequence complementary to the 5' region of the forward splint primer; (g) annealing the third and fourth extension products; and (h) extending the third and the fourth extension products at the 3' end to form a double-stranded multimeric barcode molecule that comprises a first strand comprising the sequence of the first barcode molecule linked to the sequence of the second barcode molecule, and a second strand that it complementary to the first strand.

In the method the forward termination primer may comprise a 5' region comprising a forward reagent amplification sequence, and the reverse termination primer may comprise a 5' region comprising a reverse reagent amplification sequence.

The method may further comprise amplifying the multimeric barcode molecule using a forward and reverse primer, wherein the forward primer anneals to the forward reagent amplification sequence and the reverse primer anneals to the reverse reagent amplification sequence.

FIG. 8 shows a method of assembling a multimeric barcode molecule (a precursor to a multimeric barcoding reagent) from two or more barcode molecules. The method uses one or more splint primers in an overlap-extension approach.

In this method, first (D1, E1, and F1) and second (D2, E2, and F2) single-stranded barcode molecules, which each include a nucleic acid sequence comprising a barcode region (E1 and E2 respectively), are first annealed to a reverse splint primer (F1' and D2'), which includes a 5' region (D2') complementary to a 5' region of the second barcode molecule (D2), and a 3' region (F1') complementary to a 3' region of the first barcode molecule (F1). The first and second barcode molecules are also annealed to a reverse termination primer (F2' and W), which includes a 5' region comprising a reverse reagent amplification sequence (W), and a 3' region (F2') complementary to a 3' region of the second barcode molecule (F2). A primer extension reaction is then performed along the barcode molecules, with the reverse splint primer and reverse termination primer used to prime the extension reaction.

The resulting primer-extension products are then annealed to a forward splint primer (F1 and D2), which includes a 5' region substantially identical to the 3' region of the first barcode molecule (F1), and a 3' region substantially identical to the 5' region of the second barcode molecule (D2). The primer-extension products are also annealed to a forward termination primer (V and D1), which includes a 5' region comprising a forward reagent amplification sequence (V), and a 3' region substantially identical to the 5' region of the first barcode molecule (D1). A primer extension reaction is then performed, with the forward splint primer and forward termination primers used to prime the extension reaction.

These primer-extended products are then denatured, and the 3' end of the top strand of the first extended product (F1 and D2) is allowed to anneal to the 3' end of the bottom strand of the second extended product (F1' and D2'). The overlapping 3' ends are then extended using a polymerase (e.g. by PCR) such that the individual barcode molecules are then linked together with an overlap-extension reaction, to create 'concatenated' molecules containing the first and second barcode molecules and their constituent barcode regions (E1 and E2), linked by a connecting nucleic acid sequence.

Optionally, this denaturation and overlap-extension process may be repeated two or more times to concatenate more than two barcode molecules into a contiguous, concatenated sequence. Also optionally, the primer-extension reactions may be conducted at a high concentration of the splint primers relative to the concentration of the termination primers, such that overlap-extension of a large number of individual barcode molecules into contiguous, concatenated sequences is favoured.

The incorporated forward reagent amplification sequence (V) and reverse reagent amplification sequence (W) may comprise sequences for forward and reverse primers respectively, to allow universal amplification of the concatamerised barcode molecules. The top or bottom strand of these amplified molecules may then be further processed to create functionalised multimeric barcoding reagents, for example as shown in FIG. 9 and FIG. 10. The forward reagent amplification sequence (V) and reverse reagent amplification sequence (W) may be designed to have particular estimated annealing temperatures during amplification reactions (for example, amplification by PCR), such as 20 to 60 degrees Celsius, 60 to 90 degrees Celsius, 65 to 85 degrees Celsius, 70 to 80 degrees Celsius, or 75 to 90 degrees Celsius.

In the methods of assembling a double-stranded multimeric barcode molecule, the multimeric barcode molecule may be assembled using at least 5, at least 10, at least 20, at least 25, at least 50, at least 75, at least 100, at least 250, at least 500, at least $10^3$, at least $10^4$, at least $10^5$ or at least at least $10^6$ barcode molecules. Preferably, wherein the multimeric barcode molecule may be assembled using at least 5 barcode molecules. The multimeric barcode molecule may be assembled using at least 5, at least 10, at least 20, at least 25, at least 50, at least 75, at least 100, at least 250, at least 500, at least $10^3$, at least $10^4$, at least $10^5$ or at least at least $10^6$ unique or different barcode molecules. Preferably, wherein the multimeric barcode molecule may be assembled using at least 5 unique or different barcode molecules. Each barcode molecule comprises in the 5' to 3' direction a 5' region, a barcode region and a 3' region. Each barcode molecule is further defined herein. The multimeric barcode molecule may comprise the barcode regions of at least 5, at least 10, at least 20, at least 25, at least 50, at least 75, at least 100, at least 250, at least 500, at least $10^3$, at least $10^4$, at least $10^5$ or at least $10^6$ barcode molecules. Preferably, wherein the multimeric barcode molecule comprises the barcode regions of at least 5 barcode molecules. The multimeric barcode molecule may comprise the barcode regions of at least 5, at least 10, at least 20, at least 25, at least 50, at least 75, at least 100, at least 250, at least 500, at least $10^3$, at least $10^4$, at least $10^5$ or at least $10^6$ unique or different barcode molecules. Preferably, wherein the multimeric barcode molecule comprises the barcode regions of at least 5 unique or different barcode molecules.

The methods of assembling a double-stranded multimeric barcode molecule may be used to assemble a library of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different multimeric barcode molecules. Preferably, the methods of assembling a double-stranded multimeric barcode molecule are used to assemble a library of at least 5 different multimeric barcode molecules.

Double-stranded multimeric barcode molecules may be used to produce single-stranded multimeric barcode molecules for use as described herein. For example, this may be achieved by steps comprising: (i) denaturing double-stranded multimeric barcode molecules; and/or (ii) transcribing the DNA sequences of multimeric-barcode molecules to produce RNA sequences and then reverse transcribing the RNA sequences to produce single-stranded cDNA multimeric barcode molecules.

Any primer-extension step(s) involving forward and/or reverse splint primer(s), and/or forward and/or reverse termination primers, and/or forward and/or reverse amplification primers, as well as any overlap-extension step(s), as well as any PCR-amplification step, may be repeated two or more times in the process of synthesising multimeric barcoding molecules. These steps may improve the amount or molecular complexity of said multimeric barcoding molecules.

Methods of Synthesising a Multimeric Barcoding Reagent

The invention further provides a method of synthesising a multimeric barcoding reagent for labelling a target nucleic acid comprising: (a) contacting first and second barcode molecules with first and second extension primers, wherein each of the barcode molecules comprises a single-stranded nucleic acid comprising in the 5' to 3' direction an adapter region, a barcode region and a priming region; (b) annealing the first extension primer to the priming region of the first barcode molecule and annealing the second extension primer to the priming region of the second barcode molecule; and (c) synthesising a first barcoded extension product by extending the first extension primer and synthesising a second barcoded extension product by extending the second extension primer, wherein the first barcoded extension product comprises a sequence complementary to the barcode region of the first barcode molecule and the second barcoded extension product comprises a sequence complementary to the barcode region of the second barcode molecule, and wherein the first barcoded extension product does not comprise a sequence complementary to the adapter region of the first barcode molecule and the second barcoded extension product does not comprise a sequence complementary to the adapter region of the second barcode molecule; and wherein the first and second barcode molecules are linked together.

The method may further comprise the following steps before the step of synthesising the first and second barcoded extension products: (a) contacting first and second barcode molecules with first and second blocking primers; and (b) annealing the first blocking primer to the adapter region of the first barcode molecule and annealing the second blocking primer to the adapter region of the second barcode molecule; and wherein the method further comprises the step of dissociating the blocking primers from the barcode molecules after the step of synthesising the barcoded extension products.

In the method, the extension step, or a second extension step performed after the synthesis of an extension product, may be performed, in which one or more of the four canonical deoxyribonucleotides is excluded from the extension reaction, such that the second extension step terminates at a position before the adapter region sequence, wherein the position comprises a nucleotide complementary to the excluded deoxyribonucleotide. This extension step may be performed with a polymerase lacking 3' to 5' exonuclease activity.

The barcode molecules may be provided by a single-stranded multimeric barcode molecule as defined herein.

The barcode molecules may be synthesised by any of the methods defined herein. The barcode regions may uniquely identify each of the barcode molecules. The barcode molecules may be linked on a nucleic acid molecule. The barcode molecules may be linked together in a ligation reaction. The barcode molecules may be linked together by a further step comprising attaching the barcode molecules to a solid support. The first and second barcode molecules may be assembled as a double-stranded multimeric barcode molecule by any of the methods defined herein prior to step (a) defined above (i.e. contacting first and second barcode molecules with first and second extension primers). The double-stranded multimeric barcode molecule may be dissociated to produce single-stranded multimeric barcode molecules for use in step (a) defined above (i.e. contacting first and second barcode molecules with first and second extension primers).

The method may further comprise the steps of: (a) annealing an adapter region of a first adapter oligonucleotide to the adapter region of the first barcode molecule and annealing an adapter region of a second adapter oligonucleotide to the adapter region of the second barcode molecule, wherein the first adapter oligonucleotide further comprises a target region capable of annealing to a first sub-sequence of the target nucleic acid and the second adapter oligonucleotide further comprises a target region capable of annealing to a second sub-sequence of the target nucleic acid; and (b) ligating the 3' end of the first barcoded extension product to the 5' end of the first adapter oligonucleotide to produce a first barcoded oligonucleotide and ligating the 3' end of the second barcoded extension product to the 5' end of the second adapter oligonucleotide to produce a second barcoded oligonucleotide. Optionally, the annealing step (a) may be performed before the step of synthesising the first and second barcoded extension products and wherein the step of synthesising the first and second barcoded extension products is conducted in the presence of a ligase enzyme that performs the ligation step (b). The ligase may be a thermostable ligase. The extension and ligation reaction may proceed at over 37 degrees Celsius, over 45 degrees Celsius, or over 50 degrees Celsius.

The target regions may comprise different sequences. Each target region may comprise a sequence capable of annealing to only a single sub-sequence of a target nucleic acid within a sample of nucleic acids. Each target region may comprise one or more random, or one or more degenerate, sequences to enable the target region to anneal to more than one sub-sequence of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The adapter region of each adapter oligonucleotide may comprise a constant region. Optionally, all adapter regions of adapter oligonucleotides that anneal to a single multimeric barcoding reagent are substantially identical. The adapter region may comprise at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

For any of the methods involving adapter oligonucleotides, the 3' end of the adapter oligonucleotide may include a reversible terminator moiety or a reversible terminator nucleotide (for example, a 3'-O-blocked nucleotide), for example at the 3' terminal nucleotide of the target region. When used in an extension and/or extension and ligation reaction, the 3' ends of these adapter oligonucleotides may be prevented from priming any extension events. This may minimize mis-priming or other spurious extension events during the production of barcoded oligonucleotides. Prior to using the assembled multimeric barcoding reagents, the terminator moiety of the reversible terminator may be removed by chemical or other means, thus allowing the target region to be extended along a target nucleic acid template to which it is annealed.

Similarly, for any of the methods involving adapter oligonucleotides, one or more blocking oligonucleotides complementary to one or more sequences within the target region(s) may be employed during extension and/or extension and ligation reactions. The blocking oligonucleotides may comprise a terminator and/or other moiety on their 3' and/or 5' ends such that they are not able to be extended by polymerases. The blocking oligonucleotides may be designed such that they anneal to sequences fully or partially complementary to one or more target regions, and are annealed to said target regions prior to an extension and/or extension and ligation reaction. The use of blocking primers may prevent target regions from annealing to, and potentially mis-priming along, sequences within the solution for which such annealing is not desired (for example, sequence features within barcode molecules themselves). The blocking oligonucleotides may be designed to achieve particular annealing and/or melting temperatures. Prior to using the assembled multimeric barcoding reagents, the blocking oligonucleotide(s) may then be removed by, for example, heat-denaturation and then size-selective cleanup, or other means. The removal of the blocking oligonucleotide(s) may allow the target region to be extended along a target nucleic acid template to which it is annealed.

The method may comprise synthesising a multimeric barcoding reagent comprising at least 5, at least 10, at least 20, at least 25, at least 50, at least 75 or at least 100 barcode molecules, and wherein: (a) each barcode molecule is as defined herein; and (b) a barcoded extension product is synthesised from each barcode molecule according to any method defined herein; and, optionally, (c) an adapter oligonucleotide is ligated to each of the barcoded extension products to produce barcoded oligonucleotides according to any of the methods defined herein.

The invention further provides a method of synthesising a library of multimeric barcoding reagents, wherein the method comprises repeating the steps of any of the methods defined herein to synthesise two or more multimeric barcoding reagents. Optionally, the method comprises synthesising a library of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, at least $10^9$ or at least $10^{10}$ multimeric barcoding reagents as defined herein. Preferably, the library comprises at least 5 multimeric barcoding reagents as defined herein. Preferably, the barcode regions of each of the multimeric barcoding reagents may be different to the barcode regions of the other multimeric barcoding reagents.

FIG. 9 illustrates a method of synthesizing a multimeric barcoding reagent for labeling a target nucleic acid. In this method, first (D1, E1, and F1) and second (D2, E2, and F2) barcode molecules, which each include a nucleic acid sequence comprising a barcode region (E1 and E2), and which are linked by a connecting nucleic acid sequence (S), are denatured into single-stranded form. To these single-stranded barcode molecules, a first and second extension primer (A1 and A2) is annealed to the 3' region of the first and second barcode molecules (D1 and D2), and a first and second blocking primer (R1 and R2) is annealed to the 5' adapter region (F1 and F2) of the first and second barcode molecules. These blocking primers (R1 and R2) may be modified on the 3' end such that they cannot serve as a priming site for a polymerase.

A polymerase is then used to perform a primer extension reaction, in which the extension primers are extended to make a copy (B1 and B2) of the barcode region of the barcode molecules (E1 and E2). This primer extension reaction is performed such that the extension product terminates immediately adjacent to the blocking primer sequence, for example through use of a polymerase which lacks strand displacement or 5'-3' exonuclease activity. The blocking primers (R1 and R2) are then removed, for example through high-temperature denaturation.

This method thus creates a multimeric barcoding reagent containing a first and second ligation junction (J1 and J2) adjacent to a single-stranded adapter region (F1 and F2). This multimeric barcoding reagent may be used in the method illustrated in FIG. 12.

The method may further comprise the step of ligating the 3' end of the first and second barcoded oligonucleotides created by the primer-extension step (the 3' end of B1 and B2) to first (C1 and G1) and second (C2 and G2) adapter oligonucleotides, wherein each adapter oligonucleotide comprises an adapter region (C1 and C2) which is complementary to, and thus able to anneal to, the adapter region of a barcode molecule (F1 and F2). The adapter oligonucleotides may be synthesised to include a 5'-terminal phosphate group.

Each adapter oligonucleotide may also comprise a target region (G1 and G2), which may be used to anneal the barcoded oligonucleotides to target nucleic acids, and may separately or subsequently be used as primers for a primer-extension reaction or a polymerase chain reaction. The step of ligating the first and second barcoded oligonucleotides to the adapter oligonucleotides produces a multimeric barcoding reagent as illustrated in FIG. 1 that may be used in the methods illustrated in FIG. 2 and/or FIG. 3.

FIG. 10 shows a method of synthesizing multimeric barcoding reagents (as illustrated in FIG. 1) for labeling a target nucleic acid. In this method, first (D1, E1, and F1) and second (D2, E2, and F2) barcode molecules, which each include a nucleic acid sequence comprising a barcode region (E1 and E2), and which are linked by a connecting nucleic acid sequence (S), are denatured into single-stranded form. To these single-stranded barcode molecules, a first and second extension primer (A1 and A2) is annealed to the 3' region of the first and second barcode molecules (D1 and D2), and the adapter regions (C1 and C2) of first (C1 and G1) and second (C2 and G2) adapter oligonucleotides are annealed to the 5' adapter regions (F1 and F2) of the first and second barcode molecules. These adapter oligonucleotides may be synthesised to include a 5'-terminal phosphate group.

A polymerase is then used to perform a primer extension reaction, in which the extension primers are extended to make a copy (B1 and B2) of the barcode region of the barcode molecules (E1 and E2). This primer extension reaction is performed such that the extension product terminates immediately adjacent to the adapter region (C1 and C2) sequence, for example through use of a polymerase which lacks strand displacement or 5'-3' exonuclease activity.

A ligase enzyme is then used to ligate the 5' end of the adapter oligonucleotides to the adjacent 3' end of the corresponding extension product. In an alternative embodiment, a ligase enzyme may be included with the polymerase enzyme in one reaction which simultaneously effects both primer-extension and ligation of the resulting product to the adapter oligonucleotide. Through this method, the resulting barcoded oligonucleotides may subsequently be used as primers for a primer-extension reaction or a polymerase chain reaction, for example as in the method shown in FIG. 2 and/or FIG. 3.

Kits

The invention further provides kits comprising one or more of the components defined herein. The invention also provides kits specifically adapted for performing any of the methods defined herein.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising, optionally in the 5' to 3' direction, an adapter region and a barcode region, and (ii) first and second barcode oligonucleotides, wherein the first barcoded oligonucleotide comprises a barcode region annealed to the barcode region of the first barcode molecule, and wherein the second barcode oligonucleotide comprises a barcode region annealed to the barcode region of the second barcode molecule; and (b) first and second adapter oligonucleotides, wherein the first adapter oligonucleotide comprises, optionally in the 5' to 3' direction, an adaptor region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adaptor region capable of annealing to the adapter region of the second barcode molecule and a target region capable of annealing or ligating to a second sub-sequence of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising an adapter region and a barcode region, and (ii) first and second barcode oligonucleotides, wherein the first barcoded oligonucleotide comprises a barcode region annealed to the barcode region of the first barcode molecule, and wherein the second barcode oligonucleotide comprises a barcode region annealed to the barcode region of the second barcode molecule; and (b) first and second adapter oligonucleotides, wherein the first adapter oligonucleotide comprises an adaptor region capable of annealing to the adapter region of the first barcode molecule and a target region capable of ligating to a first sub-sequence of the target nucleic acid, and wherein the second adapter oligonucleotide comprises an adaptor region capable of annealing to the adapter region of the second barcode molecule and a target region capable of ligating to a second sub-sequence of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising in the 5' to 3' direction an adapter region and a barcode region, and (ii) first and second barcode oligonucleotides, wherein the first barcode oligonucleotide comprises a barcode region annealed to the barcode region of the first barcode molecule, and wherein the second barcode oligonucleotide comprises a barcode region annealed to the barcode region of the second barcode molecule; and (b) first and second adapter oligonucleotides, wherein the first adapter oligonucleotide comprises in the 5' to 3' direction an adaptor region capable of annealing to the adapter region of the first barcode molecule and a target region capable of annealing to a first sub-sequence of the target nucleic acid, and wherein the second adapter oligonucleotide comprises in the 5' to 3' direction an adaptor region capable of annealing to the adapter region of the second barcode molecule and a target region capable of annealing to a second sub-sequence of the target nucleic acid.

The adapter oligonucleotides may comprise a linker region between the adapter region and the target region. The linker region may comprise one or more contiguous nucleotides that are not annealed to the first and second barcode molecules (i.e. the multimeric barcode molecule) and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the kits described herein.

Each of the components of the kit may take any of the forms defined herein. Preferably, the barcode regions uniquely identify each of the barcode molecules, the target regions comprise different sequences and/or the adapter regions of the adapter oligonucleotides comprise an identical constant region. Preferably, the barcode molecules are linked on a nucleic acid molecule and/or the barcode molecules are linked by attachment to a solid support.

The target regions of the adapter oligonucleotides (which are not annealed to the multimeric barcode molecule(s)) may be non-complementary to the multimeric barcode molecule(s).

Preferably, the barcode molecules comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcode molecules may comprise one or more degenerate nucleotides or sequences. The barcode molecules may not comprise any degenerate nucleotides or sequences.

Preferably the barcoded oligonucleotides comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcoded oligonucleotides may comprise one or more degenerate nucleotides or sequences. The barcoded oligonucleotides may not comprise any degenerate nucleotides or sequences Preferably, the barcode region of the first barcode oligonucleotide comprises a sequence that is complementary and annealed to the barcode region of the first barcode molecule and the barcode region of the second barcoded oligonucleotide comprises a sequence that is complementary and annealed to the barcode region of the second barcode molecule. The complementary sequence of each barcode oligonucleotide may be at least 5, at least 10, at least 15, at least 20, at least 25, at least 50 or at least 100 contiguous nucleotides.

The multimeric barcoding reagent(s) and adapter oligonucleotides may be provided in the kit as physically separated components.

The kit may comprise: (a) a multimeric barcoding reagent comprising at least 5, at least 10, at least 20, at least 25, at least 50, at least 75 or at least 100 barcode molecules linked together, wherein each barcode molecule is as defined herein; and (b) an adaptor oligonucleotide capable of annealing to each barcode molecule, wherein each adaptor oligonucleotide is as defined herein.

The kit may comprise a library of two or more multimeric barcoding reagents, wherein each multimeric barcoding reagent is as defined herein, and adaptor oligonucleotides for each of the multimeric barcoding reagents, wherein each adaptor oligonucleotide is as defined herein, wherein the barcode regions of the first multimeric barcoding reagent are different to the barcode regions of the second multimeric barcoding reagent.

The invention provides a kit for labelling a target nucleic acid for sequencing, wherein the kit comprises: (a) a library of multimeric barcoding reagents comprising at least 10 multimeric barcoding reagents, wherein each multimeric barcoding reagent comprises: (i) first and second barcode molecules comprised within a (single) nucleic acid molecule, wherein each of the barcode molecules comprises a nucleic acid sequence comprising, optionally in the 5' to 3' direction, an adapter region and a barcode region, and (ii) first and second barcode oligonucleotides, wherein the first barcode oligonucleotide comprises a barcode region complementary and annealed to the barcode region of the first barcode molecule, and wherein the second barcode oligonucleotide comprises a barcode region complementary and annealed to the barcode region of the second barcode molecule; and (b) first and second adapter oligonucleotides for each of the multimeric barcoding reagents, wherein the first adapter oligonucleotide comprises, optionally in the 5' to 3' direction, an adaptor region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adaptor region capable of annealing to the adapter region of the second barcode molecule and a target region capable of annealing or ligating to a second sub-sequence of the target nucleic acid.

The barcode regions of the first and second barcode molecules of each multimeric barcoding reagent are different to the barcode regions of at least 9 other multimeric barcoding reagents in the library.

The kit may comprise a library of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, at least $10^9$ or at least $10^{10}$ multimeric barcoding reagents. Preferably, the kit comprises a library of at least 5 multimeric barcoding reagents. Each multimeric barcoding reagent may take the form of any of the multimeric barcoding reagents defined herein. The kit may further comprises adaptor oligonucleotides for each of the multimeric barcoding reagents, wherein each adaptor oligonucleotide may take the form of any of the adapter oligonucleotides defined herein. Preferably, the barcode regions of each of the multimeric barcoding reagents are different to the barcode regions of the other multimeric barcoding reagents in the kit.

The barcode regions of each multimeric barcoding reagent may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. Preferably, the barcode regions of each multimeric barcoding reagent are different to the barcode regions of at least 999 (i.e. $10^3$-1) other multimeric barcoding reagents in the library.

FIG. 11 shows a kit comprising a multimeric barcoding reagent and adapter oligonucleotides for labelling a target nucleic acid. In more detail, the kit comprises first (D1, E1, and F1) and second (D2, E2, and F2) barcode molecules, with each incorporating a barcode region (E1 and E2) and also a 5' adapter region (F1 and F2). These first and second barcode molecules are linked together, in this embodiment by a connecting nucleic acid sequence (S).

The kit further comprises first (A1 and B1) and second (A2 and B2) barcoded oligonucleotides, which each comprise a barcode region (B1 and B2), as well as 5' regions (A1 and A2). The 5' region of each barcoded oligonucleotide is complementary to, and thus may be annealed to, the 3' regions of the barcode molecules (D1 and D2). The barcode regions (B1 and B2) are complementary to, and thus may be annealed to, the barcode regions (E1 and E2) of the barcode molecules.

The kit further comprises first (C1 and G1) and second (C2 and G2) adapter oligonucleotides, wherein each adapter oligonucleotide comprises an adapter region (C1 and C2) that is complementary to, and thus able to anneal to, the 5' adapter region of a barcode molecule (F1 and F2). These adapter oligonucleotides may be synthesised to include a 5'-terminal phosphate group. Each adapter oligonucleotide also comprises a target region (G1 and G2), which may be used to anneal the barcoded oligonucleotides to target nucleic acids, and then may be used as primers for a primer-extension reaction or a polymerase chain reaction.

The invention further provides a kit for labelling a target nucleic acid for sequencing, wherein the kit comprises: (a) a library of multimeric barcode molecules comprising at least 10 multimeric barcode molecules, each multimeric barcode molecule comprising first and second barcode molecules comprised within a nucleic acid molecule, wherein each of the barcode molecules comprises a nucleic acid sequence comprising, optionally in the 5' to 3' direction, an adapter region and a barcode region, and wherein the barcode regions of the first and second barcode molecules of each multimeric barcode molecule are different to the barcode regions of at least 9 other multimeric barcode molecules in the library; and (b) first and second adapter oligonucleotides for each of the multimeric barcode molecules, wherein the first adapter oligonucleotide comprises, optionally in the 5' to 3' direction, an adaptor region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adaptor region capable of annealing to the adapter region of the second barcode molecule and a target region capable of annealing or ligating to a second sub-sequence of the target nucleic acid.

The invention further provides a kit for labelling a target nucleic acid for sequencing, wherein the kit comprises: (a) a library of multimeric barcode molecules comprising at least 10 multimeric barcode molecules, each multimeric barcode molecule comprising first and second barcode molecules comprised within a (single) nucleic acid molecule, wherein each of the barcode molecules comprises a nucleic acid sequence comprising, optionally in the 5' to 3' direction, an adapter region, a barcode region, and a priming region, and wherein the barcode regions of the first and second barcode molecules of each multimeric barcode molecule are different to the barcode regions of at least 9 other multimeric barcode molecules in the library; (b) first and second extension primers for each of the multimeric barcode molecules, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for each of the multimeric barcode molecules, wherein the first adapter oligonucleotide comprises, optionally in the 5' to 3' direction, an adaptor region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adaptor region capable of annealing to the adapter region of the second barcode molecule and a target region capable of annealing or ligating to a second sub-sequence of the target nucleic acid.

Each multimeric barcode molecule in the library may be a single-stranded nucleic acid molecule (e.g. single-stranded DNA) comprising two or more barcode molecules.

The first and second extension primers are capable of being extended using the barcode regions of the first and second barcode molecules as templates to produce first and second barcode oligonucleotides, wherein the first barcode oligonucleotide comprises a sequence complementary to the barcode region of the first barcode molecule and the second barcode oligonucleotide comprises a sequence complementary to the barcode region of the second barcode molecule.

Each of the components of the kit may take any of the forms defined herein.

The target regions of the adapter oligonucleotides (which are not annealed to the multimeric barcode molecule(s)) may be non-complementary to the multimeric barcode molecule(s).

The adapter oligonucleotides may comprise a linker region between the adapter region and the target region. The linker region may comprise one or more contiguous nucleotides that are not annealed to the multimeric barcode molecule and are non-complementary to the subsequences of the target nucleic acid. The linker may comprise 1 to 100, 5 to 75, 10 to 50, 15 to 30, or 20 to 25 non-complementary nucleotides. Preferably, the linker comprises 15 to 30 non-complementary nucleotides. The use of such a linker region enhances the efficiency of the barcoding reactions performed using the kits described herein.

The first and second extension primers may be identical in sequence. Alternatively, the first and second extension primers may be different in sequence.

Each multimeric barcode molecule may comprise at least 5, at least 10, at least 20, at least 25, at least 50, at least 75 or at least 100 barcode molecules linked together, wherein each barcode molecule is as defined herein; and wherein the kit comprises an adaptor oligonucleotide capable of annealing to each barcode molecule, wherein each adaptor oligonucleotide is as defined herein.

The kit may comprise a library of at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcode molecules, wherein each multimeric barcode molecule is as defined herein, and adaptor oligonucleotides for each of the multimeric barcode molecules, wherein each adaptor oligonucleotide is as defined herein.

The barcode regions of each of the multimeric barcode molecules may be different to the barcode regions of the other multimeric barcode molecules in the library.

The barcode regions of each multimeric barcode molecule may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcode molecules in the library. Preferably, the barcode regions of each multimeric barcode molecule are different to the barcode regions of at least 999 (i.e. $10^3$-1) other multimeric barcode molecules in the library.

Further Methods of Preparing a Nucleic Acid Sample for Sequencing

The invention may be used to prepare a range of different nucleic acid samples for sequencing. The target nucleic acids may be DNA molecules (e.g. genomic DNA molecules) or RNA molecules (e.g. mRNA molecules). The target nucleic acids may be from any sample. For example, an individual cell (or cells), a tissue, a bodily fluid (e.g. blood, plasma and/or serum), a biopsy or a formalin-fixed paraffin-embedded (FFPE) sample.

The methods provided below may be performed with any of the kits defined herein.

The invention further provides a method of preparing a nucleic acid sample for sequencing, wherein the method comprises the steps of: (a) contacting the nucleic acid sample with a first and second adapter oligonucleotide as defined herein; (b) annealing the target region of the first adapter oligonucleotide to a first sub-sequence of a target nucleic acid, and annealing the target region of the second adapter oligonucleotide to a second sub-sequence of the target oligonucleotide; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) ligating the 3' end of the first barcode oligonucleotide to the 5' end of the first adapter oligonucleotide to produce a first barcoded oligonucleotide and ligating the free 3' end of the second barcode oligonucleotide to the 5' end of the second adapter oligonucleotide to produce a second barcoded oligonucleotide. In the method the first and second barcoded oligonucleotides are extended to produce first and second different barcoded target nucleic acid molecules each of which comprises at least one nucleotide synthesised from the target nucleic acid as a template.

Each barcoded target nucleic acid molecule may comprise at least 5, at least 10, at least 25, at least 50, at least 100, at least 250, at least 500, at least 1000, at least 2000, at least 5000, or at least 10,000 nucleotides synthesised from the target nucleic acid as template. Preferably, each barcoded target nucleic acid molecule comprises at least 5 nucleotides synthesised from the target nucleic acid as template.

The method may be performed using a library of multimeric barcoding reagents as defined herein and an adaptor oligonucleotide as defined herein for each of the multimeric barcoding reagents. Preferably, the barcoded oligonucleotides of the first multimeric barcoding reagent anneal to sub-sequences of a first target nucleic acid and first and second different barcoded target nucleic acid molecules are produced, wherein each barcoded target nucleic acid molecule comprises at least one nucleotide synthesised from the first target nucleic acid as a template; and the barcoded oligonucleotides of the second multimeric barcoding reagent anneal to sub-sequences of a second target nucleic acid and first and second different barcoded target nucleic acid molecules are produced, wherein each barcoded target nucleic acid molecule comprises at least one nucleotide synthesised from the second target nucleic acid as a template.

The target nucleic acid may be an intact nucleic acid molecule, co-localised fragments of a nucleic acid molecule, or nucleic acid molecules from a single cell. Preferably, the target nucleic acid is a single intact nucleic acid molecule, two or more co-localised fragments of a single nucleic acid molecule, or two or more nucleic acid molecules from a single cell.

The step of extending the barcoded oligonucleotides may be performed before step (c), before step (d) and/or before step (e), and the first and second barcoded oligonucleotides may remain annealed to the first and second barcode molecules until after step (e).

Alternatively, the step of extending the barcoded oligonucleotides may be performed after step (e).

The method may comprise producing at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different barcoded target nucleic acid molecules. Preferably, the method comprises producing at least 5 different barcoded target nucleic acid molecules.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

Prior to contacting the nucleic acid sample with a library of multimeric barcoding reagents as defined herein, a coupling sequence may be added to the 5' end or 3' end of two or more target nucleic acids of the nucleic acid sample (e.g. a FFPE DNA sample). In this method, the target regions may comprise a sequence that is complementary to the coupling sequence. The coupling sequence may comprise a homopolymeric 3' tail (e.g. a poly(A) tail). The coupling sequence may be added by a terminal transferase enzyme. In the method in which the coupling sequence comprises a poly(A) tail, the target regions may comprise a poly(T) sequence.

The method may comprise preparing two or more independent nucleic acid samples for sequencing, wherein each nucleic acid sample is prepared using a different library of multimeric barcoding reagents (or a different library of multimeric barcode molecules), and wherein the barcode regions of each library of multimeric barcoding reagents (or multimeric barcode molecules) comprise a sequence that is different to the barcode regions of the other libraries of multimeric barcoding reagents (or multimeric barcode molecules). Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcoding reagents (or multimeric barcode molecules) that was used in its preparation and thereby to identify the nucleic acid sample from which it was prepared.

The barcoded oligonucleotides may be isolated from the nucleic acid sample after annealing to the sub-sequences of the target nucleic acid and before the barcoded target nucleic acid molecules are produced. Optionally, the barcoded oligonucleotides are isolated by capture on a solid support through a streptavidin-biotin interaction.

The barcoded target nucleic acid molecules may be isolated from the nucleic acid sample. Optionally, the barcoded target nucleic acid molecules are isolated by capture on a solid support through a streptavidin-biotin interaction.

FIG. 12 shows a method of preparing a nucleic acid sample for sequencing using a multimeric barcoding reagent. In the method first (C1 and G1) and second (C2 and G2) adapter oligonucleotides are annealed to a target nucleic acid in the nucleic acid sample, and then used in a primer extension reaction. Each adapter oligonucleotide is comprised of an adapter region (C1 and C2) that is complementary to, and thus able to anneal to, the 5' adapter region of a barcode molecule (F1 and F2). Each adapter oligonucleotide is also comprised of a target region (G1 and G2), which may be used to anneal the barcoded oligonucleotides to target nucleic acids, and then may be used as primers for a primer-extension reaction or a polymerase chain reaction. These adapter oligonucleotides may be synthesised to include a 5'-terminal phosphate group.

The adapter oligonucleotides, each of which has been extended to include sequence from the target nucleic acid, are then contacted with a multimeric barcoding reagent which comprises a first (D1, E1, and F1) and second (D2, E2, and F2) barcode molecule, as well as first (A1 and B1) and second (A2 and B2) barcoded oligonucleotides, which each comprise a barcode region (B1 and B2), as well as 5' regions (A1 and A2). The first and second barcode molecules each comprise a barcode region (E1 and E2), an adapter region (F1 and F2), and a 3' region (D1 and D2), and are linked together, in this embodiment by a connecting nucleic acid sequence (S).

After contacting the primer-extended nucleic acid sample with a multimeric barcoding reagent, the 5' adapter regions (C1 and C2) of each adapter oligonucleotides are able to anneal to a 'ligation junction' adjacent to the 3' end of each barcoded oligonucleotide (J1 and J2). The 5' end of the extended adapter oligonucleotides are then ligated to the 3' end of the barcoded oligonucleotides within the multimeric barcoding reagent, creating a ligated base pair (K1 and K2) where the ligation junction was formerly located. The solution may subsequently be processed further or amplified, and used in a sequencing reaction.

This method, like the methods illustrated in FIGS. 2 and 3, creates barcoded target nucleic acid molecules, wherein two or more sub-sequences from the nucleic acid sample are labeled by a barcoded oligonucleotide. In this method a multimeric barcoding reagent does not need to be present for the step of annealing target regions to sub-sequences of the target nucleic acid, or the step of extending the annealed target regions using a polymerase. This feature may hold advantages in certain applications, for example wherein a large number of target sequences are of interest, and the target regions are able to hybridise more rapidly to target nucleic acids when they are not constrained molecularly by a multimeric barcoding reagent.

The invention further provides a method of preparing a nucleic acid sample for sequencing, wherein the method comprises the steps of: (a) contacting the nucleic acid sample with first and second adapter oligonucleotides as defined herein; (b) annealing the target region of the first adapter oligonucleotide to a first sub-sequence of a target nucleic acid, and annealing the target region of the second adapter oligonucleotide to a second sub-sequence of the target oligonucleotide; (c) contacting the nucleic acid sample with a library of multimeric barcode molecules as defined herein and first and second extension primers as defined herein; (d) annealing the adapter region of the first adapter oligonucleotide to the adapter region of the first barcode molecule, and annealing the adapter region of the second adapter oligonucleotide to the adapter region of the second barcode molecule; (e) extending the first extension primer using the barcode region of the first barcode molecule as a template to produce a first barcode oligonucleotide, and extending the second extension primer using the barcode region of the second barcode molecule as a template to produce a second barcode oligonucleotide, wherein the first barcode oligonucleotide comprises a sequence complementary to the barcode region of the first barcode molecule and the second barcode oligonucleotide comprises a sequence complementary to the barcode region of the second barcode molecule; and (f) ligating the 3' end of the first barcode oligonucleotide to the 5' end of the first adapter oligonucleotide to produce a first barcoded oligonucleotide and ligating the 3' end of the second barcode oligonucleotide to the 5' end of the second adapter oligonucleotide to produce a second barcoded oligonucleotide; and wherein the first and second adapter oligonucleotides, or the first and second barcoded oligonucleotides, are extended to produce first and second different barcoded target nucleic acid molecules each of which comprises at least one nucleotide synthesised from the target nucleic acid as a template.

Each barcoded target nucleic acid molecule may comprise at least 5, at least 10, at least 25, at least 50, at least 100, at least 250, at least 500, at least 1000, at least 2000, at least 5000, or at least 10,000 nucleotides synthesised from the target nucleic acid as template. Preferably, each barcoded target nucleic acid molecule comprises at least 5 nucleotides synthesised from the target nucleic acid as template.

The extension primers may be annealed to the multimeric barcode molecules prior to step (c). Alternatively, the nucleic acid sample may be contacted with a library of multimeric barcode molecules as defined herein and separate extension primers as defined herein. The extension primers may then be annealed to the multimeric barcode molecules in the nucleic acid sample. The extension primers may be annealed to the multimeric barcode molecules during step (d).

Preferably, the adapter oligonucleotides or the barcoded oligonucleotides of the first multimeric barcode molecule may anneal to sub-sequences of a first target nucleic acid and first and second different barcoded target nucleic acid molecules may be produced, wherein each barcoded target nucleic acid molecule comprises at least one nucleotide synthesised from the first target nucleic acid as a template; and the adapter oligonucleotides or the barcoded oligonucleotides of the second multimeric barcode molecule may anneal to sub-sequences of a second target nucleic acid and first and second different barcoded target nucleic acid molecules may be produced, wherein each barcoded target nucleic acid molecule comprises at least one nucleotide synthesised from the second target nucleic acid as a template.

In the method, the step of extending the adapter oligonucleotides may be performed before step (c), before step (d), before step (e), and/or before step (f), and wherein the first and second adapter oligonucleotides oligonucleotides remain annealed to the first and second barcode molecules until after step (f). Alternatively, the barcoded oligonucleotides (produced by step (f)) may be extended.

The barcoded oligonucleotides may be isolated from the nucleic acid sample after annealing to the sub-sequences of the target nucleic acid and before the barcoded target nucleic acid molecules are produced.

The target nucleic acid may be an intact nucleic acid molecule or co-localised fragments of a nucleic acid molecule.

The method may comprise producing at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different barcoded target nucleic acid molecules.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

Prior to contacting the nucleic acid sample with a library of multimeric barcode molecules and adaptor oligonucleotides as defined herein, a coupling sequence may be added to the 5' end or 3' end of two or more target nucleic acids of the nucleic acid sample (e.g. a FFPE DNA sample). In this method, the target regions may comprise a sequence that is complementary to the coupling sequence. The coupling sequence may comprise a homopolymeric 3' tail (e.g. a poly(A) tail). The coupling sequence may be added by a terminal transferase enzyme. In the method in which the coupling sequence comprises a poly(A) tail, the target regions may comprise a poly(T) sequence.

The method may comprise preparing two or more independent nucleic acid samples for sequencing, wherein each nucleic acid sample is prepared using a different library of multimeric barcode molecules, and wherein the barcode regions of each library of multimeric barcode molecules comprise a sequence that is different to the barcode regions of the other libraries of multimeric barcode molecules. Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcode molecules that was used in its preparation and thereby to identify the nucleic acid sample from which it was prepared.

The barcoded oligonucleotides may be isolated from the nucleic acid sample after annealing to the sub-sequences of the target nucleic acid and before the barcoded target nucleic acid molecules are produced. Optionally, the barcoded oligonucleotides are isolated by capture on a solid support through a streptavidin-biotin interaction.

The barcoded target nucleic acid molecules may be isolated from the nucleic acid sample. Optionally, the barcoded target nucleic acid molecules are isolated by capture on a solid support through a streptavidin-biotin interaction.

The invention further provides a method of preparing a nucleic acid sample for sequencing, wherein the method comprises the steps of: (a) contacting the nucleic acid sample with first and second adapter oligonucleotides, wherein each adapter oligonucleotide comprises in the 5' to 3' direction a target region and an adapter region, and first and second target primers; (b) annealing the target region of the first adapter oligonucleotide to a first sub-sequence of a target nucleic acid, and annealing the target region of the second adapter oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; (e) ligating the 3' end of the first extended target primer to the 5' end of the first adapter oligonucleotide, and ligating the 3' end of the second extended target primer to the 5' end of the second adapter oligonucleotide; (f) contacting the nucleic acid sample with a library of multimeric barcode molecules as defined herein; (g) annealing the adapter region of the first adapter oligonucleotide to the adapter region of the first barcode molecule, and annealing the adapter region of the second adapter oligonucleotide to the adapter region of the second barcode molecule; and (h) extending the first adapter oligonucleotide using the barcode region of the first barcode molecule as a template to produce a first barcoded oligonucleotide, and extending the second adapter oligonucleotide using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule.

In the method, steps (b) and (c) may be performed at the same time.

In the method, steps (f)-(h) may be performed before steps (d) and (e). In this method, first and second different barcoded target nucleic acid molecules, each of which comprises at least one nucleotide synthesised from the target nucleic acid as a template, are produced by the completion of step (c).

In the method, steps (f)-(h) may be performed after steps (d) and (e). In this method, first and second different barcoded target nucleic acid molecules, each of which comprises at least one nucleotide synthesised from the target nucleic acid as a template, are produced by the completion of step (h).

Each barcoded target nucleic acid molecule may comprise at least 5, at least 10, at least 25, at least 50, at least 100, at least 250, at least 500, at least 1000, at least 2000, at least 5000, or at least 10,000 nucleotides synthesised from the target nucleic acid as template. Preferably, each barcoded target nucleic acid molecule comprises at least 5 nucleotides synthesised from the target nucleic acid as template.

FIG. 13 illustrates one way in which this method may be performed. In this method, the target nucleic acid is genomic DNA. It will be appreciated that the target nucleic acid may be another type of nucleic acid e.g. an RNA molecule such as an mRNA molecule.

In any method of preparing a nucleic acid sample for sequencing from a kit, the nucleic acid molecules within the nucleic acid sample, and/or the multimeric barcoding reagents, and/or multimeric barcode molecules (and/or other reagents included in the kits), may be present at particular concentrations within the solution volume, for example at concentrations of at least 100 nanomolar, at least 10 nanomolar, at least 1 nanomolar, at least 100 picomolar, at least 10 picomolar, or at least 1 picomolar. The concentrations may be 1 picomolar to 100 nanomolar, 10 picomolar to 10 nanomolar, or 100 picomolar to 1 nanomolar. Alternative higher or lower concentrations may also be used.

Methods of Sequencing and/or Processing Sequencing Data

The invention further provides a method of sequencing a sample, wherein the sample has been prepared by any one of the methods of preparing a nucleic acid sample for sequencing as defined herein. The method of sequencing the sample comprises the steps of: isolating the barcoded target nucleic acid molecules, and producing a sequence read from each barcoded target nucleic acid molecule that comprises the barcode region, the target region and at least one additional nucleotide from the target nucleic acid. Each sequence read may comprise at least 5, at least 10, at least 25, at least 50, at least 100, at least 250, at least 500, at least 1000, at least 2000, at least 5000, or at least 10,000 nucleotides from the target nucleic acid. Preferably, each sequence read comprises at least 5 nucleotides from the target nucleic acid.

Sequencing may be performed by any method known in the art. For example, by chain-termination or Sanger sequencing. Preferably, sequencing is performed by a next-generation sequencing method such as sequencing by synthesis, sequencing by synthesis using reversible terminators (e.g. Illumina sequencing), pyrosequencing (e.g. 454 sequencing), sequencing by ligation (e.g. SOLiD sequencing) or single-molecule sequencing (e.g. Single Molecule, Real-Time (SMRT) sequencing, Pacific Biosciences).

The invention further provides a method for processing sequencing data obtained by any of the methods defined herein. The method for processing sequence data comprises the steps of: (a) identifying for each sequence read the sequence of the barcode region and the sequence from the target nucleic acid; and (b) using the information from step (a) to determine a group of sequences from the target nucleic acid that were labelled with barcode regions from the same multimeric barcoding reagent.

The method may further comprise the step of determining a sequence of a target nucleic acid by analysing the group of sequences to identify contiguous sequences, wherein the sequence of the target nucleic acid comprises nucleotides from at least two sequence reads.

The target nucleic acid may be an intact nucleic acid molecule, co-localised fragments of a nucleic acid molecule, or nucleic acid molecules from a single cell. Preferably, the target nucleic acid is a single intact nucleic acid molecule, two or more co-localised fragments of a single nucleic acid molecule, or two or more nucleic acid molecules from a single cell.

The invention further provides an algorithm for processing (or analysing) sequencing data obtained by any of the methods defined herein. The algorithm may be configured to perform any of the methods for processing sequencing data defined herein. The algorithm may be used to detect the sequence of a barcode region within each sequence read, and also to detect the sequence within a sequence read that is derived from a target nucleic acid, and to separate these into two associated data sets.

The invention further provides a method of generating a synthetic long read from a target nucleic acid comprising the steps of: (a) preparing a nucleic acid sample for sequencing according to any of the methods defined herein; (b) sequencing the sample, optionally wherein the sample is sequenced by any of the methods defined herein; and (c) processing the sequence data obtained by step (b), optionally wherein the sequence data is processed according to any of the methods defined herein; wherein step (c) generates a synthetic long read comprising at least one nucleotide from each of the at least two sequence reads.

The method may enable the phasing of a target sequence of a target nucleic acid molecule i.e. it may enable the determination of which copy of a chromosome (i.e. paternal or maternal) the sequence is located. The target sequence may comprise a specific target mutation, translocation, deletion or amplification and the method may be used to assign the mutation, translocation, deletion or amplification to a specific chromosome. The phasing two or more target sequences may also enable the detection of aneuploidy.

The synthetic long read may comprise at least 50, at least 100, at least 250, at least 500, at least 750, at least 1000, at least 2000, at least $10^4$, at least $10^5$, at least $10^6$, at least $10^7$ or at least $10^8$ nucleotides. Preferably, the synthetic long read comprises at least 50 nucleotides.

The invention further provides a method of sequencing two or more co-localised target nucleic acids comprising the steps of: (a) preparing a nucleic acid sample for sequencing according to any of the methods defined herein; (b) sequencing the sample, optionally wherein the sample is sequenced by any of the methods defined herein; and (c) processing the sequence data obtained by step (b), optionally wherein the sequence data is processed according to any of the methods defined herein; wherein step (c) identifies at least two sequence reads comprising nucleotides from at least two target nucleic acids co-localised in the sample.

The invention further provides a method of sequencing target nucleic acids from an individual cell comprising the steps of: (a) preparing a nucleic acid sample for sequencing according any of the methods defined herein, wherein the multimeric barcoding reagent(s), or multimeric barcode molecule(s), and/or adaptor oligonucleotides are introduced into the cell; (b) sequencing the sample, optionally wherein the sample is sequenced by any of the methods defined herein; and (c) processing the sequence data obtained by step (b), optionally wherein the sequence data is processed according to any of the methods defined herein; wherein step (c) identifies at least two sequence reads comprising nucleotides from at least two target nucleic acids from the cell.

The multimeric barcoding reagent(s) and/or adaptor oligonucleotides may be introduced into the cell by chemical complexation with a lipid transfection reagent and then transfection into the cell.

The multimeric barcoding reagent(s) and/or adaptor oligonucleotides may be introduced into the cell through the steps of: (a) permeabilising the cell membrane by contacting it with a chemical surfactant; and then (b) contacting the cell with the multimeric barcoding reagent(s) and/or adaptor oligonucleotides. The chemical surfactant may be a nonionic surfactant. The chemical surfactant may be Triton X-100 ($C_{14}H_{22}O(C_2H_4O)_n$ (n=9-10)). The chemical surfactant may be in solution at a concentration of less than 200 micromolar, or less than 500 micromolar, or less than 1 milimolar.

In the method, following the step of introducing the multimeric barcoding reagent(s) and/or adaptor oligonucleotides into the cell, the cell may be incubated for a period of time to allow the target regions of the multimeric barcoding reagent(s) or adapter oligonucleotide(s) to anneal to sub-sequences of the target nucleic acids within the cell. The incubation period may be at least 1 minute, or at least 5 minutes, or at least 15 minutes, or at least 30 minutes, or at least 60 minutes. Preferably, the incubation period is at least 1 minute. The incubation may take place within a solution containing a nucleic acid denaturant e.g. dimethyl sulfoxide (DMSO) or betaine. The incubation may take place at a temperature of at least 20 degrees Celsius, at least 37 degrees Celsius, at least 45 degrees Celsius, or at least 50 degrees Celsius. Preferably, the incubation takes place at a temperature of at least 20 degrees Celsius.

In methods involving the use of multimeric barcoding reagents, the incubation step may substantially dissociate the barcoded oligonucleotides from the barcode molecules (or multimeric barcode molecule). This may enable the barcoded oligonucleotides to diffuse more readily throughout the cell improving the efficiency with which the target regions of the barcoded oligonucleotides are able to anneal to sub-sequences of the target nucleic acids.

In the method, following introduction of the multimeric barcoding reagent(s) and/or adaptor oligonucleotides into the cell, and optionally following the incubation step, the cell may be contacted by a solution of oligonucleotides complementary to the target regions of the multimeric barcoding reagents.

In the method, following introduction of the multimeric barcoding reagent(s) and/or adaptor oligonucleotides into the cell, and optionally following the incubation step, the cell may be isolated from a reaction mixture e.g. by centrifugation.

In the method, following introduction of the multimeric barcoding reagent(s) and/or adaptor oligonucleotides into the cell, and optionally following the incubation step, the barcoded oligonucleotides and/or barcoded target nucleic acid molecules and/or multimeric barcoding reagent(s) may be isolated from the cell.

The multimeric barcoding reagents, barcoded oligonucleotides and/or adaptor oligonucleotides may comprise one or more biotin moieties.

In the method, following introduction of the multimeric barcoding reagent(s) and/or adaptor oligonucleotides into the cell, and optionally following the incubation step, the barcoded oligonucleotides and/or barcoded target nucleic acid molecules and/or multimeric barcoding reagent(s) may be isolated by a process of: (a) optionally dissolving the cell membranes e.g. using a chemical surfactant or by incubation at high temperature; (b) contacting the resulting mixture with a solid support, optionally wherein the solid support comprises streptavidin moieties; and (c) capturing the barcoded oligonucleotides and/or barcoded target nucleic acid molecules and/or multimeric barcoding reagent(s) on the solid support, optionally through streptavidin-biotin interaction. The solid support may be one or more magnetic beads, optionally wherein the one or more magnetic beads comprise streptavidin molecules on their surface. The magnetic bead(s) may be isolated from a reaction mixture with a magnet.

The target nucleic acids may be DNA molecules (e.g. genomic DNA molecules) or RNA molecules (e.g. mRNA molecules).

Preferably, each barcoded target nucleic acid molecule is produced after isolation of the barcoded oligonucleotide annealed to a target mRNA molecule by extending the barcoded oligonucleotide using a reverse transcriptase and the target mRNA molecule as the template.

The mRNA molecules may be mRNA molecules corresponding to alpha and/or beta chains of a T-cell receptor sequence, optionally wherein the sequences of alpha and beta chains paired within an individual cell are determined.

The mRNA molecules may be mRNA molecules corresponding to light and/or heavy chains of an immunoglobulin sequence, optionally wherein the sequences of light and heavy chains paired within an individual cell are determined.

The method may be used to sequence target nucleic acids in at least 10, at least 100, or at least $10^3$, at least $10^4$, at least $10^5$, at least $10^6$, at least $10^7$, at least $10^8$ or at least $10^9$ cells. Preferably, the method may be used to sequence target nucleic acids in at least 10 cells. Preferably the cells are T-cells and/or B-cells.

Uses of a Multimeric Barcoding Reagent, Library or Kit

The invention further provides the use of a multimeric barcoding reagent as defined herein, a library of multimeric barcoding reagents as defined herein, or a kit as defined herein, to produce two or more sequence reads from a target nucleic acid, wherein two or more sequence reads can be identified as derived from the same target nucleic acid and combined to produce a synthetic long read.

The invention further provides the use of a multimeric barcoding reagent as defined herein, a library of multimeric barcoding reagents as defined herein, or a kit as defined herein, to label a formalin-fixed paraffin-embedded (FFPE) nucleic acid sample, wherein the multimeric barcoding reagent or the components of the kit is/are introduced into the sample and used to label a set of two or more co-localised target nucleic acids for sequencing.

The invention further provides the use of a multimeric barcoding reagent as defined herein, a library of multimeric barcoding reagents as defined herein, or a kit as defined herein, to label target nucleic acids in an individual cell, wherein the multimeric barcoding reagent or the components of the kit is/are introduced into a cell and used to label a set of two or more target nucleic acids in the cell for sequencing.

The invention further provides the use of a multimeric barcoding reagent as defined herein, a library of multimeric barcoding reagents as defined herein, or a kit as defined herein, to label target nucleic acids in a sample of human plasma or serum, wherein the multimeric barcoding reagent or the components of the kit is/are used to label a set of two or more target nucleic acids in the plasma or serum for sequencing.

Methods for Profiling a Multimeric Barcoding Reagent or a Library of Multimeric Barcoding Reagents The invention further provides a method for profiling a multimeric barcoding reagent comprising the steps of: (a) preparing a nucleic acid sample for sequencing, optionally wherein the nucleic acid sample is prepared for sequencing according to one of the methods defined herein, wherein the sample comprises a target nucleic acid of known sequence; (b) sequencing the sample, optionally wherein the sample is sequenced by any of the methods defined herein; (c) processing the sequence data obtained by step (b), wherein the processing comprises identifying sequence reads comprising a sequence from the target nucleic acid of known sequence, identifying within these sequence reads the sequence of a barcode region, and determining the sequences of two or more barcode regions of the multimeric barcoding reagent.

The invention further provides a method for profiling a library of two or more multimeric barcoding reagents comprising the steps of: (a) preparing a nucleic acid sample for sequencing, optionally wherein the nucleic acid sample is prepared for sequencing by any one of the methods defined herein, wherein the sample comprises a first target nucleic acid of known sequence and a second target nucleic acid of known sequence; (b) sequencing the sample, optionally wherein the sample is sequenced by any of the methods defined herein; (c) processing the sequence data obtained by step (b), wherein the processing comprises (i) identifying sequence reads comprising a sequence from the first target nucleic acid of known sequence, identifying within these sequence reads the sequence of a barcode region, and determining the sequences of two or more barcode regions of the first multimeric barcoding reagent; and (ii) identifying sequence reads comprising a sequence from the second target nucleic acid of known sequence, identifying within these sequence reads the sequence of a barcode region, and determining the sequences of two or more barcode regions of the second multimeric barcoding reagent.

The methods of profiling may be used to determine which barcodes are present within each individual multimeric barcoding reagent within a solution of many such reagents. This would be useful where it is not known a priori which barcodes have been included in each barcoding reagent.

Target nucleic acids of known sequence may be prepared by synthesising a library of short (for example approximately 40-100 nucleotide) oligonucleotides; each oligonucleotide may comprise two constant (unvariable) regions at each end, flanking a central variable region comprising a stretch of randomised nucleotides (for example, 10 nucleotides in a sequence which could each be any one of the four canonical nucleotides).

Preferably, the number of distinct variable sequences present in this library may be configured to be substantially larger than the number of distinct barcodes present in the coding strand library to be profiled.

The oligonucleotides may be circularised, for example using a single-stranded ligase, or by first creating a double-stranded molecule using a primer-extension reaction from the 3' end of the molecule and then employing a double-stranded ligase for intramolecular circularisation. Following circularisation, double-stranded molecules may be denatured to convert them into single-stranded form.

A single primer may then bound to one of the constant regions of each of these circularised molecules and used to prime a strand-displacement amplification reaction using a processive polymerase with a strand-displacing activity (e.g. phi29 polymerase). This process may create a large number of tandem, linear copies of each individual circularised molecule, each comprised as a long single-stranded DNA sequence. These tandemly-repeated synthetic molecules then serve as the target nucleic acids of known sequence in the methods of the invention.

The invention is further defined in the following set of numbered clauses:

1. A multimeric barcoding reagent for labelling a target nucleic acid, wherein the reagent comprises:
   a. first and second barcode molecules linked together, wherein each of the barcode molecules comprises a nucleic acid sequence comprising a barcode region; and
   b. first and second barcoded oligonucleotides, wherein the first barcoded oligonucleotide comprises, optionally in the 5' to 3' direction, a barcode region annealed to the barcode region of the first barcode molecule and a target region capable of annealing or ligating to a first sub-sequence of the target nucleic acid, and wherein the second barcoded oligonucleotide comprises, optionally in the 5' to 3' direction, a barcode region annealed to the barcode region of the second barcode molecule and a target region capable of annealing or ligating to a second sub-sequence of the target nucleic acid.

2. The multimeric barcoding reagent of clause 1, wherein the barcode regions uniquely identify each of the barcode molecules.

3. The multimeric barcoding reagent of clause 1 or clause 2, wherein the target regions comprise different sequences.

4. The multimeric barcoding reagent of any one of clauses 1 to 3, wherein the barcode molecules are linked on a nucleic acid molecule.

5. The multimeric barcoding reagent of any one of clauses 1 to 3, wherein the barcode molecules are linked by attachment to a solid support.

6. The multimeric barcoding reagent of any one of clauses 1 to 5, wherein:

a. each of the barcode molecules comprises a nucleic acid sequence comprising in the 5' to 3' direction an adapter region and a barcode region;
b. the first barcoded oligonucleotide comprises in the 5' to 3' direction a barcode region annealed to the barcode region of the first barcode molecule, an adapter region annealed to the adapter region of the first barcode molecule and a target region capable of annealing to a first sub-sequence of the target nucleic acid; and
c. the second barcoded oligonucleotide comprises in the 5' to 3' direction a barcode region annealed to the barcode region of the second barcode molecule, an adapter region annealed to the adapter region of the second barcode molecule and a target region capable of annealing to a second sub-sequence of the target nucleic acid.

7. The multimeric barcoding reagent of any one of clauses 1 to 6, wherein the multimeric barcoding reagent comprises:
a. at least 5, at least 10, at least 20, at least 25, at least 50, at least 75 or at least 100 barcode molecules linked together, wherein each barcode molecule is as defined in an one of clauses 1 to 5; and
b. a barcoded oligonucleotide annealed to each barcode molecule, wherein each barcoded oligonucleotide is as defined in any one of clauses 1 to 5.

8. A library of multimeric barcoding reagents comprising first and second multimeric barcoding reagents as defined in any one of clauses 1 to 7, wherein the barcode regions of the first multimeric barcoding reagent are different to the barcode regions of the second multimeric barcoding reagent.

9. The library of multimeric barcoding reagents of clause 8, wherein the library comprises at least 5, at least 10, at least 20, at least 25, at least 50, at least 75, at least 100, at least 250, at least 500, at least $10^3$, at least $10^4$, at least $10^5$, at least $10^6$, at least $10^7$ or at least $10^8$ multimeric barcoding reagents as defined in any one of clauses 1 to 6, and wherein the barcode regions of each of the multimeric barcoding reagents are different to the barcode regions of the other multimeric barcoding reagents.

10. A method of preparing a nucleic acid sample for sequencing, wherein the method comprises the steps of:
a. contacting the nucleic acid sample with a multimeric barcoding reagent as defined in any one of clauses 1 to 7;
b. annealing the target region of the first barcoded oligonucleotide to a first sub-sequence of a target nucleic acid, and annealing the target region of the second barcoded oligonucleotide to a second sub-sequence of the target nucleic acid; and
c. extending the first and second barcoded oligonucleotides to produce first and second different barcoded target nucleic acid molecules, wherein each of the barcoded target nucleic acid molecules comprises at least one nucleotide synthesised from the target nucleic acid as a template.

11. The method of clause 10, wherein the method comprises contacting the nucleic acid sample with a library of multimeric barcoding reagents as defined in clause 8 or clause 9, and wherein:
a. the barcoded oligonucleotides of the first multimeric barcoding reagent anneal to sub-sequences of a first target nucleic acid and first and second different barcoded target nucleic acid molecules are produced, wherein each barcoded target nucleic acid molecule comprises at least one nucleotide synthesised from the first target nucleic acid as a template; and
b. the barcoded oligonucleotides of the second multimeric barcoding reagent anneal to sub-sequences of a second target nucleic acid and first and second different barcoded target nucleic acid molecules are produced, wherein each barcoded target nucleic acid molecule comprises at least one nucleotide synthesised from the second target nucleic acid as a template.

12. The method of clause 10 or clause 11, wherein the target nucleic acid is either an intact nucleic acid molecule or co-localised fragments of a nucleic acid molecule.

13. The method of any one of clauses 10 to 12, wherein the step of extending the barcoded oligonucleotides is performed while the barcoded oligonucleotides are annealed to the barcode molecules.

14. The method of any one of clauses 10 to 12, wherein the method further comprises the step of dissociating the barcoded oligonucleotides from the barcode molecules before annealing the target regions of the barcoded oligonucleotides to sub-sequences of the target nucleic acid.

15. The method of any one of clauses 10 to 14, wherein the method comprises producing at least 5, at least 10, at least 20, at least 25, at least 50, at least 75, at least 100, at least 250, at least 500, at least $10^3$, at least $10^4$, at least $10^5$, at least $10^6$, at least $10^7$ or at least $10^8$ different barcoded target nucleic acid molecules.

16. The method of any one of clauses 10 to 15, wherein the barcoded oligonucleotides are isolated from the nucleic acid sample after annealing to the sub-sequences of the target nucleic acid and before the barcoded target nucleic acid molecules are produced.

17. The method of any one of clauses 10 to 15, wherein the barcoded target nucleic acid molecules are isolated from the nucleic acid sample.

18. A method of synthesising a library of nucleic acid barcode molecules comprising:
a. contacting a first library of single-stranded sub-barcode molecules with a second library of single-stranded sub-barcode molecules, wherein each sub-barcode molecule comprises in the 5' to 3' direction a sub-barcode region and a downstream region, and wherein the downstream regions of sub-barcodes molecules from the first library are capable of annealing to the downstream regions of sub-barcode molecules from the second library;
b. annealing the downstream region of a first sub-barcode molecule from the first library to the downstream region of a first sub-barcode molecule from the second library, and annealing the downstream region of a second sub-barcode molecule from the first library to the downstream region of a second sub-barcode molecule from the second library; and
c. extending the 3' ends of the sub-barcode molecules to produce first and second double-stranded barcode molecules.

19. The method of clause 18, wherein each sub-barcode molecule further comprises an upstream region, and wherein each sub-barcode molecule comprises in the 5' to 3' direction an upstream region, a sub-barcode region and a downstream region.

20. The method of clause 18 or clause 19, wherein the first and second libraries of sub-barcode molecules each comprise at least 10, at least 50, at least 100, at least 250, at least 500, at least $10^3$, at least $10^4$ or at least $10^5$ different sub-barcode molecules.

21. The method of any one of clauses 18 to 20, wherein the method is used to synthesise a library of at least 100, at least 250, at least 500, at least $10^3$, at least $10^4$, at least $10^5$, at least $10^6$, at least $10^7$, at least $10^8$ or at least $10^9$ different barcode molecules.

22. The method of any one of clauses 18 to 21, wherein the method further comprises the step of dissociating the first and second double-stranded barcode molecules to produce first and second single-stranded barcode molecules.

23. A method of synthesising a library of nucleic acid barcode molecules comprising:
    a. contacting a first library of sub-barcode molecules with a second library of sub-barcode molecules, wherein each sub-barcode molecule comprises a sub-barcode region; and
    b. ligating a first sub-barcode molecule from the first library to a first sub-barcode molecule from the second library to form a first barcode molecule, and ligating a second sub-barcode molecule from the first library to a second sub-barcode molecule from the second library to form a second barcode molecule.

24. The method of clause 23, wherein the first and second libraries of sub-barcode molecules each comprise at least 10, at least 50, at least 100, at least 250, at least 500, at least $10^3$, at least $10^4$ or at least $10^6$ different sub-barcode molecules.

25. The method of clause 23 or clause 24, wherein the method is used to synthesise a library of at least 100, at least 250, at least 500, at least $10^3$, at least $10^4$, at least $10^6$, at least $10^6$, at least $10'$, at least $10^8$ or at least $10^9$ different barcode molecules.

26. The method of any one of clauses 23 to 25, wherein the sub-barcode molecules of the first and second libraries are single-stranded nucleic acids.

27. The method of any one of clauses 23 to 25, wherein the sub-barcode molecules of the first and second libraries are double-stranded nucleic acids.

28. The method of any one of clauses 23 to 27, wherein each sub-barcode molecule of the first library further comprises an upstream region, and wherein each sub-barcode molecule of the first library comprises in the 5' to 3' direction the upstream region and the sub-barcode region.

29. The method of any one of clauses 23 to 27, wherein each sub-barcode molecule of the second library further comprises a downstream region, and wherein each sub-barcode molecule of the second library comprises in the 5' to 3' direction the sub-barcode region and the downstream region.

30. The method of any one of clauses 23 to 27, wherein:
    a. each sub-barcode molecule of the first library further comprises an upstream region, and wherein each sub-barcode molecule of the first library comprises in the 5' to 3' direction the upstream region and the sub-barcode region;
    b. each sub-barcode molecule of the second library further comprises a downstream region, and wherein each sub-barcode molecule of the second library comprises in the 5' to 3' direction the sub-barcode region and the downstream region;
    c. the first barcode molecule comprises in the 5'-3' direction the upstream region of the first sub-barcode molecule of the first library, the sub-barcode region of the first sub-barcode molecule of the first library, the sub-barcode region of the first sub-barcode molecule of the second library and the downstream region of the first sub-barcode molecule of the second library; and
    d. the second barcode molecule comprises in the 5'-3' direction the upstream region of the second sub-barcode molecule of the first library, the sub-barcode region of the second sub-barcode molecule of the first library, the sub-barcode region of the second sub-barcode molecule of the second library and the downstream region of the second sub-barcode molecule of the second library.

31. The method of clause 30, wherein:
    a. the upstream region of each sub-barcode molecule of the first library comprises an upstream recognition site for a restriction endonuclease, optionally wherein the upstream recognition site is adjacent to the sub-barcode region; and/or
    b. the downstream region of each sub-barcode molecule of the second library comprises a downstream recognition site for a restriction endonuclease, optionally wherein the downstream recognition site is adjacent to the sub-barcode region.

32. The method of clause 31, wherein the method further comprises the step of cleaving the barcode molecules at the upstream recognition site and/or the downstream recognition site using a restriction endonuclease.

33. The method of clause 32, wherein the method further comprises the steps of:
    a. contacting the barcode molecules cleaved at the downstream recognition site with a further library of sub-barcode molecules, wherein each sub-barcode molecule of the further library comprises in the 5' to 3' direction a sub-barcode region and a downstream region; and
    b. ligating the first barcode molecule cleaved at the downstream recognition site to a first sub-barcode molecule of the further library to form a first extended barcode molecule, and ligating the second barcode molecule cleaved at the downstream recognition site to a second sub-barcode molecule of the further library to form a second extended barcode molecule;
    wherein the first extended barcode molecule comprises in the 5'-3' direction the upstream region of the first sub-barcode molecule of the first library, the sub-barcode region of the first sub-barcode molecule of the first library, the sub-barcode region of the first sub-barcode molecule of the second library, the sub-barcode region of the first sub-barcode molecule of the further library and the downstream region of the first sub-barcode molecule of the further library; and
    wherein the second extended barcode molecule comprises in the 5'-3' direction the upstream region of the second sub-barcode molecule of the first library, the sub-barcode region of the second sub-barcode molecule of the first library, the sub-barcode region of the second sub-barcode molecule of the second library, the sub-barcode region of the second sub-barcode molecule of the further library and the downstream region of the second sub-barcode molecule of the further library.

34. The method of clause 32, wherein the method further comprises the steps of:
    a. contacting the barcode molecules cleaved at the upstream recognition site with a further library of sub-barcode molecules, wherein each sub-barcode molecule of the further library comprises in the 5' to 3' direction an upstream region and a sub-barcode region; and
    b. ligating the first barcode molecule cleaved at the upstream recognition site to a first sub-barcode molecule of the further library to form a first extended barcode molecule, and ligating the second barcode molecule cleaved at the upstream recognition site to a second sub-barcode molecule of the further library to form a second extended barcode molecule;
  wherein the first extended barcode molecule comprises in the 5'-3' direction the upstream region of the first sub-barcode molecule of the further library, the sub-barcode region of the first sub-barcode molecule of the further library, the sub-barcode region of the first sub-barcode molecule of the first library, the sub-barcode region of the first sub-barcode molecule of the second library and the downstream region of the first sub-barcode molecule of the second library; and wherein the second extended barcode molecule comprises in the 5'-3' direction the upstream region of the second sub-barcode molecule of the further library, the sub-barcode region of the second sub-barcode molecule of the further library, the sub-barcode region of the second sub-barcode molecule of the first library, the sub-barcode region of the second sub-barcode molecule of the second library and the downstream region of the second sub-barcode molecule of the second library.
35. The method of clause 33, wherein the downstream region of each sub-barcode molecule of the further library comprises a downstream recognition site for a restriction endonuclease, optionally wherein the downstream recognition site is adjacent to the sub-barcode region.
36. The method of clause 34, wherein the upstream region of each sub-barcode molecule of the further library comprises an upstream recognition site for a restriction endonuclease, optionally wherein the upstream recognition site is adjacent to the sub-barcode region.
37. The method of clause 35 or clause 36, wherein the method further comprises the steps of:
  a. cleaving the extended barcode molecules at the downstream recognition site or the upstream recognition site of the sub-barcode molecule of the further library; and
  b. ligating the cleaved extended barcode molecules with a further library of sub-barcode molecules by the steps defined in clause 33 or clause 34.
38. The method of clause 37, wherein steps (a) and (b) of clause 37 are repeated at least 2, at least 3, at least 4, at least 5, at least 6, at least 7, at least 8, at least 9, at least 10, at least 25, at least 50, at least 100 or at least 250 times.
39. The method of clause 28, wherein the sub-barcode molecules are double-stranded nucleic acids, and wherein prior to step (a) of clause 23, the first library of sub-barcode molecules is ligated to a double-stranded downstream adapter molecule comprising a downstream adapter region to produce a library of ligation products, wherein the ligation is achieved by blunt-ended ligation, such that each molecule then comprises, in the 5' to 3' direction, the upstream region of a first sub-barcode molecule, and then the sub-barcode region of the first sub-barcode molecule, and then the downstream adapter region.
40. The method of clause 39, wherein the downstream adapter molecule comprises a 5' phosphate group on the 5' end that is ligated to the sub-barcode molecule in said ligation reaction.
41. The method of clause 39 or clause 40, wherein the method further comprises amplifying the library of ligation products to produce a library of amplified products, wherein the upstream region of each sub-barcode molecule comprises a forward priming sequence and the downstream adapter region comprises a reverse priming sequence, and wherein the step of amplifying is performed using a forward primer that anneals to the forward priming sequence and a reverse primer that anneals to the reverse priming sequence, optionally wherein the step of amplifying is by polymerase chain reaction.
42. The method of clause 41, wherein the method further comprises modifying the library of amplified products by reaction with a uracil DNA glycosylase enzyme, wherein the forward primer and/or the reverse primer comprises at least one deoxyuracil nucleotide.
43. The method of any one of clauses 39 to 42, wherein the upstream region of each sub-barcode molecule comprises a recognition site of a restriction endonuclease, and wherein the recognition site is positioned such that cleavage at the recognition site by a restriction endonuclease occurs adjacent to the sub-barcode region of the sub-barcode molecule.
44. The method of clause 43, wherein the recognition site of the restriction endonuclease is positioned 1, 2, less than 3, less than 4, less than 5 or less than 10 nucleotides upstream of the sub-barcode region of the first sub-barcode molecule.
45. The method of clause 44, wherein the restriction endonuclease is MlyI
46. The method of any one of clauses 43 to 45, wherein the method further comprises cleaving the library of ligation products or the library of amplified products at the recognition site using a restriction endonuclease to produce a library of cleaved products, optionally wherein the cleavage step is performed after the step of modification by reaction with a uracil DNA glycosylase enzyme.
47. The method of clause 46, wherein the steps of contacting and ligating defined in step (a) and (b) of clause 23 are performed with the library of cleaved products and a second library of sub-barcode molecules, wherein each sub-barcode molecule of the second library is double-stranded and comprises in the 5' to 3' direction an upstream region and a sub-barcode region, and wherein the second library of sub-barcode molecules comprises a recognition site of a restriction endonuclease as defined in any one of clauses 43 to 45.
48. The method of clause 47, wherein the steps of cleaving and ligation as defined in clauses 43 to 47 are repeated 1, 2, 3, 4, or 5 times, wherein each repeat involves the use of a further library of sub-barcode molecules, and optionally wherein each repeat involves repeating the step of amplification defined in clause 41, and further optionally wherein each repeat comprises repeating the step of modification as defined in clause 42.
49. A method of clause 48, wherein the last ligation step comprises the ligation of a double-stranded upstream adapter molecule comprising an upstream adapter region to the library of cleaved products to produce a library of ligation products, and optionally wherein the method further comprises amplifying the library of ligation products using a forward primer that anneals to a forward priming sequence in the upstream adapter region and a reverse primer that anneals to the reverse priming sequence in the downstream adapter region to form a library of amplification products.
50. A method of assembling a multimeric barcode molecule from two or more barcode molecules comprising:
  a. contacting a first barcode molecule with a first primer and contacting a second barcode molecule with a second primer, wherein each barcode molecule comprises a first strand comprising in the 5' to 3' direction a 5' region, a barcode region and a 3' region;

b. annealing the first primer to the 3' region of the first barcode molecule and annealing the second primer to the 3' region of the second barcode molecule;
c. extending the first primer to synthesise a second strand comprising a sequence complementary to the first strand of the first barcode molecule to form a first double-stranded barcode molecule, and extending the second primer to synthesise a second strand comprising a sequence complementary to the first strand of the second barcode molecule to form a second double-stranded barcode molecule;
d. ligating the first double-stranded barcode molecule to the second double-stranded barcode molecule.

51. A method of assembling a double-stranded multimeric barcode molecule from two or more single-stranded barcode molecules, wherein each barcode molecule comprises in the 5' to 3' direction a 5' region, a barcode region and a 3' region, the method comprising:
    a. contacting the first barcode molecule with a reverse splint primer, wherein the reverse splint primer comprises a 5' region complementary to the 5' region of the second barcode molecule and a 3' region complementary to the 3' region of the first barcode molecule, and contacting the second barcode molecule with a reverse termination primer, wherein the reverse termination primer comprises a 3' region complementary to the 3' region of the second barcode molecule;
    b. annealing the 3' region of the reverse splint primer to the 3' region of the first barcode molecule and annealing the 3' region of the reverse termination primer to the 3' region of the second barcode molecule;
    c. extending the reverse splint primer to synthesise a first extension product comprising a sequence complementary to the first barcode molecule, and extending the reverse termination primer to synthesise a second extension product comprising a sequence complementary to the second barcode molecule;
    d. contacting the first extension product with a forward termination primer, wherein the forward termination primer comprises a 3' region substantially identical to the 5' region of the first barcode molecule;
    e. annealing the 3' region of the forward termination primer to the 3' region of the first extension product;
    f. extending the forward termination primer to synthesise a third extension product comprising a sequence complementary to the first extension product;
    g. annealing the second and third extension products;
    h. extending the second and the third extension products at the 3' ends to form a double-stranded multimeric barcode molecule that comprises a first strand comprising the sequence of the first barcode molecule linked to the sequence of the second barcode molecule, and a second strand that is complementary to the first strand.

52. A method of assembling a double-stranded multimeric barcode molecule from two or more single-stranded barcode molecules, wherein each barcode molecule comprises in the 5' to 3' direction a 5' region, a barcode region and a 3' region, the method comprising:
    a. contacting the first barcode molecule with a reverse splint primer, wherein the reverse splint primer comprises a 5' region complementary to the 5' region of the second barcode molecule and a 3' region complementary to the 3' region of the first barcode molecule, and contacting the second barcode molecule with a reverse termination primer, wherein the reverse termination primer comprises a 3' region complementary to the 3' region of the second barcode molecule;
    b. annealing the 3' region of the reverse splint primer to the 3' region of the first barcode molecule and annealing the 3' region of the reverse termination primer to the 3' region of the second barcode molecule;
    c. extending the reverse splint primer to synthesise a first extension product comprising a sequence complementary to the first barcode molecule, and extending the reverse termination primer to synthesise a second extension product comprising a sequence complementary to the second barcode molecule;
    d. contacting the first extension product with a forward termination primer, wherein the forward termination primer comprises a 3' region substantially identical to the 5' region of the first barcode molecule, and contacting the second extension product with a forward splint primer, wherein the forward splint primer comprises a 5' region substantially identical to the 3' region of the first barcode molecule and a 3' region substantially identical to the 5' region of the second barcode molecule;
    e. annealing the 3' region of the forward termination primer to the 3' region of the first extension product and annealing the 3' region of the forward splint primer to the 3' region of the second extension product;
    f. extending the forward termination primer to synthesise a third extension product comprising a sequence complementary to the first extension product, and extending the second extension product using the forward splint primer to synthesise a fourth extension product comprising a sequence complementary to the 5' region of the forward splint primer;
    g. annealing the third and fourth extension products;
    h. extending the third and the fourth extension products at the 3' end to form a double-stranded multimeric barcode molecule that comprises a first strand comprising the sequence of the first barcode molecule linked to the sequence of the second barcode molecule, and a second strand that it complementary to the first strand.

53. The method of clause 51 or clause 52 wherein
    a. the forward termination primer comprises a 5' region comprising a forward reagent amplification sequence, and
    b. the reverse termination primer comprises a 5' region comprising a reverse reagent amplification sequence.

54. The method of clause 53, wherein the method further comprises amplifying the multimeric barcode molecule using a forward and reverse primer, wherein the forward primer anneals to the forward reagent amplification sequence and the reverse primer anneals to the reverse reagent amplification sequence.

55. The method of any one of clauses 50 to 54, wherein the multimeric barcode molecule is assembled using at least 5, at least 10, at least 20, at least 25, at least 50, at least 75, at least 100, at least 250, at least 500, at least $10^3$, at least $10^4$, at least $10^5$ or at least at least $10^6$ barcode molecules, wherein each barcode molecule comprises in the 5' to 3' direction a 5' region, a barcode region and a 3' region.

56. The method of any one of clauses 50 to 55, wherein the multimeric barcode molecule comprises the barcode regions of at least 5, at least 10, at least 20, at least 25, at least 50, at least 75, at least 100, at least 250, at least 500, at least $10^3$, at least $10^4$, at least $10^5$ or at least $10^6$ barcode molecules.

57. The method of any one of clauses 50 to 56, wherein a library of at least 5, at least 10, at least 20, at least 25, at least 50, at least 75, at least 100, at least 250, at least 500, at least $10^3$, at least $10^4$, at least $10^5$, at least $10^6$, at least $10^7$ or at least $10^8$ different multimeric barcode molecules is assembled.

58. The method of any one of clauses 50 to 57, wherein each barcode molecule is as defined in any one of clauses 1 to 9 or 18 to 49.

59. The method of clause 49, wherein the method further comprises annealing a forward splint primer to the library of ligation products or library of amplification products, wherein the forward splint primer comprises in the 5' to 3' direction a sequence complementary to the reverse primer of clause 49, and a sequence substantially identical to the forward primer of clause 49, and wherein the 3' end of the forward splint primer is extended to incorporate sequence from the ligation products or amplification products, and optionally wherein the extension reaction is performed using a DNA polymerase.

60. The method of clause 59, wherein the method further comprises annealing a forward termination primer to the ligation products or amplification products, wherein the forward termination primer comprises in the 5' to 3' direction a forward reagent amplification sequence and a sequence substantially identical to the forward primer of clause 49, and wherein the 3' end of the forward termination primer is extended to incorporate sequence from the ligation products or amplification products, and optionally wherein the extension reaction is performed using a DNA polymerase.

61. The method of clause 59 or clause 60, wherein the method further comprises annealing a reverse splint primer to the ligation products or amplification products, wherein the reverse splint primer comprises in the 5' to 3' direction a sequence complementary to the forward primer of clause 49 and a sequence substantially identical to the reverse primer of clause 49, and wherein the 3' end of the reverse splint primer is extended to incorporate sequence from the ligation products or amplification products, and optionally wherein the extension reaction is performed using a DNA polymerase.

62. The method any one of clauses 59 to 61, wherein the method further comprises annealing a reverse termination primer to the ligation products or amplification products, wherein the reverse termination primer comprises in the 5' to 3' direction a reverse reagent amplification sequence and a sequence substantially identical to the reverse primer of clause 49, and wherein the 3' end of the reverse termination primer is extended to incorporate sequence from the ligation products or amplification products, and optionally wherein the extension reaction is performed using a DNA polymerase.

63. The method of any one of clauses 59 to 62, wherein following annealing and extension of the primers, an overlap-extension amplification reaction is performed with two or more molecules from the annealing and extension process to produce a library of multimeric barcode molecules, optionally wherein the amplification reaction is performed by polymerase chain reaction, wherein each multimeric barcode molecule comprises the barcode regions from at least two barcode molecules.

64. The method of clause 63, wherein the method further comprises amplifying the multimeric barcode molecules using a forward primer substantially identical to the forward reagent amplification sequence and a reverse primer substantially identical to the reverse reagent amplification sequence, wherein the amplification reaction includes at least 1, at least 5, at least 10, at least 15, at least 20, or at least 30 cycles of amplification, optionally wherein the amplification is performed by polymerase chain reaction.

65. The method of clause 63 or clause 64, wherein the library of multimeric barcode molecules comprises at least 5, at least 10, at least 20, at least 25, at least 50, at least 75, at least 100, at least 250, at least 500, at least $10^3$, at least $10^4$, at least $10^5$, at least $10^6$, at least $10^7$ or at least $10^8$ different multimeric barcode molecules.

66. The method of clause 64 or clause 65, wherein the method further comprises a nucleic acid size-selection step to isolate multimeric barcode molecules of a defined length, optionally wherein the length is 900 to 1100 nucleotides, 4500 to 5500 nucleotides, or 9000 to 11000 nucleotides.

67. The method of any one of clauses 64 to 66, wherein the method further comprises performing one or more primer extension cycles on the amplified multimeric barcode molecules using either a single forward primer substantially identical to the forward reagent amplification sequence, or a single reverse primer substantially identical to the reverse reagent amplification sequence.

68. The method of clause 67, wherein one or more modified deoxyribonucleotides are incorporated during the primer extension cycles, optionally wherein the deoxyribonucleotides are modified with a biotin moiety or a deoxyuracil nucleotide.

69. A method of synthesising a multimeric barcoding reagent for labelling a target nucleic acid comprising:
   a. contacting first and second barcode molecules with first and second extension primers, wherein each of the barcode molecules comprises a single-stranded nucleic acid comprising in the 5' to 3' direction an adapter region, a barcode region and a priming region;
   b. annealing the first extension primer to the priming region of the first barcode molecule and annealing the second extension primer to the priming region of the second barcode molecule; and
   c. synthesising a first barcoded extension product by extending the first extension primer and synthesising a second barcoded extension product by extending the second extension primer, wherein the first barcoded extension product comprises a sequence complementary to the barcode region of the first barcode molecule and the second barcoded extension product comprises a sequence complementary to the barcode region of the second barcode molecule, and wherein the first barcoded extension product does not comprise a sequence complementary to the adapter region of the first barcode molecule and the second barcoded extension product does not comprise a sequence complementary to the adapter region of the second barcode molecule;
   and wherein the first and second barcode molecules are linked together.

70. The method of clause 69, wherein the method further comprises the following steps before the step of synthesising the first and second barcoded extension products:
   a. contacting first and second barcode molecules with first and second blocking primers; and
   b. annealing the first blocking primer to the adapter region of the first barcode molecule and annealing the second blocking primer to the adapter region of the second barcode molecule;
   and wherein the method further comprises the step of dissociating the blocking primers from the barcode molecules after the step of synthesising the barcoded extension products.

71. The method of clause 69 or clause 70, wherein following the synthesis of an extension product, a second extension step is performed, in which one or more of the four canonical deoxyribonucleotides is excluded from the reaction, such that the second extension step terminates at a position before the adapter region sequence, wherein the position comprises a nucleotide complementary to the excluded deoxyribonucleotide.
72. The method of clause 71, wherein said second extension step is performed with a polymerase lacking 3' to 5' exonuclease activity.
73. The method of any one of clauses 69 to 72, wherein the barcode molecules are synthesised by the method of clause 22 or clause 26.
74. The method of any one of clauses 69 to 73, wherein the barcode regions uniquely identify each of the barcode molecules.
75. The method of any one of clauses 69 to 74, wherein the barcode molecules are linked on a nucleic acid molecule.
76. The method of clause 75, wherein the barcode molecules are linked together in a ligation reaction.
77. The method of any one of clauses 69 to 74, wherein the barcode molecules are linked together by a further step comprising attaching the barcode molecules to a solid support.
78. The method of any one of clauses 69 to 74, wherein the first and second barcode molecules are assembled as a double-stranded multimeric barcode molecule prior to step (a) of clause 69 by the method of any one of clauses 50 to 68, and prior to step (a) of clause 69 the method further comprises dissociating the double-stranded multimeric barcode molecule to produce single-stranded multimeric barcode molecules.
79. The method of any one of clauses 69 to 78, further comprising the steps of:
    a. annealing an adapter region of a first adapter oligonucleotide to the adapter region of the first barcode molecule and annealing an adapter region of a second adapter oligonucleotide to the adapter region of the second barcode molecule, wherein the first adapter oligonucleotide further comprises a target region capable of annealing to a first sub-sequence of the target nucleic acid and the second adapter oligonucleotide further comprises a target region capable of annealing to a second sub-sequence of the target nucleic acid; and
    b. ligating the 3' end of the first barcoded extension product to the 5' end of the first adapter oligonucleotide to produce a first barcoded oligonucleotide and ligating the 3' end of the second barcoded extension product to the 5' end of the second adapter oligonucleotide to produce a second barcoded oligonucleotide.
80. The method of clause 79, wherein step (a) of clause 79 is performed before the step of synthesising the first and second barcoded extension products and wherein the step of synthesising the first and second barcoded extension products is conducted in the presence of a ligase enzyme which performs step (b) of clause 79.
81. The method of clause 80, wherein said ligase is a thermostable ligase, and wherein the extension and ligation reaction proceeds at over 37 degrees Celsius, over 45 degrees Celsius, or over 50 degrees Celsius.
82. The method of any one of clauses 79 to 81, wherein the target regions comprise two or more different sequences.
83. The method of any one of clauses 79 to 82, wherein the adapter regions of the adapter oligonucleotides comprise an identical constant region.
84. The method of any one of clauses 69 to 83, wherein the method comprises synthesising a multimeric barcoding reagent comprising at least 5, at least 10, at least 20, at least 25, at least 50, at least 75 or at least 100 barcode molecules, and wherein:
    a. each barcode molecule is as defined in an one of clauses 1 to 9 or 18 to 49; and
    b. a barcoded extension product is synthesised from each barcode molecule according to the method defined in any one of clauses 69 to 83; and, optionally,
    c. an adapter oligonucleotide is ligated to each of the barcoded extension products to produce barcoded oligonucleotides according to the method defined in any one of clauses 79 to 83.
85. A method of synthesising a library of multimeric barcoding reagents, wherein the method comprises repeating the steps of any one of clauses 69 to 84 to synthesise two or more multimeric barcoding reagents.
86. A kit for labelling a target nucleic acid, wherein the kit comprises:
    a. a multimeric barcoding reagent comprising:
        i. first and second barcode molecules linked together, wherein each of the barcode molecules comprises a nucleic acid sequence comprising, optionally in the 5' to 3' direction, an adapter region and a barcode region, and
        ii. first and second barcode oligonucleotides, wherein the first barcoded oligonucleotide comprises a barcode region annealed to the barcode region of the first barcode molecule, and wherein the second barcode oligonucleotide comprises a barcode region annealed to the barcode region of the second barcode molecule; and
    b. first and second adapter oligonucleotides, wherein the first adapter oligonucleotide comprises, optionally in the 5' to 3' direction, an adaptor region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adaptor region capable of annealing to the adapter region of the second barcode molecule and a target region capable of annealing or ligating to a second sub-sequence of the target nucleic acid.
87. The kit of clause 86, wherein each multimeric barcoding reagent is as defined in any one of clauses 1 to 9 or 69 to 85.
88. The kit of clause 86 or clause 87, wherein each barcode molecule is as defined in any one of clauses 1 to 9 or 18 to 68.
89. The kit of any one of clauses 86 to 88, wherein the barcode regions uniquely identify each of the barcode molecules.
90. The kit of any one of clauses 86 to 89, wherein the target regions comprise different sequences.
91. The kit of any one of clauses 86 to 90, wherein the adapter regions of the adapter oligonucleotides comprise an identical constant region.
92. The kit of any one of clauses 86 to 91, wherein the barcode molecules are linked on a nucleic acid molecule.
93. The kit of any one of clauses 86 to 92, wherein the barcode molecules are linked by attachment to a solid support.

94. The kit of any one of clauses 86 to 93, wherein the multimeric barcoding reagent(s) and adapter oligonucleotides are provided in the kit as physically separated components.

95. The kit of any one of clauses 86 to 94, wherein the kit comprises:
   a. a multimeric barcoding reagent comprising at least 5, at least 10, at least 20, at least 25, at least 50, at least 75 or at least 100 barcode molecules linked together, wherein each barcode molecule is as defined in an one of clauses 1 to 9, 18 to 68, or 86 to 94; and
   b. an adaptor oligonucleotide capable of annealing to each barcode molecule, wherein each adaptor oligonucleotide is as defined in any one of clauses 79 to 94.

96. The kit of any one of clauses 86 to 95, wherein the kit comprises a library of two or more multimeric barcoding reagents, wherein each multimeric barcoding reagent is as defined in any one of clauses 1 to 9 or 69 to 95, and adaptor oligonucleotides for each of the multimeric barcoding reagents, wherein each adaptor oligonucleotide is as defined in any one of clauses 79 to 95, wherein the barcode regions of the first multimeric barcoding reagent are different to the barcode regions of the second multimeric barcoding reagent.

97. The kit of clause 96, wherein the kit comprises a library of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents, wherein each multimeric barcoding reagent is as defined in any one of clauses 1 to 9 or 69 to 95, and adaptor oligonucleotides for each of the multimeric barcoding reagents, wherein each adaptor oligonucleotide is as defined in any one of clauses 79 to 95, and wherein the barcode regions of each of the multimeric barcoding reagents are different to the barcode regions of the other multimeric barcoding reagents.

98. A method of preparing a nucleic acid sample for sequencing, wherein the method comprises the steps of:
   a. contacting the nucleic acid sample with a first and second adapter oligonucleotide as defined in any one of clauses 86 to 97;
   b. annealing the target region of the first adapter oligonucleotide to a first sub-sequence of a target nucleic acid, and annealing the target region of the second adapter oligonucleotide to a second sub-sequence of the target oligonucleotide;
   c. contacting the nucleic acid sample with a multimeric barcoding reagent as defined in any one of clauses 86 to 97;
   d. annealing the adapter region of the first adapter oligonucleotide to the adapter region of the first barcode molecule, and annealing the adapter region of the second adapter oligonucleotide to the adapter region of the second barcode molecule; and
   e. ligating the 3' end of the first barcode oligonucleotide to the 5' end of the first adapter oligonucleotide to produce a first barcoded oligonucleotide and ligating the free 3' end of the second barcode oligonucleotide to the 5' end of the second adapter oligonucleotide to produce a second barcoded oligonucleotide;
   and wherein the first and second barcoded oligonucleotides are extended to produce first and second different barcoded target nucleic acid molecules each of which comprises at least one nucleotide synthesised from the target nucleic acid as a template.

99. The method of clause 98, wherein steps (a) and (b) are performed using adaptor oligonucleotides as defined in clause 96 or clause 97, and steps (c) to (e) are performed using a library of multimeric barcoding reagents as defined in clause 96 or clause 97, and wherein:
   a. the barcoded oligonucleotides of the first multimeric barcoding reagent anneal to sub-sequences of a first target nucleic acid and first and second different barcoded target nucleic acid molecules are produced, wherein each barcoded target nucleic acid molecule comprises at least one nucleotide synthesised from the first target nucleic acid as a template; and
   b. the barcoded oligonucleotides of the second multimeric barcoding reagent anneal to sub-sequences of a second target nucleic acid and first and second different barcoded target nucleic acid molecules are produced, wherein each barcoded target nucleic acid molecule comprises at least one nucleotide synthesised from the second target nucleic acid as a template.

100. The method of clause 98 or clause 99, wherein the target nucleic acid is either an intact nucleic acid molecule or co-localised fragments of a nucleic acid molecule.

101. The method of any one of clauses 98 to 100, wherein the step of extending the barcoded oligonucleotides is performed before step (c), before step (d) and/or before step (e), and wherein the first and second barcoded oligonucleotides remain annealed to the first and second barcode molecules until after step (e).

102. The method of any one of clauses 98 to 100, wherein the step of extending the barcoded oligonucleotides is performed after step (e).

103. The method of any one of clauses 98 to 102, wherein the method comprises producing at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different barcoded target nucleic acid molecules.

104. The method of any one of clauses 98 to 103, wherein the barcoded oligonucleotides are isolated from the nucleic acid sample after annealing to the sub-sequences of the target nucleic acid and before the barcoded target nucleic acid molecules are produced.

105. The method of any one of clauses 98 to 103, wherein the barcoded target nucleic acid molecules are isolated from the nucleic acid sample.

106. A method of sequencing a sample prepared according the methods of any one of clauses 10 to 17 or clauses 98 to 105 comprising the steps of:
   a. isolating the barcoded target nucleic acid molecules, and
   b. producing a sequence read from each barcoded target nucleic acid molecule that comprises the barcode region, the target region and at least one additional nucleotide from the target nucleic acid.

107. The method of clause 106, wherein each sequence read comprises at least 10, at least 25, at least 50, at least 100, at least 250 or at least 500 nucleotides from the target nucleic acid.

108. A method for processing sequencing data obtained by the method of clause 106 or clause 107 comprising the steps of:
   a. identifying for each sequence read the sequence of the barcode region and the sequence from the target nucleic acid; and
   b. using the information from step (a) to determine a group of sequences from the target nucleic acid that were labelled with barcode regions from the same multimeric barcoding reagent.
109. The method of clause 108 further comprising the step of determining a sequence of a target nucleic acid by analysing the group of sequences to identify contiguous sequences, wherein the sequence of the target nucleic acid comprises nucleotides from at least two sequence reads.
110. The method of clause 108 or clause 109, wherein the target nucleic acid is either an intact nucleic acid molecule or co-localised fragments of a nucleic acid molecule.
111. A method of generating a synthetic long read from a target nucleic acid comprising the steps of:
   a. preparing a nucleic acid sample for sequencing according to the method of any one of clauses 10 to 17, or clauses 98 to 105;
   b. sequencing the sample according to the method of clause 106 or clause 107; and
   c. processing the sequence data obtained by step (b) according to the method of any one of clauses 108 to 110;
   wherein step (c) generates a synthetic long read comprising at least one nucleotide from each of the at least two sequence reads.
112. A method of sequencing two or more co-localised target nucleic acids comprising the steps of:
   a. preparing a nucleic acid sample for sequencing according to the method of any one of clauses 10 to 17, or clauses 98 to 105;
   b. sequencing the sample according to the method of clause 106 or clause 107; and
   c. processing the sequence data obtained by step (b) according to the method of any one of clauses 108 to 110;
   wherein step (c) identifies at least two sequence reads comprising nucleotides from at least two target nucleic acids co-localised in the sample.
113. A method of sequencing target nucleic acids from an individual cell comprising the steps of:
   a. preparing a nucleic acid sample for sequencing according to the method of clauses 10 to 17, or clauses 98 to 105, wherein the multimeric barcoding reagent(s) and/or adaptor oligonucleotides are introduced into the cell;
   b. sequencing the sample according to the method of clause 106 or clause 107; and
   c. processing the sequence data obtained by step (b) according to the method of any one of clauses 108 to 110;
   wherein step (c) identifies at least two sequence reads comprising nucleotides from at least two target nucleic acids from the cell.
114. The method of clause 113, wherein the multimeric barcoding reagent(s) and/or adaptor oligonucleotides are introduced into the cell by chemical complexation with a lipid transfection reagent and then transfection into the cell.
115. The method of clause 113, wherein the multimeric barcoding reagent(s) and/or adaptor oligonucleotides are introduced into the cell through the steps of:
   a. permeabilising the cell membrane by contacting it with a chemical surfactant; and then
   b. contacting the cell with the multimeric barcoding reagent(s) and/or adaptor oligonucleotides.
116. The method of clause 115, wherein the chemical surfactant is a non-ionic surfactant.
117. The method of clause 115 or clause 116, wherein the chemical surfactant is Triton X-100 ($C_{14}H_{22}O(C_2H_4O)_n$ (n=9-10)).
118. A method of any one of clauses 115 to 117, wherein the chemical surfactant is in solution at a concentration of less than 200 micromolar, or less than 500 micromolar, or less than 1 milimolar.
119. The method of any one of clauses 113 to 118, wherein, following the step of introducing the multimeric barcoding reagent(s) and/or adaptor oligonucleotides into the cell, the cell is incubated for a period of time to allow the target regions of the multimeric barcoding reagent(s) or adapter oligonucleotide(s) to anneal to sub-sequences of the target nucleic acids within the cell.
120. The method of clause 119, wherein the incubation period is at least 1 minute, or at least 5 minutes, or at least 15 minutes, or at least 30 minutes, or at least 60 minutes.
121. The method of clause 119 or clause 120, wherein the incubation takes place within a solution containing a nucleic acid denaturant, such as DMSO or betaine.
122. The method of any of one of clauses 119 to 121, wherein the incubation takes place at a temperature of at least 37 degrees Celsius, at least 45 degrees Celsius, or at least 50 degrees Celsius.
123. The method of any one of clauses 113 to 122, wherein following introduction of the multimeric barcoding reagent(s) and/or adaptor oligonucleotides into the cell, and optionally following the incubation step, the cell is contacted by a solution of oligonucleotides complementary to the target regions of the multimeric barcoding reagents.
124. The method of any one of clauses 113 to 123, wherein following introduction of the multimeric barcoding reagent(s) and/or adaptor oligonucleotides into the cell, and optionally following the incubation step, the cell is isolated from a reaction mixture by centrifugation.
125. The method of any one of clauses 113 to 124, wherein following introduction of the multimeric barcoding reagent(s) and/or adaptor oligonucleotides into the cell, and optionally following the incubation step, the barcoded oligonucleotides and/or barcoded target nucleic acid molecules and/or multimeric barcoding reagent(s) are isolated from the cell.
126. The method of any one of clauses 113 to 125, wherein the multimeric barcoding reagents, barcoded oligonucleotides and/or adaptor oligonucleotides comprise one or more biotin moieties.
127. The method of any one of clauses 113 to 126, wherein following introduction of the multimeric barcoding reagent(s) and/or adaptor oligonucleotides into the cell, and optionally following the incubation step, the barcoded oligonucleotides and/or barcoded target nucleic acid molecules and/or multimeric barcoding reagent(s) are isolated by a process of:
   c. dissolving the cell membranes, optionally using a chemical surfactant or by incubation at high temperature;
   d. contacting the resulting mixture with a solid support, optionally wherein the solid support comprises streptavidin moieties; and
   e. capturing the barcoded oligonucleotides and/or barcoded target nucleic acid molecules and/or multimeric barcoding reagent(s) on the solid support, optionally through streptavidin-biotin interaction.
128. The method of clause 127, wherein the solid support is one or more magnetic beads, optionally wherein the one or more magnetic beads comprise streptavidin molecules on their surface.

129. The method of clause 128, wherein the magnetic bead(s) are isolated from a reaction mixture with a magnet.
130. The method of any one of clauses 113 to 129, wherein the target nucleic acids are mRNA molecules.
131. The method of clause 130, wherein each barcoded target nucleic acid molecule is produced after isolation of the barcoded oligonucleotide annealed to a target mRNA molecule by extending the barcoded oligonucleotide using a reverse transcriptase and the target mRNA molecule as the template.
132. The method of clause 130 or 131, wherein the mRNA molecules are mRNA molecules corresponding to alpha and/or beta chains of a T-cell receptor sequence, optionally wherein the sequences of alpha and beta chains paired within an individual cell are determined.
133. The method of clause 130 or 131, wherein the mRNA molecules are mRNA molecules corresponding to light and/or heavy chains of an immunoglobulin sequence, optionally wherein the sequences of light and heavy chains paired within an individual cell are determined.
134. The method of any one of clauses 113 to 133, wherein at least 100, or at least $10^3$, at least $10^4$, at least $10^5$, at least $10^6$, at least $10^7$, at least $10^8$ or at least $10^9$ cells are sequenced.
135. Use of a multimeric barcoding reagent as defined in any one of clauses 1 to 7, a library of multimeric barcoding reagents as defined in clause 8 or clause 9, or a kit as defined in any one of clauses 86 to 97, to produce two or more sequence reads from a target nucleic acid, wherein two or more sequence reads are identified as derived from the same target nucleic acid and combined to produce a synthetic long read.
136. Use of a multimeric barcoding reagent as defined in any one of clauses 1 to 7, a library of multimeric barcoding reagents as defined in clause 8 or clause 9, or a kit as defined in any one of clauses 86 to 97, to label a formalin-fixed paraffin-embedded nucleic acid sample, wherein the multimeric barcoding reagent or the components of the kit is/are introduced into the sample and used to label a set of two or more co-localised target nucleic acids for sequencing.
137. Use of a multimeric barcoding reagent as defined in any one of clauses 1 to 7, a library of multimeric barcoding reagents as defined in clause 8 or clause 9, or a kit as defined in any one of clauses 86 to 97, to label target nucleic acids in an individual cell, wherein the multimeric barcoding reagent or the components of the kit is/are introduced into a cell and used to label a set of two or more target nucleic acids in the cell for sequencing.
138. Use of a multimeric barcoding reagent as defined in any one of clauses 1 to 7, a library of multimeric barcoding reagents as defined in clause 8 or clause 9, or a kit as defined in any one of clauses 86 to 97, to label target nucleic acids in a sample of human plasma or serum, wherein the multimeric barcoding reagent or the components of the kit is/are used to label a set of two or more target nucleic acids in the plasma or serum for sequencing.
139. A method for profiling a multimeric barcoding reagent comprising the steps of:
  a. preparing a nucleic acid sample for sequencing according to the method of clauses 10 to 17, or clauses 98 to 105, wherein the sample comprises a target nucleic acid of known sequence;
  b. sequencing the sample according to the method of clause 106 or clause 107;
  c. processing the sequence data obtained by step (b), wherein the processing comprises identifying sequence reads comprising a sequence from the target nucleic acid of known sequence, identifying within these sequence reads the sequence of a barcode region, and determining the sequences of two or more barcode regions of the multimeric barcoding reagent.
140. A method for profiling a library of two or more multimeric barcoding reagents comprising the steps of:
  a. preparing a nucleic acid sample for sequencing according to the method of clauses 10 to 17, or clauses 98 to 105, wherein the sample comprises a first target nucleic acid of known sequence and a second target nucleic acid of known sequence;
  b. sequencing the sample according to the method of clause 106 or clause 107;
  c. processing the sequence data obtained by step (b), wherein the processing comprises:
    i. identifying sequence reads comprising a sequence from the first target nucleic acid of known sequence, identifying within these sequence reads the sequence of a barcode region, and determining the sequences of two or more barcode regions of the first multimeric barcoding reagent; and
    ii. identifying sequence reads comprising a sequence from the second target nucleic acid of known sequence, identifying within these sequence reads the sequence of a barcode region, and determining the sequences of two or more barcode regions of the second multimeric barcoding reagent.

BRIEF DESCRIPTION OF THE DRAWINGS

The invention, together with further objects and advantages thereof, may best be understood by making reference to the description taken together with the accompanying drawings, in which:

FIG. 19 is a table showing the results of barcoding genomic DNA loci of three human genes (BRCA1, HLA-A and DQB1) with multimeric barcoding reagents containing barcoded oligonucleotides.

EXAMPLES

Materials and Methods

Figure 1:
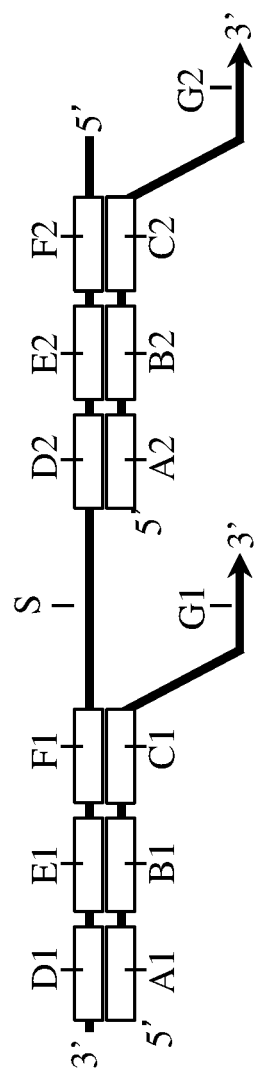
FIG. 1 illustrates a multimeric barcoding reagent that may be used in the method illustrated in FIG. 2 or FIG. 3.
Figure 2:
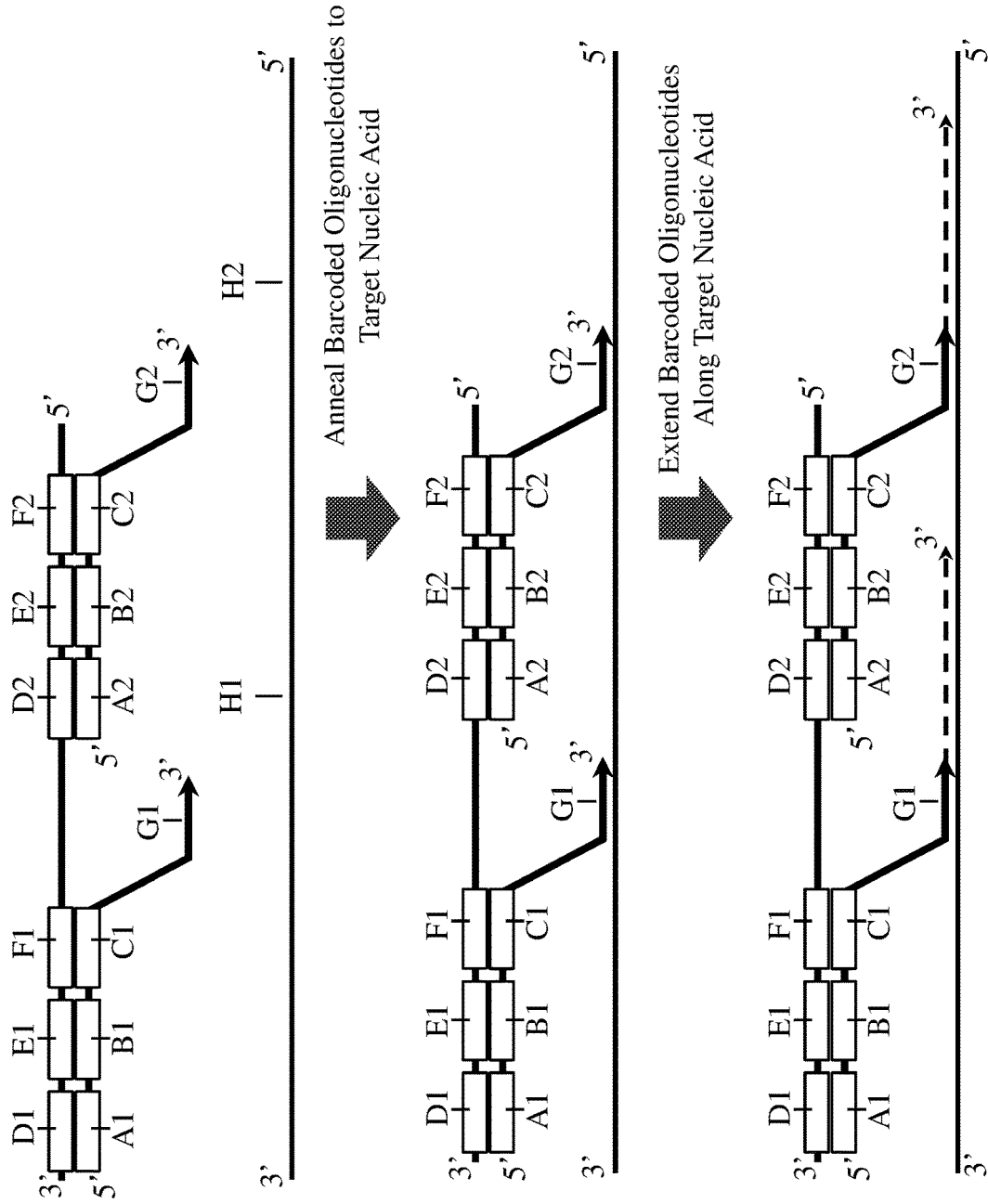
FIG. 2 illustrates a first method of preparing a nucleic acid sample for sequencing using a multimeric barcoding reagent.
Figure 3:
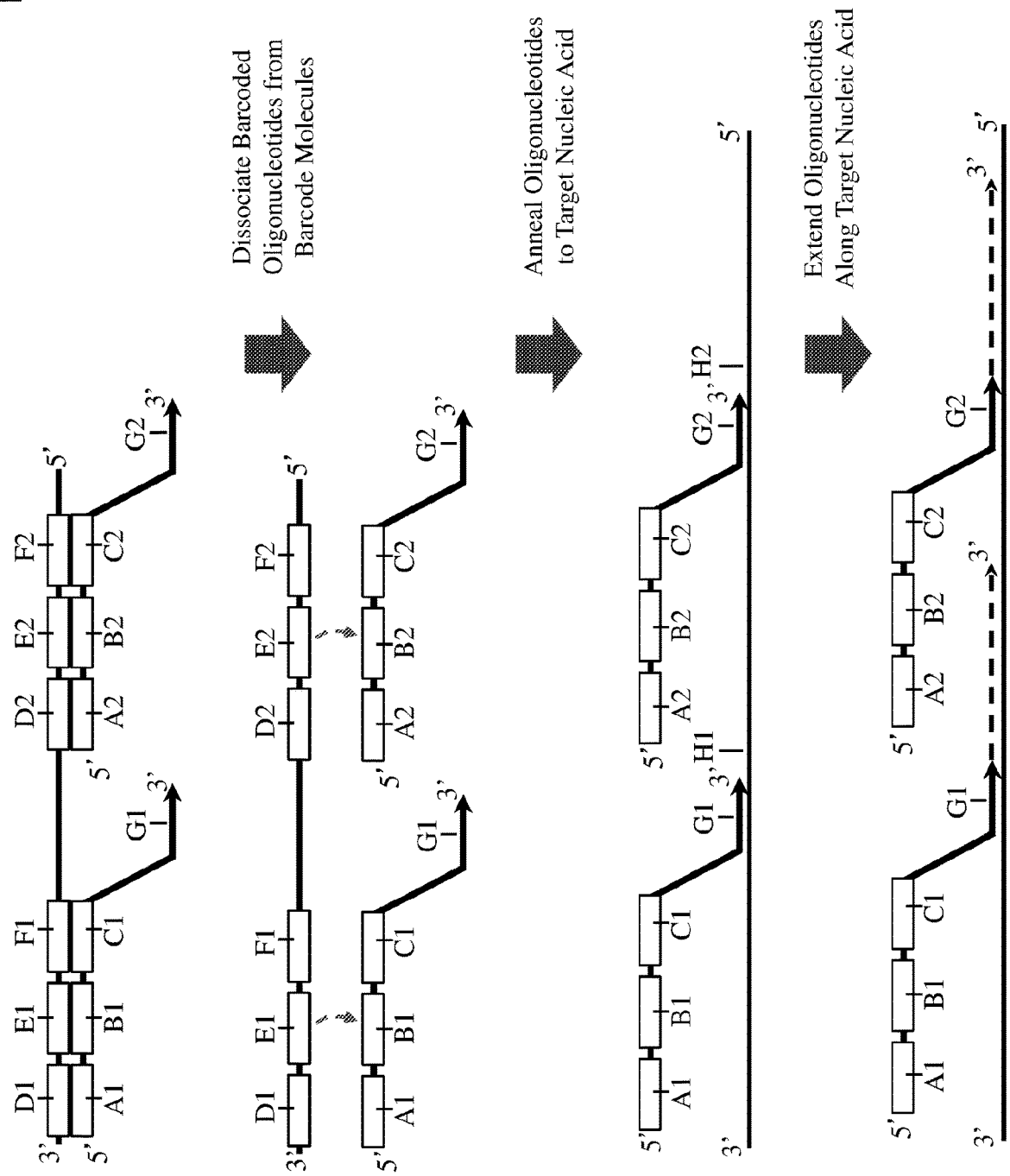
FIG. 3 illustrates a second method of preparing a nucleic acid sample for sequencing using a multimeric barcoding reagent.
Figure 4:
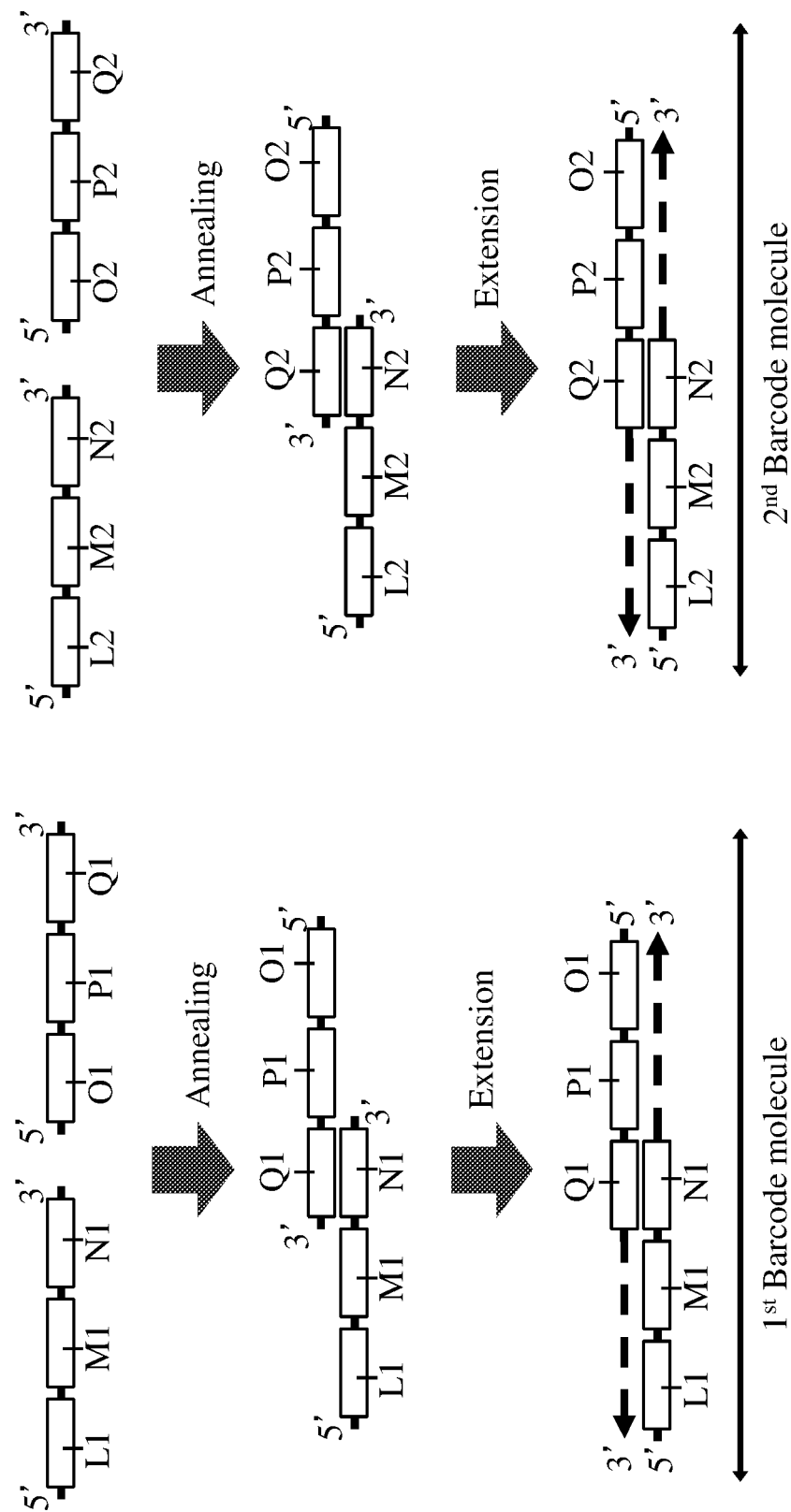
FIG. 4 illustrates a method of synthesising a library of barcode molecules from sub-barcode libraries using the steps of annealing and extending.
Figure 5:
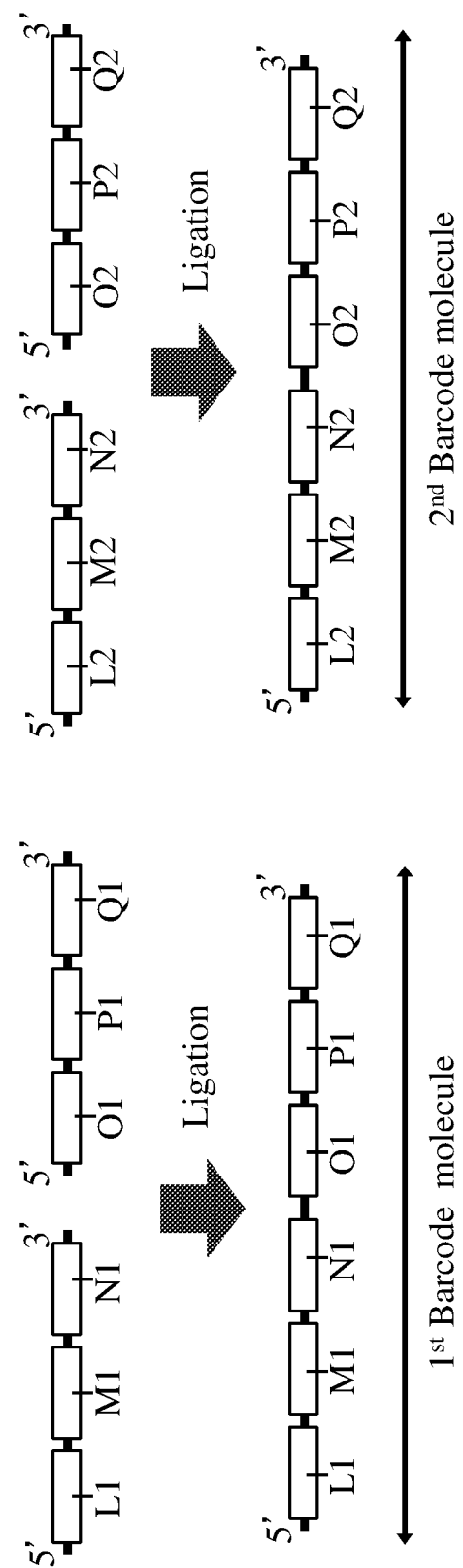
FIG. 5 illustrates a method of synthesising a library of barcode molecules from sub-barcode libraries using ligation.
Figure 6:
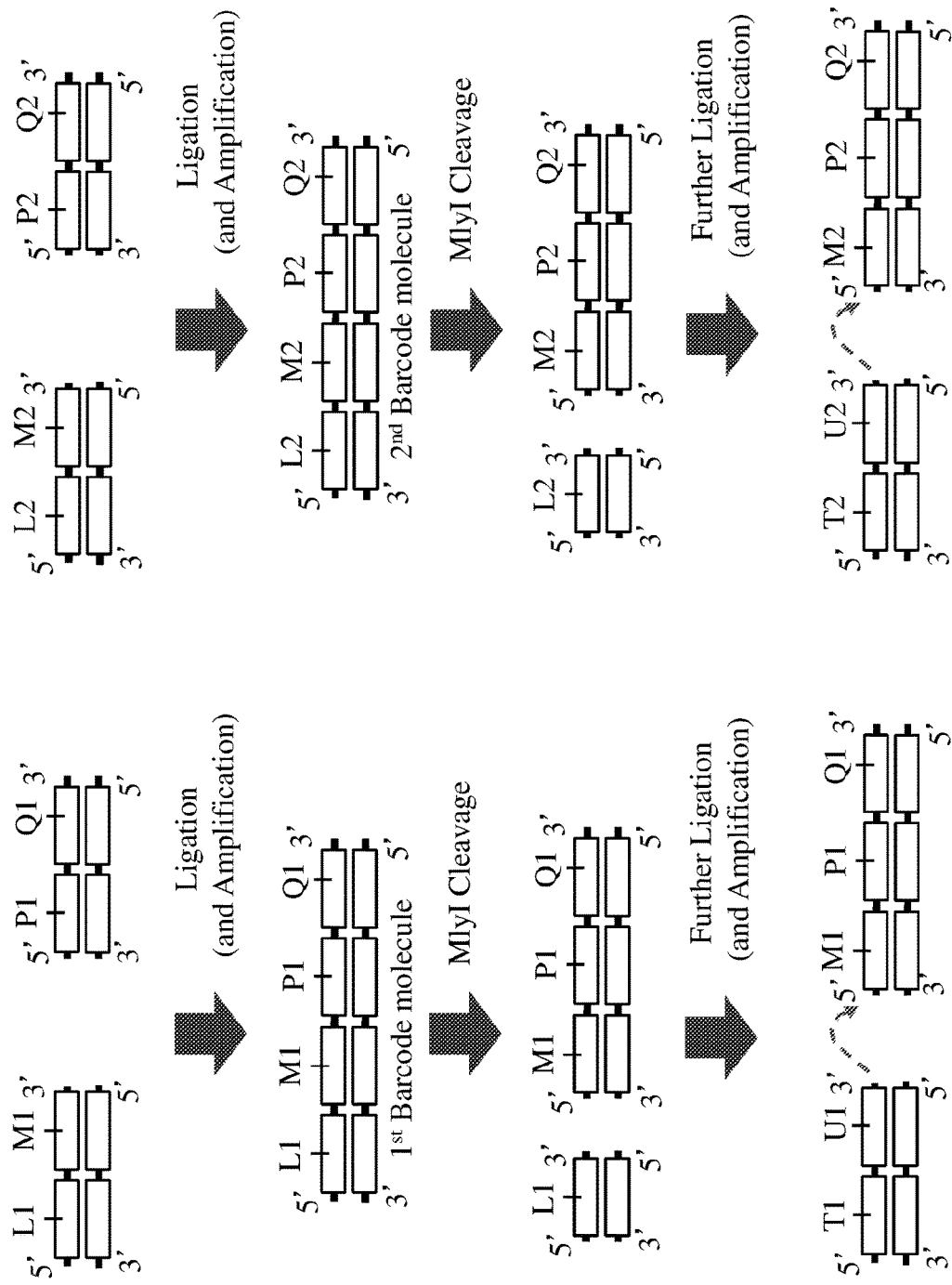
FIG. 6 illustrates a method of synthesising a library of barcode molecules by ligation and cleavage.
Figure 7:
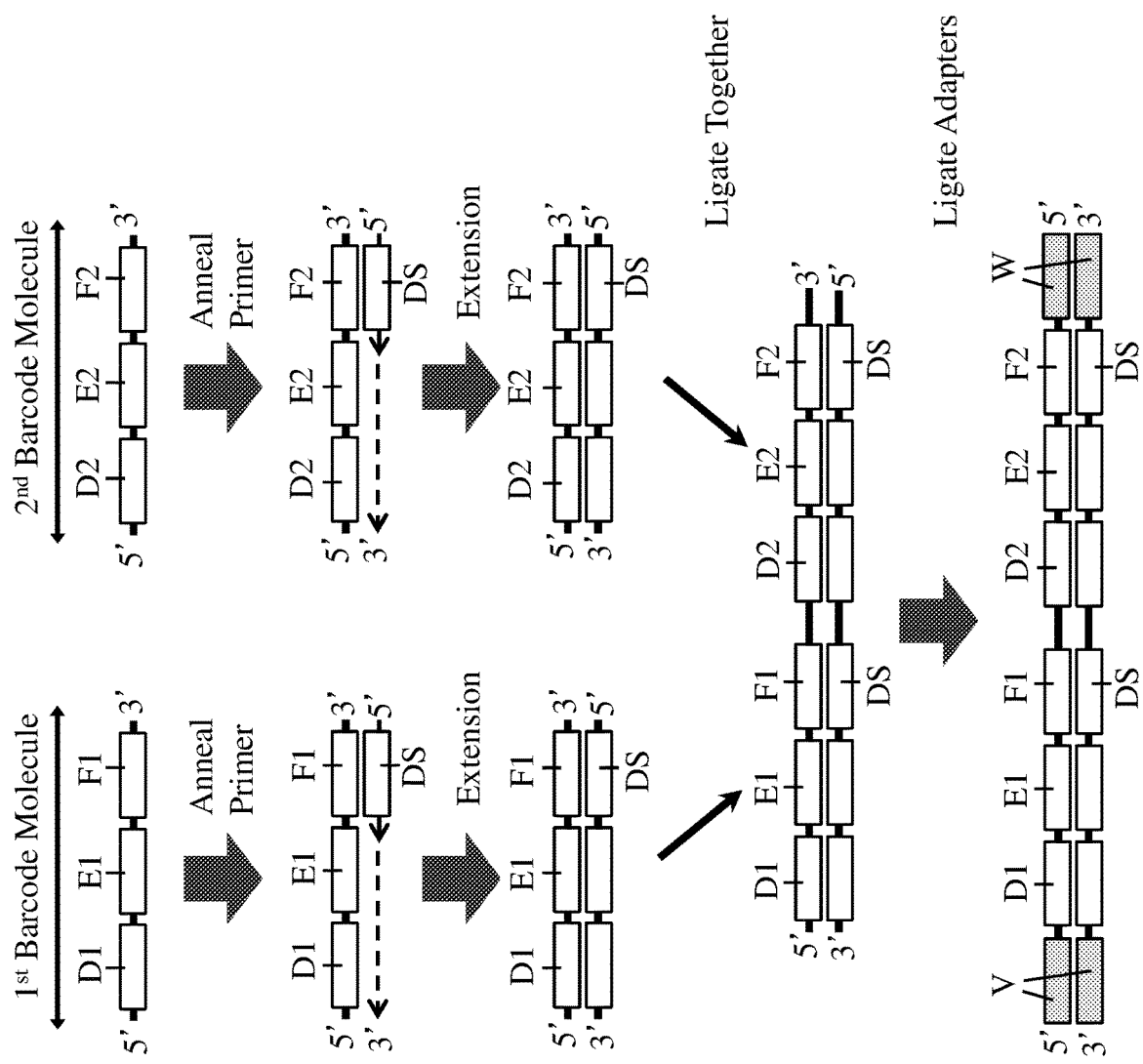
FIG. 7 illustrates a method of assembling a multimeric barcode molecule (a precursor to a multimeric barcoding reagent) from two or more barcode molecules.
Figure 8:
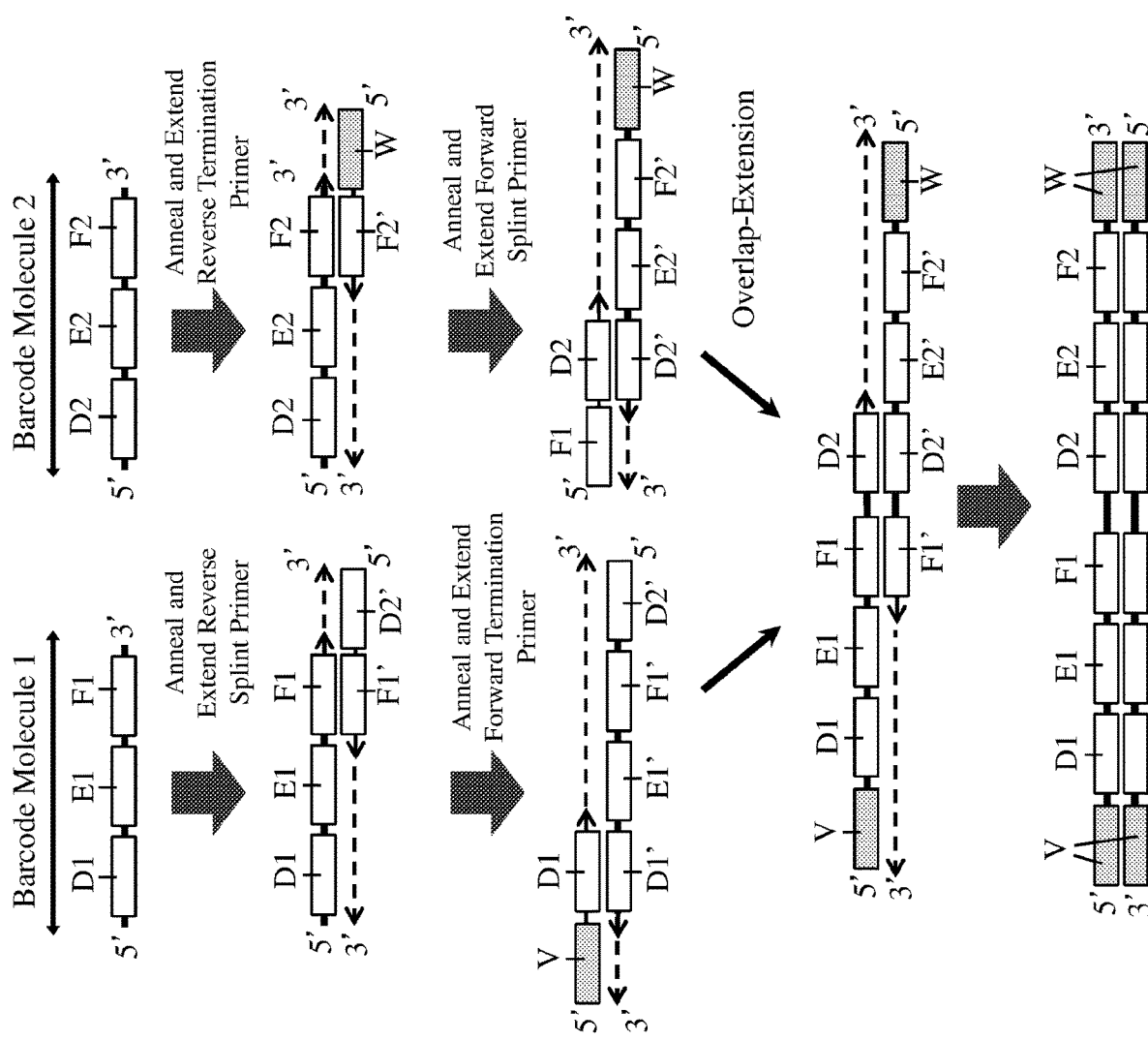
FIG. 8 illustrates an alternative method of assembling a multimeric barcode molecule (a precursor to a multimeric barcoding reagent) from two or more barcode molecules.
Figure 9:
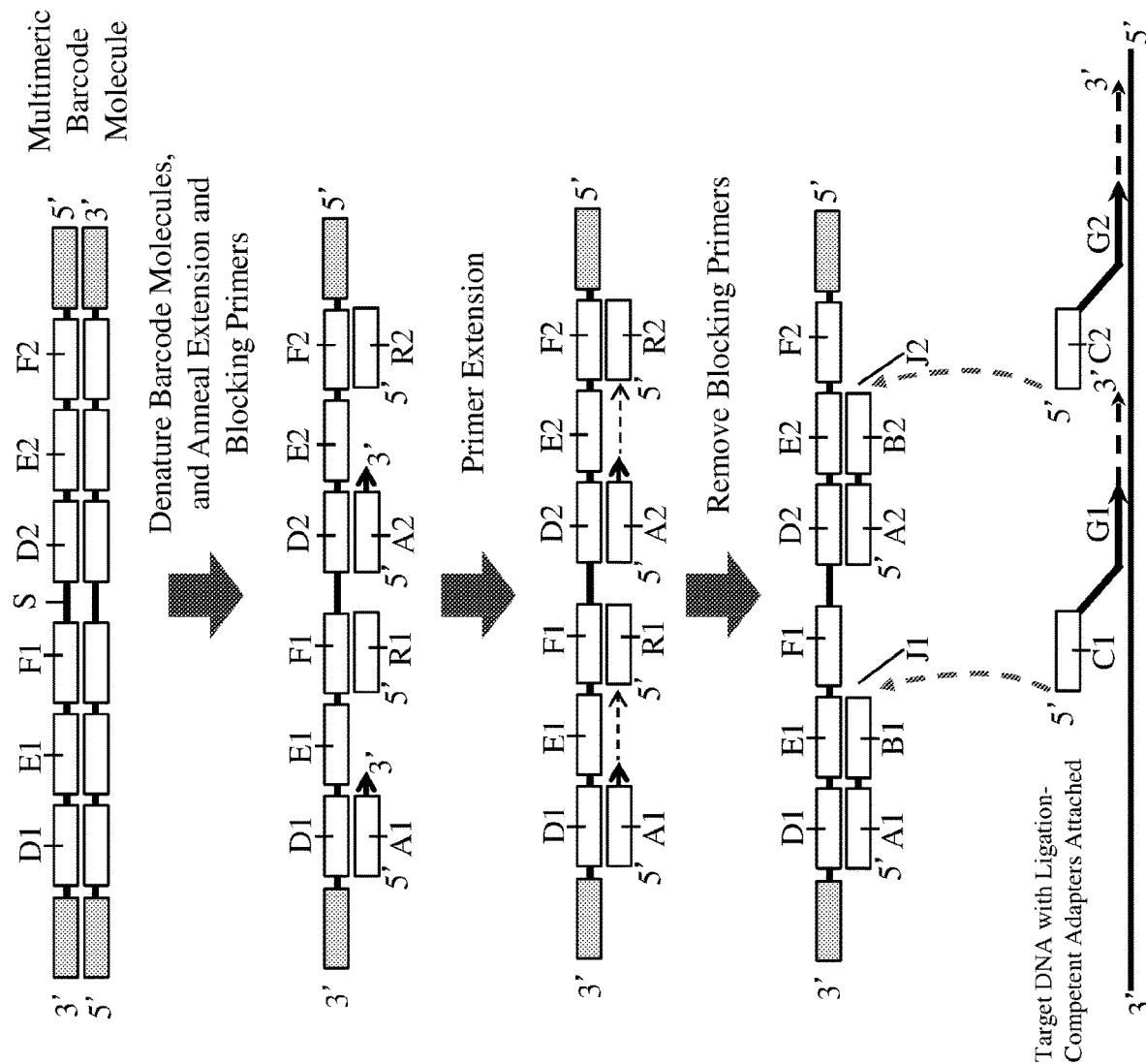
FIG. 9 illustrates a method of synthesizing multimeric barcoding reagents for labeling a target nucleic acid that may be used in the methods illustrated in FIG. 2, FIG. 3 and/or FIG. 12.
Figure 10:
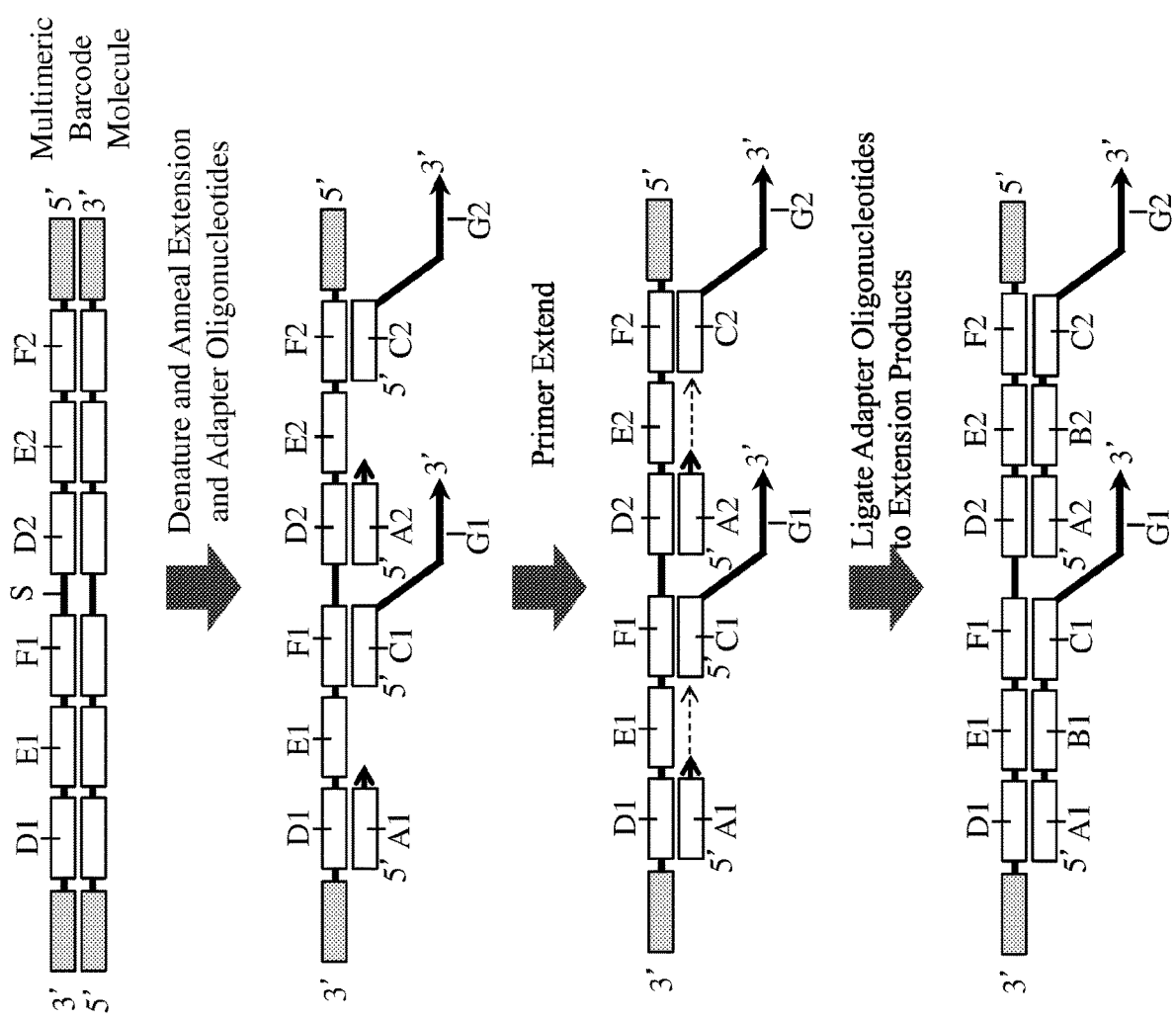
FIG. 10 illustrates an alternative method of synthesizing multimeric barcoding reagents (as illustrated in FIG. 1) for labeling a target nucleic acid that may be used in the method illustrated in FIG. 2 and/or FIG. 3.
Figure 11:
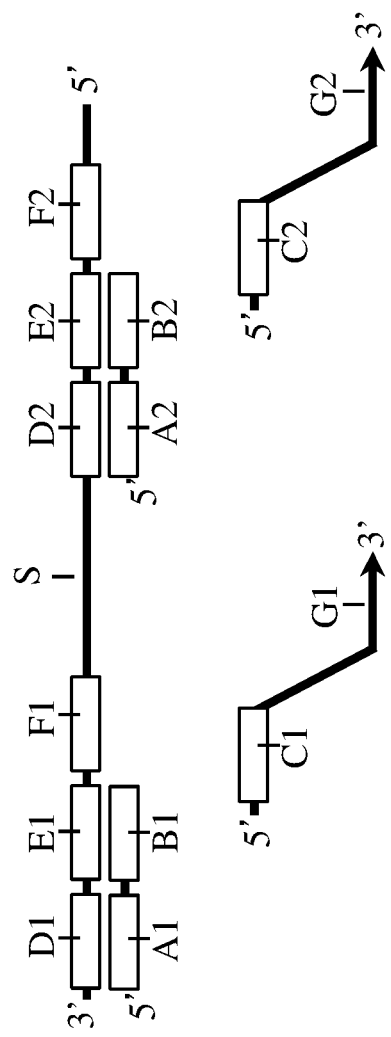
FIG. 11 illustrates a kit comprising a multimeric barcoding reagent and adapter oligonucleotides for labelling a target nucleic acid.
Figure 12:
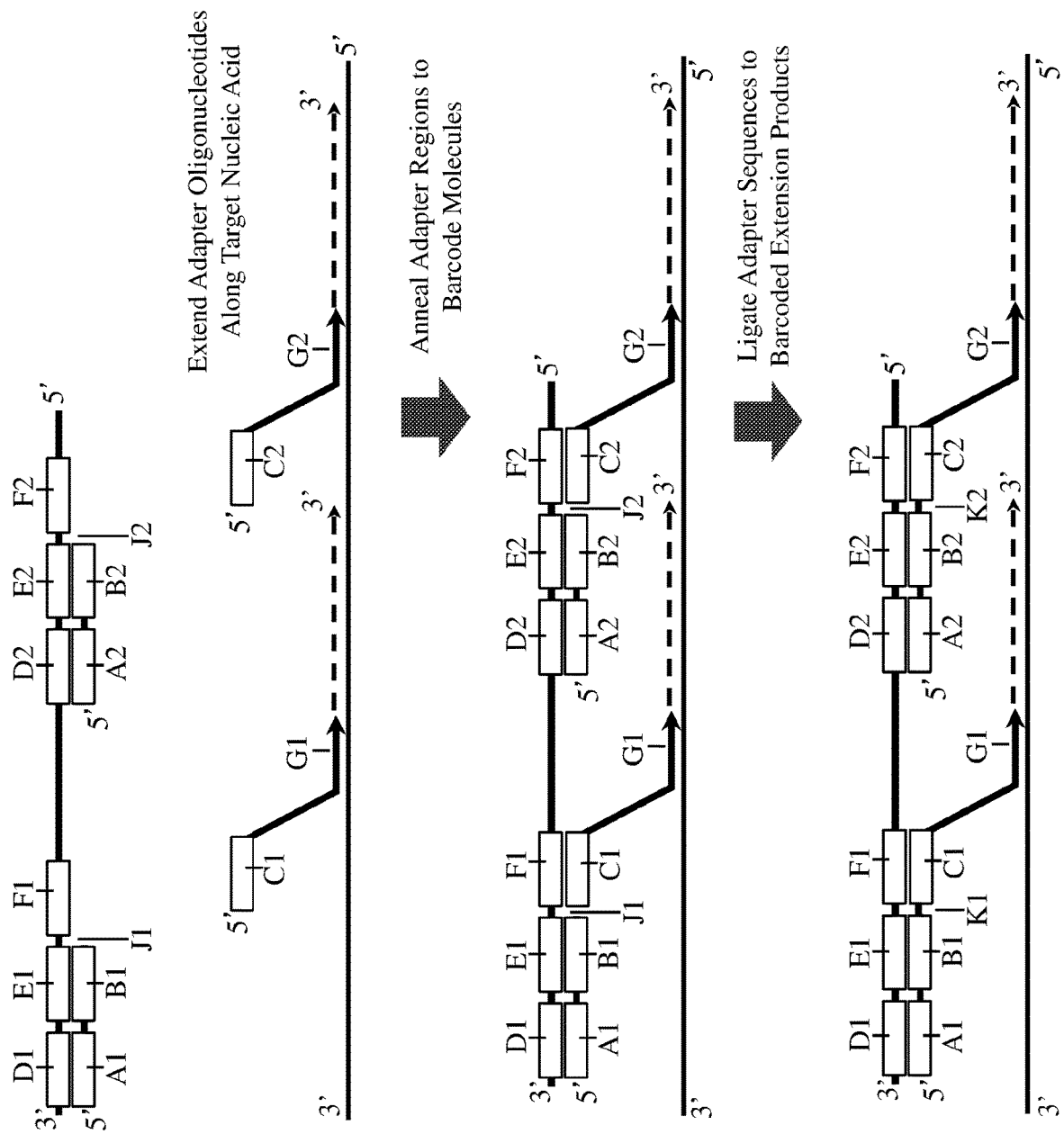
FIG. 12 illustrates a third method of preparing a nucleic acid sample for sequencing using a multimeric barcoding reagent.
Figure 13:
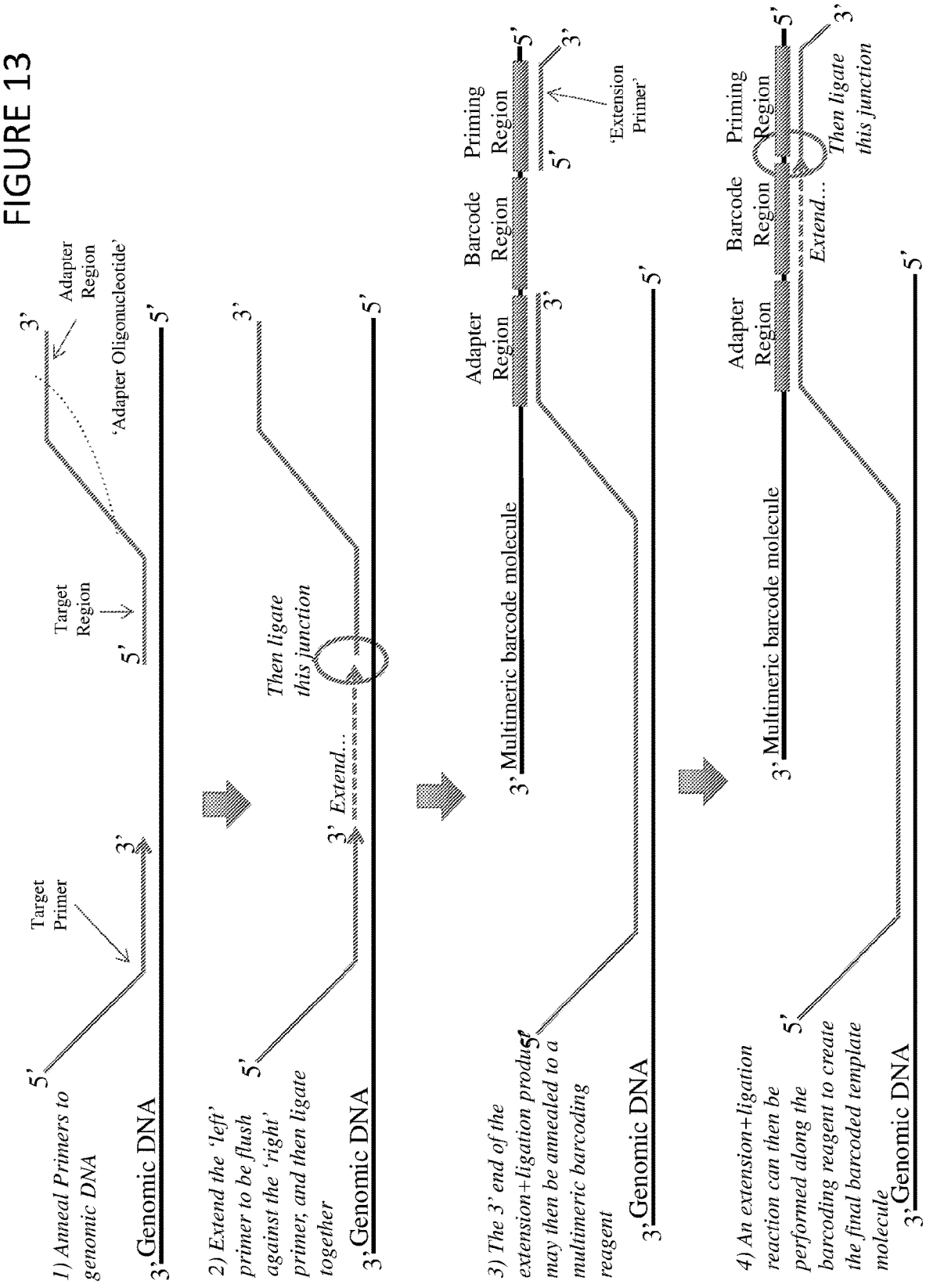
FIG. 13 illustrates a method of preparing a nucleic acid sample for sequencing using a multimeric barcode molecule and adaptor oligonucleotides

Method 1—Synthesis of a Library of Nucleic Acid Barcode Molecules

Synthesis of Double-Stranded Sub-Barcode Molecule Library

In a PCR tube, 10 microliters of 10 micromolar BC_MX3 (an equimolar mixture of all sequences in SEQ ID NO: 18 to 269) were added to 10 microliters of 10 micromolar BC_ADD_TP1 (SEQ ID NO: 1), plus 10 microliters of 10× CutSmart Buffer (New England Biolabs) plus 1.0 microliter of 10 millimolar deoxynucleotide triphosphate nucleotide mix (Invitrogen) plus 68 microliters $H_2O$, to final volume of 99 microliters. The PCR tube was placed on a thermal cycler and incubated at 75° C. for 5 minutes, then slowly annealed to 4° C., then held 4° C., then placed on ice. 1.0 microliter of Klenow polymerase fragment (New England Biolabs; at 5 U/uL) was added to the solution and mixed. The PCR tube was again placed on a thermal cycler and incubated at 25° C. for 15 minutes, then held at 4° C. The solution was then purified with a purification column (Nucleotide Removal Kit; Qiagen), eluted in 50 microliters $H_2O$, and quantitated spectrophotometrically.

Synthesis of Double-Stranded Downstream Adaptor Molecule

In a PCR tube, 0.5 microliters of 100 micromolar BC_ANC_TP1 (SEQ ID NO: 2) were added to 0.5 microliters of 100 micromolar BC_ANC_BT1 (SEQ ID NO: 3), plus 20 microliters of 10× CutSmart Buffer (New England Biolabs) plus 178 microliters $H_2O$, to final volume of 200 microliters. The PCR tube was placed on a thermal cycler and incubated at 95° C. for 5 minutes, then slowly annealed to 4° C., then held 4° C., then placed on ice, then stored at −20° C.

Ligation of Double-Stranded Sub-Barcode Molecule Library to Double-Stranded Downstream Adaptor Molecule In a 1.5 milliliter Eppendorf tube, 1.0 microliter of Double-Stranded Downstream Adaptor Molecule solution was added to 2.5 microliters of Double-Stranded Sub-Barcode Molecule Library, plus 2.0 microliters of 10× T4 DNA Ligase buffer, and 13.5 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters $H_2O$.

PCR Amplification of Ligated Library

In a PCR tube, 2.0 microliters of Ligated Library were added to 2.0 microliters of 50 micromolar BC_FWD_PR1 (SEQ ID NO: 4), plus 2.0 microliters of 50 micromolar BC_REV_PR1 (SEQ ID NO: 5), plus 10 microliters of 10× Taq PCR Buffer (Qiagen) plus 2.0 microliter of 10 millimolar deoxynucleotide triphosphate nucleotide mix (Invitrogen) plus 81.5 microliters $H_2O$, plus 0.5 microliters Qiagen Taq Polymerase (at 5 U/uL) to final volume of 100 microliters. The PCR tube was placed on a thermal cycler and amplified for 15 cycles of: 95° C. for 30 seconds, then 59° C. for 30 seconds, then 72° C. for 30 seconds; then held at 4° C. The solution was then purified with 1.8× volume (180 microliters) Ampure XP Beads (Agencourt; as per manufacturer's instructions), and eluted in 50 microliters $H_2O$.

Uracil Glycosylase Enzyme Digestion

To an eppendorf tube 15 microliters of the eluted PCR amplification, 1.0 microliters $H_2O$, plus 2.0 microliters 10× CutSmart Buffer (New England Biolabs), plus 2.0 microliter of USER enzyme solution (New England Biolabs) was added and mixed. The tube was incubated at 3° C. for 60 minutes, then the solution was purified with 1.8× volume (34 microliters) Ampure XP Beads (Agencourt; as per manufacturer's instructions), and eluted in 34 microliters $H_2O$.

MlyI Restriction Enzyme Cleavage

To the eluate from the previous (glycosylase digestion) step, 4.0 microliters 10× CutSmart Buffer (New England Biolabs), plus 2.0 microliter of MlyI enzyme (New England Biolabs, at 5 U/uL) was added and mixed. The tube was incubated at 3° C. for 60 minutes, then the solution was purified with 1.8× volume (72 microliters) Ampure XP Beads (Agencourt; as per manufacturer's instructions), and eluted in 40 microliters $H_2O$.

Ligation of Sub-Barcode Library to MlyI-Cleaved Solution

In a 1.5 milliliter Eppendorf tube, 10 microliter of MlyI-Cleaved Solution was added to 2.5 microliters of Double-Stranded Sub-Barcode Molecule Library, plus 2.0 microliters of 10× T4 DNA Ligase buffer, and 4.5 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters H$_2$O.

Repeating Cycles of Sub-Barcode Addition

The experimental steps of: 1) Ligation of Sub-Barcode Library to Mlyl-Cleaved Solution, 2) PCR Amplification of Ligated Library, 3) Uracil Glycosylase Enzyme Digestion, and 4) Mlyl Restriction Enzyme Cleavage were repeated, in sequence, for a total of five cycles.

Synthesis of Double-Stranded Upstream Adapter Molecule

In a PCR tube, 1.0 microliters of 100 micromolar BC_USO_TP1 (SEQ ID NO: 6) were added to 1.0 microliters of 100 micromolar BC_USO_BT1 (SEQ ID NO: 7), plus 20 microliters of 10× CutSmart Buffer (New England Biolabs) plus 178 microliters H$_2$O, to final volume of 200 microliters. The PCR tube was placed on a thermal cycler and incubated at 95° C. for 60 seconds, then slowly annealed to 4° C., then held 4° C., then placed on ice, then stored at −20° C.

Ligation of Double-Stranded Upstream Adapter Molecule

In a 1.5 milliliter Eppendorf tube, 3.0 microliters of Upstream Adapter solution were added to 10.0 microliters of final (after the fifth cycle) Mlyl-Cleaved solution, plus 2.0 microliters of 10× T4 DNA Ligase buffer, and 5.0 microliters H$_2$O to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters H$_2$O.

PCR Amplification of Upstream Adapter-Ligated Library

In a PCR tube, 6.0 microliters of Upstream Adapter-Ligated Library were added to 1.0 microliters of 100 micromolar BC_CS_PCR_FWD1 (SEQ ID NO: 8), plus 1.0 microliters of 100 micromolar BC_CS_PCR_REV1 (SEQ ID NO: 9), plus 10 microliters of 10× Taq PCR Buffer (Qiagen) plus 2.0 microliter of 10 millimolar deoxynucleotide triphosphate nucleotide mix (Invitrogen) plus 73.5 microliters H$_2$O, plus 0.5 microliters Qiagen Taq Polymerase (at 5 U/uL) to final volume of 100 microliters. The PCR tube was placed on a thermal cycler and amplified for 15 cycles of: 95° C. for 30 seconds, then 61° C. for 30 seconds, then 72° C. for 30 seconds; then held at 4° C. The solution, containing a library of amplified nucleic acid barcode molecules, was then purified with 1.8× volume (180 microliters) Ampure XP Beads (Agencourt; as per manufacturer's instructions). The library of amplified nucleic acid barcode molecules was then eluted in 40 microliters H$_2$O.

The library of amplified nucleic acid barcode molecules synthesised by the method described above was then used to assemble a library of multimeric barcode molecules as described below.

Method 2—Assembly of a Library of Multimeric Barcode Molecules

A library of multimeric barcode molecules was assembled using the library of nucleic acid barcode molecules synthesised according to the methods of Method 1.

Primer-Extension with Forward Termination Primer and Forward Splinting Primer

In a PCR tube, 5.0 microliters of the library of amplified nucleic acid barcode molecules were added to 1.0 microliters of 100 micromolar CS_SPLT_FWD1 (SEQ ID NO: 10), plus 1.0 microliters of 5 micromolar CS_TERM_FWD1 (SEQ ID NO: 11), plus 10 microliters of 10× Thermopol Buffer (NEB) plus 2.0 microliter of 10 millimolar deoxynucleotide triphosphate nucleotide mix (Invitrogen) plus 80.0 microliters H$_2$O, plus 1.0 microliters Vent Exo-Minus Polymerase (New England Biolabs, at 2 U/uL) to final volume of 100 microliters. The PCR tube was placed on a thermal cycler and amplified for 1 cycle of: 95° C. for 30 seconds, then 53° C. for 30 seconds, then 72° C. for 60 seconds, then 1 cycle of: 95° C. for 30 seconds, then 50° C. for 30 seconds, then 72° C. for 60 seconds, then held at 4° C. The solution was then purified a PCR purification column (Qiagen), and eluted in 85.0 microliters H$_2$O.

Primer-Extension with Reverse Termination Primer and Reverse Splinting Primer

In a PCR tube, the 85.0 microliters of forward-extension primer-extension products were added to 1.0 microliters of 100 micromolar CS_SPLT_REV1 (SEQ ID NO: 12), plus 1.0 microliters of 5 micromolar CS_TERM_REV1 (SEQ ID NO: 13), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 100 microliters. The PCR tube was placed on a thermal cycler and amplified for 1 cycle of: 95° C. for 30 seconds, then 53° C. for 30 seconds, then 72° C. for 60 seconds, then 1 cycle of: 95° C. for 30 seconds, then 50° C. for 30 seconds, then 72° C. for 60 seconds, then held at 4° C. The solution was then purified a PCR purification column (Qiagen), and eluted in 43.0 microliters H$_2$O.

Linking Primer-Extension Products with Overlap-Extension PCR

In a PCR tube were added the 43.0 microliters of reverse-extension primer-extension products, plus 5.0 microliters of 10× Thermopol Buffer (NEB) plus 1.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 50 microliters. The PCR tube was placed on a thermal cycler and amplified for 5 cycles of: 95° C. for 30 seconds, then 60° C. for 60 seconds, then 72° C. for 2 minutes; then 5 cycles of: 95° C. for 30 seconds, then 60° C. for 60 seconds, then 72° C. for 5 minutes; then 5 cycles of: 95° C. for 30 seconds, then 60° C. for 60 seconds, then 72° C. for 10 minutes; then held at 4° C. The solution was then purified with 0.8× volume (80 microliters) Ampure XP Beads (Agencourt; as per manufacturer's instructions), and eluted in 40 microliters H$_2$O.

Amplification of Overlap-Extension Products

In a PCR tube were added 2.0 microliters of Overlap-Extension PCR solution, plus 1.0 microliters of 100 micromolar CS_PCR_FWD1 (SEQ ID NO: 14), plus 1.0 microliters of 100 micromolar CS_PCR_REV1 (SEQ ID NO: 15), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL), plus 83.0 microliters H$_2$O to final volume of 100 microliters. The PCR tube was placed on a thermal cycler and amplified for 15 cycles of: 95° C. for 30 seconds, then 58° C. for 30 seconds, then 72° C. for 10 minutes; then held at 4° C. The solution was then purified with 0.8× volume (80 microliters) Ampure XP Beads (Agencourt; as per manufacturer's instructions), and eluted in 50 microliters H$_2$O, and quantitated spectrophotometrically.

Gel-Based Size Selection of Amplified Overlap-Extension Products

Approximately 250 nanograms of Amplified Overlap-Extension Products were loaded and run on a 0.9% agarose gel, and then stained and visualised with ethidium bromide.

A band corresponding to 1000 nucleotide size (plus and minus 100 nucleotides) was excised and purified with a gel extraction column (Gel Extraction Kit, Qiagen) and eluted in 50 microliters $H_2O$.

Amplification of Overlap-Extension Products

In a PCR tube were added 10.0 microliters of Gel-Size-Selected solution, plus 1.0 microliters of 100 micromolar CS_PCR_FWD1 (SEQ ID NO: 14), plus 1.0 microliters of 100 micromolar CS_PCR_REV1 (SEQ ID NO: 15), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 75.0 microliters $H_2O$ to final volume of 100 microliters. The PCR tube was placed on a thermal cycler and amplified for 15 cycles of: 95° C. for 30 seconds, then 58° C. for 30 seconds, then 72° C. for 4 minutes; then held at 4° C. The solution was then purified with 0.8× volume (80 microliters) Ampure XP Beads (Agencourt; as per manufacturer's instructions), and eluted in 50 microliters $H_2O$, and quantitated spectrophotometrically.

Selection and Amplification of Quantitatively Known Number of Multimeric Barcode Molecules Amplified gel-extracted solution was diluted to a concentration of 1 picogram per microliter, and then to a PCR tube was added 2.0 microliters of this diluted solution (approximately 2 million individual molecules), plus 0.1 microliters of 100 micromolar CS_PCR_FWD1 (SEQ ID NO: 14), plus 0.1 microliters of 100 micromolar CS_PCR_REV1 (SEQ ID NO: 15), plus 1.0 microliter 10× Thermopol Buffer (NEB) plus 0.2 microliter of 10 millimolar deoxynucleotide triphosphate nucleotide mix (Invitrogen), plus 0.1 microliters Vent Exo-Minus Polymerase (New England Biolabs, at 2 U/uL) plus 6.5 microliters $H_2O$ to final volume of 10 microliters. The PCR tube was placed on a thermal cycler and amplified for 11 cycles of: 95° C. for 30 seconds, then 57° C. for 30 seconds, then 72° C. for 4 minutes; then held at 4° C.

To the PCR tube was added 1.0 microliters of 100 micromolar CS_PCR_FWD1 (SEQ ID NO: 14), plus 1.0 microliters of 100 micromolar CS_PCR_REV1 (SEQ ID NO: 15), plus 9.0 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 76.0 microliters $H_2O$ to final volume of 100 microliters. The PCR tube was placed on a thermal cycler and amplified for 10 cycles of: 95° C. for 30 seconds, then 57° C. for 30 seconds, then 72° C. for 4 minutes; then held at 4° C. The solution was then purified with 0.8× volume (80 microliters) Ampure XP Beads (Agencourt; as per manufacturer's instructions), and eluted in 50 microliters $H_2O$, and quantitated spectrophotometrically.

Method 3: Production of Single-Stranded Multimeric Barcode Molecules by In Vitro Transcription and cDNA Synthesis This method describes a series of steps to produce single-stranded DNA strands, to which oligonucleotides may be annealed and then barcoded along. This method begins with four identical reactions performed in parallel, in which a promoter site for the T7 RNA Polymerase is appended to the 5' end of a library of multimeric barcode molecules using an overlap-extension PCR amplification reaction. Four identical reactions are performed in parallel and then merged to increase the quantitative amount and concentration of this product available. In each of four identical PCR tubes, approximately 500 picograms of size-selected and PCR-amplified multimeric barcode molecules (as produced in the 'Selection and Amplification of Quantitatively Known Number of Multimeric Barcode Molecules' step of Method 2) were mixed with 2.0 microliters of 100 micromolar CS_PCR_FWD1_T7 (SEQ ID NO. 270) and 2.0 microliters of 100 micromolar CS_PCR_REV4 (SEQ ID NO. 271), plus 20.0 microliters of 10× Thermopol PCR buffer, plus 4.0 microliters of 10 millimolar deoxynucleotide triphosphate nucleotide mix, and 2.0 microliters Vent Exo Minus polymerse (at 5 units per microliter) plus water to a total volume of 200 microliters. The PCR tube was placed on a thermal cycler and amplified for 22 cycles of: 95° C. for 60 seconds, then 60° C. for 30 seconds, then 72° C. for 3 minutes; then held at 4° C. The solution from all four reactions was then purified with a gel extraction column (Gel Extraction Kit, Qiagen) and eluted in 52 microliters $H_2O$.

Fifty (50) microliters of the eluate was mixed with 10 microliters 10× NEBuffer 2 (NEB), plus 0.5 microliters of 10 millimolar deoxynucleotide triphosphate nucleotide mix, and 1.0 microliters Vent Exo Minus polymerse (at 5 units per microliter) plus water to a total volume of 100 microliters. The reaction was incubated for 15 minutes at room temperature, then purified with 0.8× volume (80 microliters) Ampure XP Beads (Agencourt; as per manufacturer's instructions), and eluted in 40 microliters $H_2O$, and quantitated spectrophotometrically.

A transcription step is then performed, in which the library of FOR-amplified templates containing T7 RNA Polymerase promoter site (as produced in the preceding step) is used as a template for T7 RNA polymerase. This comprises an amplification step to produce a large amount of RNA-based nucleic acid corresponding to the library of multimeric barcode molecules (since each input FOR molecule can serve as a template to produce a large number of cognate RNA molecules). In the subsequent step, these RNA molecules are then reverse transcribed to create the desired, single-stranded multimeric barcode molecules. Ten (10) microliters of the eluate was mixed with 20 microliters 5× Transcription Buffer (Promega), plus 2.0 microliters of 10 millimolar deoxynucleotide triphosphate nucleotide mix, plus 10 microliters of 0.1 milimolar DTT, plus 4.0 microliters SuperAseln (Ambion), and 4.0 microliters Promega T7 RNA Polymerase (at 20 units per microliter) plus water to a total volume of 100 microliters. The reaction was incubated 4 hours at 3° C., then purified with an RNEasy Mini Kit (Qiagen), and eluted in 50 micoliters $H_2O$, and added to 6.0 microliters SuperAseln (Ambion).

The RNA solution produced in the preceding in vitro transcription step is then reverse transcribed (using a primer specific to the 3' ends of the RNA molecules) and then digested with RNAse H to create single-stranded DNA molecules corresponding to multimeric barcode molecules, to which oligonucleotides maybe be annealed and then barcoded along. In two identical replicate tubes, 23.5 microliters of the eluate was mixed with 5.0 microliters of 10 millimolar deoxynucleotide triphosphate nucleotide mix, plus 3.0 microliters SuperAseln (Ambion), and 10.0 microliters of 2.0 micromolar CS_PCR_REV1 (SEQ ID NO. 272) plus water to final volume of 73.5 microliters. The reaction was incubated on a thermal cycler at 65° C. for 5 minutes, then 50° C. for 60 seconds; then held at 4° C. To the tube was added 20 microliters 5× Reverse Transcription buffer (Invitrogen), plus 5.0 microliters of 0.1 milimolar DTT, and 1.75 microliters Superscript III Reverse Transcriptase (Invitrogen). The reaction was incubated at 55° C. for 45 minutes, then 60° C. for 5 minutes; then 70° C. for 15 minutes, then held at 4° C., then purified with a PCR Cleanup column (Qiagen) and eluted in 40 microliters H$_2$O.

Sixty (60) microliters of the eluate was mixed with 7.0 microliters 10× RNAse H Buffer (Promega), plus 4.0 microliters RNAse H (Promega. The reaction was incubated 12 hours at 3° C., then 95° C. for 10 minutes, then held at 4° C., then purified with 0.7× volume (49 microliters) Ampure XP Beads (Agencourt; as per manufacturer's instructions), and eluted in 30 microliters H$_2$O, and quantitated spectrophotometrically.

Method 4: Production of Multimeric Barcoding Reagents Containing Barcoded Oligonucleotides This method describes steps to produce multimeric barcoding reagents from single-stranded multimeric barcode molecules (as produced in Method 3) and appropriate extension primers and adapter oligonucleotides.

In a PCR tube, approximately 45 nanograms of single-stranded RNAse H-digested multimeric barcode molecules (as produced in the last step of Method 3) were mixed with 0.25 microliters of 10 micromolar DS_ST_05 (SEQ ID NO. 273, an adaptor oligonucleotide) and 0.25 microliters of 10 micromolar US_PCR_Prm_Only_03 (SEQ ID NO. 274, an extension primer), plus 5.0 microliters of 5× Isothermal extension/ligation buffer, plus water to final volume of 19.7 microliters. In order to anneal the adapter oligonucleotides and extension primers to the multimeric barcode molecules, in a thermal cycler, the tube was incubated at 98° C. for 60 seconds, then slowly annealed to 55° C., then held at 55° C. for 60 seconds, then slowly annealed to 50° C. then held at 50° C. for 60 seconds, then slowly annealed to 20° C. at 0.1° C./sec, then held at 4° C. To the tube was added 0.3 microliters (0.625 U) Phusion Polymerase (NEB; 2 U/uL) 2.5 microliters (100 U) Taq DNA Ligase (NEB; 40 U/uL); and 2.5 microliters 100 milimolar DTT. In order to extend the extension primer(s) across the adjacent barcode region(s) of each multimeric barcode molecule, and then to ligate this extension product to the phosphorylated 5' end of the adapter oligonucleotide annealed to the downstream thereof, the tube was then incubated at 50° C. for 3 minutes, then held at 4° C. The reaction was then purified with a PCR Cleanup column (Qiagen) and eluted in 30 microliters H$_2$O, and quantitated spectrophotometrically.

Method 5: Production of Synthetic DNA Templates of Known Sequence

This method describes a technique to produce synthetic DNA templates with a large number of tandemly-repeated, co-linear molecular sequence identifiers, by circularizing and then tandemly amplifying (with a processive, strand-displacing polymerase) oligonucleotides containing said molecular sequence identifiers. This reagent may then be used to evaluate and measure the multimeric barcoding reagents described herein.

In a PCR was added 0.4 microliters of 1.0 micromolar Syn_Temp_01 (SEQ ID NO. 275) and 0.4 microliters of 1.0 micromolar ST_Splint_02 (SEQ ID NO. 276) and 10.0 microliters of 10× NEB CutSmart buffer. On a thermal cycler, the tube was incubated at 95° C. for 60 seconds, then held at 75° C. for 5 minutes, then slowly annealed to 20° C. then held at 20° C. for 60 seconds, then held at 4° C. To circularize the molecules through an intramolecular ligation reaction, the tube was then added 10.0 microliters ribo-ATP and 5.0 microliters T4 DNA Ligase (NEB; High Concentration). The tube was then incubated at room temperature for 30 minutes, then at 65° C. for 10 minutes, then slowly annealed to 20° C. then held at 20° C. for 60 seconds, then held at 4° C. To each tube was then added 10× NEB CutSmart buffer, 4.0 microliters of 10 millimolar deoxynucleotide triphosphate nucleotide mix, and 1.5 microliters of diluted phi29 DNA Polymerase (NEB; Diluted 1:20 in 1× CutSmart buffer) plus water to a total volume of 200 microliters. The reaction was incubated at 30° C. for 5 minutes, then held at 4° C., then purified with 0.7× volume (140 microliters) Ampure XP Beads (Agencourt; as per manufacturer's instructions), and eluted in 30 microliters H$_2$O, and quantitated spectrophotometrically.

Method 6: Barcoding Synthetic DNA Templates of Known Sequence with Multimeric Barcoding Reagents Containing Barcoded Oligonucleotides In a PCR tube were added 10.0 microliters 5× Phusion HF buffer (NEB), plus 1.0 microliters 10 millimolar deoxynucleotide triphosphate nucleotide mix, plus 2.0 microliters (10 nanograms) 5.0 nanogram/microliters Synthetic DNA Templates of Known Sequence (as produced by Method 5), plus water to final volume of 42.5 microliters. The tube was then incubated at 98° C. for 60 seconds, then held at 20° C. To the tube was added 5.0 microliters of 5.0 picogram/microliter Multimeric Barcoding Reagents Containing Barcoded Oligonucleotides (as produced by Method 4). The reaction was then incubated at 70° C. for 60 seconds, then slowly annealed to 60° C., then 60° C. for five minutes, then slowly annealed to 55° C., then 55° C. for five minutes, then slowly annealed to 50° C., then 50° C. for five minutes, then held at 4° C. To the reaction was added 0.5 microliters of Phusion Polymerase (NEB), plus 2.0 microliters 10 uM SynTemp_PE2_B1_Short1 (SEQ ID NO. 277, a primer that is complementary to part of the extension products produced by annealing and extending the multimeric barcoding reagents created by Method 4 along the synthetic DNA templates created by Method 5, serves as a primer for the primer-extension and then PCR reactions described in this method). Of this reaction, a volume of 5.0 microliters was added to a new PCR tube, which was then incubated for 30 seconds at 55° C., 30 seconds 60° C., and 30 seconds 72° C., then followed by 10 cycles of: 98° C. then 65° C. then 72° C. for 30 seconds each, then held at 4° C. To each tube was then added 9.0 microliters 5× Phusion buffer, plus 1.0 microliters 10 millimolar deoxynucleotide triphosphate nucleotide mix, plus 1.75 microliters 10 uM SynTemp_PE2_B1_Short1 (SEQ ID NO. 277), plus 1.75 microliters 10 uM US_PCR_Prm_Only_02 (SEQ ID NO. 278, a primer partially complementary to the extension primer employed to generate the multimeric barcoding reagents as per Method 4, and serving as the 'forward' primer in this PCR amplification reaction), plus 0.5 microliters Phusion Polymerase (NEB), plus water to final volume of 50 microliters. The KR tube was placed on a thermal cycler and amplified for 24 cycles of: 98° C. for 30 seconds, then 72° C. for 30 seconds; then held at 4° C., then purified with 1.2× volume (60 microliters) Ampure XP Beads (Agencourt; as per manufacturer's instructions), and eluted in 30 microliters H$_2$O, and quantitated spectrophotometrically.

The resulting library was then barcoded for sample identification by a FOR-based method, amplified, and sequenced by standard methods using a 150-cycle, mid-output NextSeq flowcell (Illumina), and demultiplexed informatically for further analysis.

Method 7: Barcoding Synthetic DNA Templates of Known Sequence with Multimeric Barcoding Reagents and Separate Adaptor Oligonucleotides To anneal and extend adapter oligonucleotides along the synthetic DNA templates, in a PCR tube were added 10.0 microliters 5× Phusion HF buffer (NEB), plus 1.0 microliters 10 millimolar deoxynucleotide triphosphate nucleotide mix, plus 5.0 microliters (25 nanograms) 5.0 nanogram/ microliters Synthetic DNA Templates of Known Sequence (as produced by Method 5), plus 0.25 microliters of 10 micromolar DS_ST_05 (SEQ ID NO. 273), an adaptor oligonucleotide, plus water to final volume of 49.7 microliters. On a thermal cycler, the tube was incubated at 98° C. for 2 minutes, then 63° C. for 1 minute, then slowly annealed to 60° C. then held at 60° C. for 1 minute, then slowly annealed to 57° C. then held at 5° C. for 1 minute, then slowly annealed to 54° C. then held at 54° C. for 1 minute, then slowly annealed to 50° C. then held at 50° C. for 1 minute, then slowly annealed to 45° C. then held at 45° C. for 1 minute, then slowly annealed to 40° C. then held at 40° C. for 1 minute, then held at 4° C. To the tube was added 0.3 microliters Phusion Polymerase (NEB), and the reaction was incubated at 45° C. for 20 seconds, then 50° C. for 20 seconds, then 55° C. for 20 seconds, 60° C. for 20 seconds, then 72° C. for 20 seconds, then held at 4° C.; the reaction was then purified with 0.8× volume (40 microliters) Ampure XP Beads (Agencourt; as per manufacturer's instructions), and eluted in 30 microliters H$_2$O, and quantitated spectrophotometrically.

In order to anneal adapter oligonucleotides (annealed and extended along the synthetic DNA templates as in the previous step) to multimeric barcode molecules, and then to anneal and then extend extension primer(s) across the adjacent barcode region(s) of each multimeric barcode molecule, and then to ligate this extension product to the phosphorylated 5' end of the adapter oligonucleotide annealed to the downstream thereof, to a PCR tube was added 10 microliters of the eluate from the previous step (containing the synthetic DNA templates along which the adapter oligonucleotides have been annealed and extended), plus 3.0 microliters of a 50.0 nanomolar solution of RNAse H-digested multimeric barcode molecules (as produced in the last step of Method 3), plus 6.0 microliters of 5× Isothermal extension/ligation buffer, plus water to final volume of 26.6 microliters. On a thermal cycler, the tube was incubated at 70° C. for 60 seconds, then slowly annealed to 60° C., then held at 60° C. for 5 minutes, then slowly annealed to 55° C. then held at 55° C. for 5 minutes, then slowly annealed to 50° C. at 0.1° C./sec then held at 50° C. for 30 minutes, then held at 4° C. To the tube was added 0.6 microliters 10 uM US_PCR_Prm_Only_02 (SEQ ID NO: 278, an extension primer), and the reaction was incubated at 50° C. for 10 minutes, then held at 4° C. To the tube was added 0.3 microliters (0.625 U) Phusion Polymerase (NEB; 2 U/uL) 2.5 microliters (100 U) Taq DNA Ligase (NEB; 40 U/uL); and 2.5 microliters 100 milimolar DTT. The tube was then incubated at 50° C. for 5 minutes, then held at 4° C. The reaction was then purified with 0.7× volume (21 microliters) Ampure XP Beads (Agencourt; as per manufacturer's instructions), and eluted in 30 microliters H$_2$O, and quantitated spectrophotometrically.

To a new PCR tube was add 25.0 microliters of the eluate, plus 10.0 microliters 5× Phusion HF buffer (NEB), plus 1.0 microliters 10 millimolar deoxynucleotide triphosphate nucleotide mix, plus 2.0 microliters 10 uM SynTemp_PE2_B1_Short1 (SEQ ID NO: 277; a primer that is complementary to part of the extension products produced by the above steps; serves as a primer for the primer-extension and then PCR reactions described here), plus 0.5 uL Phusion Polymerase (NEB), plus water to final volume of 49.7 microliters. Of this reaction, a volume of 5.0 microliters was added to a new PCR tube, which was then incubated for 30 seconds at 55° C., 30 seconds 60° C., and 30 seconds 72° C., then followed by 10 cycles of: 98° C. then 65° C. then 72° C. for 30 seconds each, then held at 4° C. To each tube was then added 9.0 microliters 5× Phusion buffer, plus 1.0 microliters 10 millimolar deoxynucleotide triphosphate nucleotide mix, plus 1.75 microliters 10 uM SynTemp_PE2_B1_Short1 (SEQ ID NO: 277), plus 1.75 microliters 10 uM US_PCR_Prm_Only_02 (SEQ ID NO: 278), plus 0.5 microliters Phusion Polymerase (NEB), plus water to final volume of 50 microliters. The PCR tube was placed on a thermal cycler and amplified for 24 cycles of: 98° C. for 30 seconds, then 72° C. for 30 seconds; then held at 4° C., then purified with 1.2× volume (60 microliters) Ampure XP Beads (Agencourt; as per manufacturer's instructions), and eluted in 30 microliters H$_2$O, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 9: Barcoding Genomic DNA Loci with Multimeric Barcoding Reagents Containing Barcoded Oligonucleotides This method describes a framework for barcoding targets within specific genomic loci (e.g. barcoding a number of exons within a specific gene) using multimeric barcoding reagents that contain barcoded oligonucleotides. First, a solution of Multimeric Barcode Molecules was produced by In Vitro Transcription and cDNA Synthesis (as described in Method 3). Then, solutions of multimeric barcoding reagents containing barcoded oligonucleotides was produced as described in Method 4, with a modification made such that instead of using an adaptor oligonucleotide targeting a synthetic DNA template (i.e. DS_ST_05, SEQ ID NO: 273, as used in Method 4), adaptor oligonucleotides targeting the specific genomic loci were included at that step. Specifically, a solution of multimeric barcoding reagents containing appropriate barcoded oligonucleotides was produced individually for each of three different human genes: BRCA1 (containing 7 adaptor oligonucleotides, SEQ ID NOs 279-285), HLA-A (containing 3 adapter oligonucleotides, SEQ ID NOs 286-288), and DQB1 (containing 2 adaptor oligonucleotides, SEQ ID NOs 289-290). The process of Method 4 was conducted for each of these three solutions as described above. These three solutions were then merged together, in equal volume, and diluted to a final, total concentration all barcoded oligonucleotides of approximately 50 nanomolar.

In a PCR tube were plus 2.0 microliters 5× Phusion HF buffer (NEB), plus 1.0 microliter of 100 nanogram/microliter human genomic DNA (NA12878 from Coriell Institute) to final volume of 9.0 microliters. In certain variant versions of this protocol, the multimeric barcoding reagents (containing barcoded oligonucleotides) were also added at this step, prior to the high-temperature 98° C. incubation. The reaction was incubated at 98° C. for 120 seconds, then held at 4° C. To the tube was added 1.0 microliters of the above 50 nanomolar solution of multimeric barcode reagents, and then the reaction was incubated for 1 hour at 55° C., then 1 hour at 50° C., then 1 hour at 45° C., then held at 4° C. (Note that for certain samples, this last annealing process was extended to occur overnight, for a total of approximately 4 hours per temperature step).

In order to add a reverse universal priming sequence to each amplicon sequence (and thus to enable subsequent amplification of the entire library at once, using just one forward and one reverse amplification primer), the reaction was diluted 1:100, and 1.0 microliter of the resulting solution was added in a new PCR tube to 20.0 microliters 5× Phusion HF buffer (NEB), plus 2.0 microliters 10 millimolar deoxynucleotide triphosphate nucleotide mix, plus 1.0 microliters a reverse-primer mixture (equimolar concentration of SEQ ID Nos 291-303, each primer at 5 micromolar concentration), plus 1.0 uL Phusion Polymerase (NEB), plus water to final volume of 100 microliters. The reaction was incubated at 53° C. for 30 seconds, 72° C. for 45 seconds, 98° C. for 90 seconds, then 68° C. for 30 seconds, then 64° C. for 30 seconds, then 72° C. for 30 seconds: then held at 4° C. The reaction was then purified with 0.8× volume (80 microliters) Ampure XP Beads (Agencourt; as per manufacturer's instructions), and eluted in 30 microliters H$_2$O, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 10—Sequencing the Library of Multimeric Barcode Molecules

Preparing Amplified Selected Molecules for Assessment with High-Throughput Sequencing To a PCR tube was added 1.0 microliters of the amplified selected molecule solution, plus 1.0 microliters of 100 micromolar CS_SQ_AMP_REV1 (SEQ ID NO: 16), plus 1.0 microliters of 100 micromolar US_PCR_Prm_Only_02 (SEQ ID NO: 17), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 84.0 microliters H$_2$O to final volume of 100 microliters. The PCR tube was placed on a thermal cycler and amplified for 3 cycles of: 95° C. for 30 seconds, then 56° C. for 30 seconds, then 72° C. for 3 minutes; then held at 4° C. The solution was then purified with 0.8× volume (80 microliters) Ampure XP Beads (Agencourt; as per manufacturer's instructions), and eluted in 85 microliters H$_2$O.

This solution was then added to a new PCR tube, plus 1.0 microliters of 100 micromolar Illumina_PE1, plus 1.0 microliters of 100 micromolar Illumina_PE2, plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 100 microliters. The PCR tube was placed on a thermal cycler and amplified for 4 cycles of: 95° C. for 30 seconds, then 64° C. for 30 seconds, then 72° C. for 3 minutes; then 18 cycles of: 95° C. for 30 seconds, then 67° C. for 30 seconds, then 72° C. for 3 minutes; then held at 4° C. The solution was then purified with 0.8× volume (80 microliters) Ampure XP Beads (Agencourt; as per manufacturer's instructions), and eluted in 40 microliters H$_2$O.

High-throughput Illumina sequencing was then performed on this sample using a MiSeq sequencer with paired-end, 250-cycle V2 sequencing chemistry.

Figure 21:
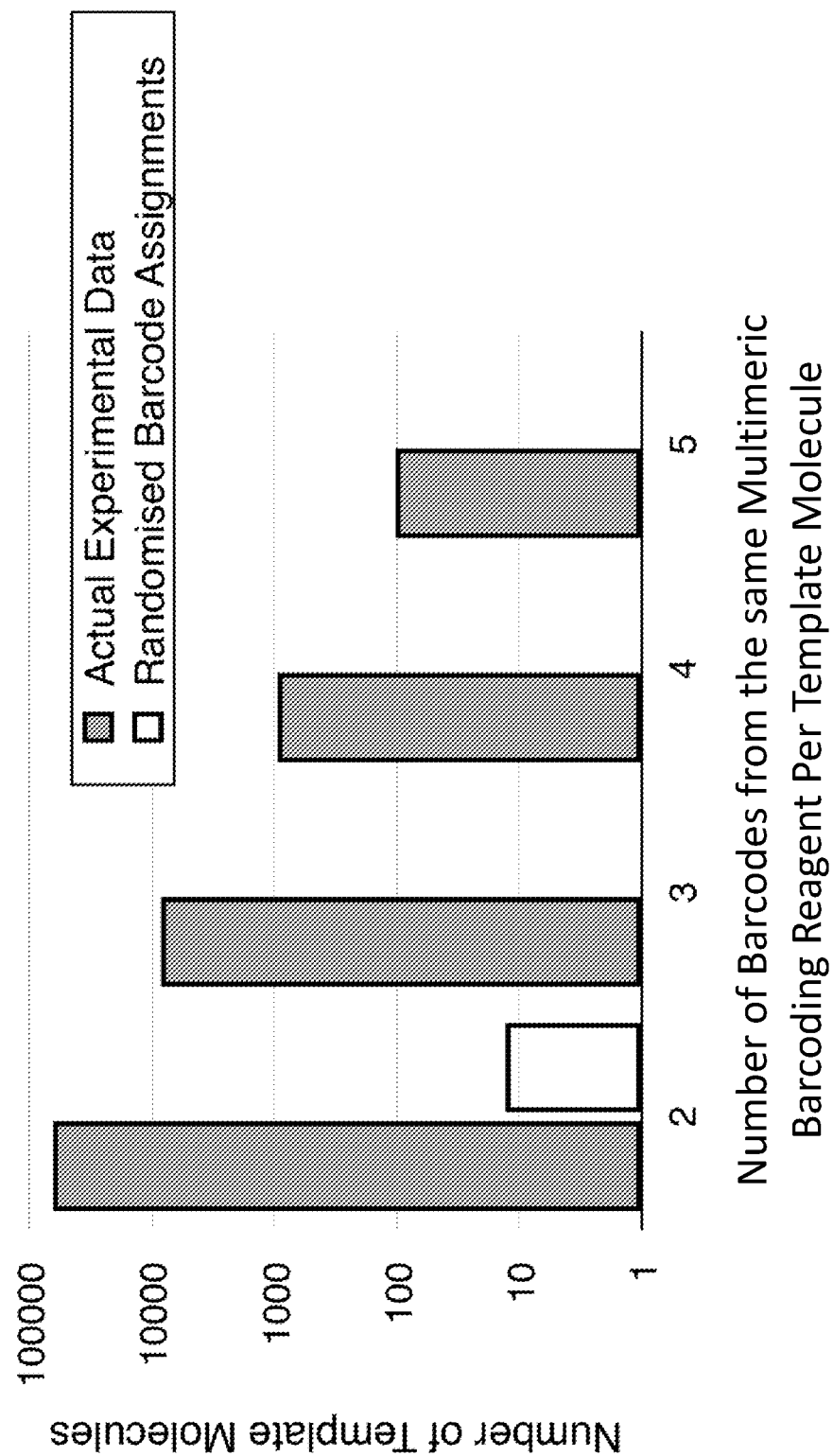
FIG. 21 is a graph showing the number of barcodes from the same multimeric barcoding reagent that labelled sequences on the same synthetic template molecule against the number of synthetic template molecules

Method 11—Assessment of Multimeric Nature of Barcodes Annealed and Extended Along Single Synthetic Template DNA Molecules A library of barcoded synthetic DNA templates was created using a solution of multimeric barcoding reagents produced according to a protocol as described generally in Method 3 and Method 4, and using a solution of synthetic DNA templates as described in Method 5, and using a laboratory protocol as described in Method 6; the resulting library was then barcoded for sample identification by a PCR-based method, amplified, and sequenced by standard methods using a 150-cycle, mid-output NextSeq flowcell (Illumina), and demultiplexed informatically for further analysis. The DNA sequencing results from this method were then compared informatically with data produced from Method 10 to assess the degree of overlap between the multimeric barcoding of synthetic DNA templates and the arrangement of said barcodes on individual multimeric barcoding reagents (the results are shown in FIG. 21).

Results

Structure and Expected Sequence Content of Each Sequence Multimeric Barcoding Reagent Molecule The library of multimeric barcode molecules synthesised as described in Methods 1 to 3 was prepared for high-throughput sequencing, wherein each molecule sequenced includes a contiguous span of a specific multimeric barcode molecule (including one or more barcode sequences, and one or more associate upstream adapter sequences and/or downstream adapter sequences), all co-linear within the sequenced molecule. This library was then sequenced with paired-end 250 nucleotide reads on a MiSeq sequencer (Illumina) as described. This yielded approximately 13.5 million total molecules sequenced from the library, sequenced once from each end, for a total of approximately 27 million sequence reads.

Each forward read is expected to start with a six nucleotide sequence, corresponding to the 3' end of the upstream adapter: TGACCT This forward read is followed by the first barcode sequence within the molecule (expected to be 20 nt long).

This barcode is then followed by an 'intra-barcode sequence' (in this case being sequenced in the 'forward' direction (which is 82 nucleotides including both the downstream adapter sequence and upstream adapter sequence in series):

ATACCTGACTGCTCGTCAGTTGAGCGAATTCCGTATGGTGGTACACACCT

ACACTACTCGGACGCTCTTCCGATCTTGACCT

Within the 250 nucleotide forward read, this will then be followed by a second barcode, another intra-barcode sequence, and then a third barcode, and then a fraction of another intra-barcode sequence.

Each reverse read is expected to start with a sequence corresponding to the downstream adapter sequence; GCTCAACTGACGAGCAGTCAGGTAT This reverse read is then followed by the first barcode coming in from the opposite end of the molecule (also 20 nucleotides long, but sequenced from the opposite strand of the molecule and thus of the inverse orientation to those sequenced by the forward read) This barcode is then followed by the 'intra-barcode sequence' but in the inverse orientation (as it is on the opposite strand):

AGGTCAAGATCGGAAGAGCGTCCGAGTAGTGTAGGTGTGTACCACCATAC

GGAATTCGCTCAACTGACGAGCAGTCAGGTAT

Likewise this 250 nucleotide reverse read will then be followed by a second barcode, another intra-barcode sequence, and then a third barcode, and then a fraction of another intra-barcode sequence.

Sequence Extraction and Analysis

With scripting in Python, each associated pair of barcode and flanking upstream-adapter and downstream-adapter sequence were isolated, with each individual barcode sequence of each barcode molecule then isolated, and each barcode sequence that was sequenced within the same molecule being annotated as belonging to the same multimeric barcode molecule in the library of multimeric barcode molecules. A simple analysis script (Networkx; Python) was employed to determine overall multimeric barcode molecule barcode groups, by examining overlap of barcode-barcode pairs across different sequenced molecules. Several metrics of this data were made, including barcode length, sequence content, and the size and complexity of the multimeric barcode molecules across the library of multimeric barcode molecules.

Number of Nucleotides within Each Barcode Sequence

Figure 14:
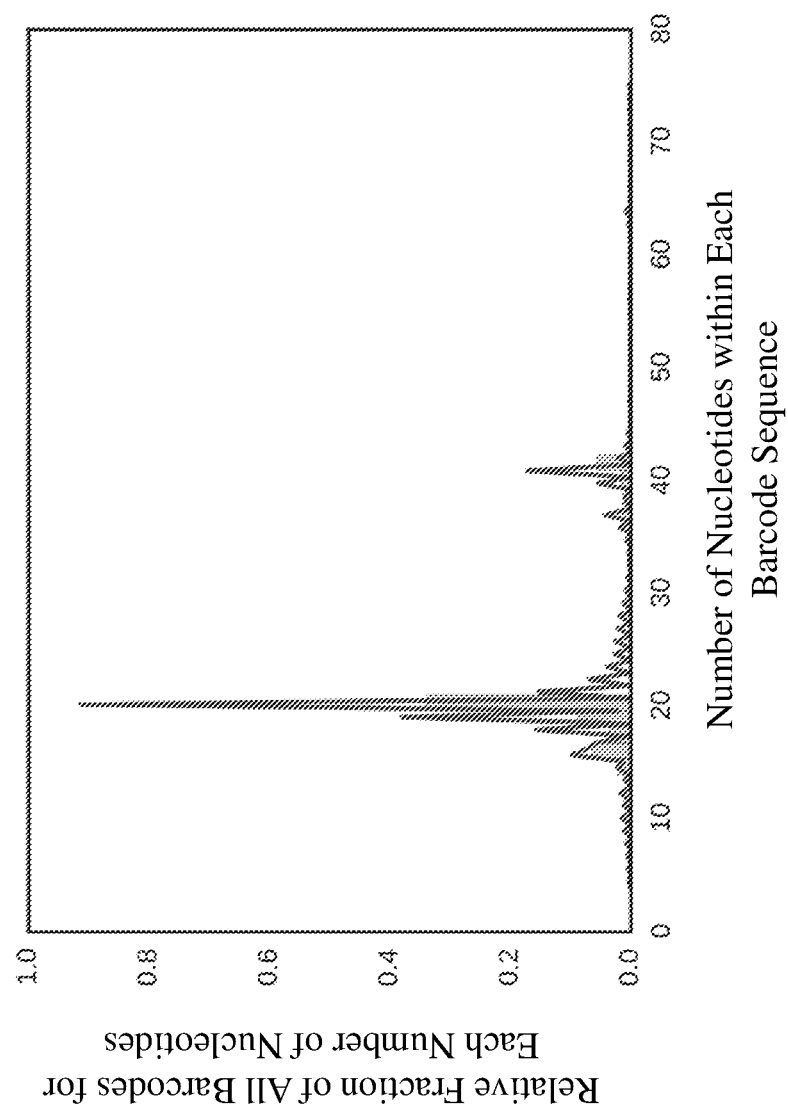
FIG. 14 is a graph showing the total number of nucleotides within each barcode sequence.

Each individual barcode sequence from each barcode molecule, contained within each Illumina-sequenced molecule was isolated, and the total length of each such barcode was determined by counting the number of nucleotides between the upstream adapter molecule sequence, and the downstream adapter molecule sequence. The results are shown in FIG. 14.

The overwhelming majority of barcodes are 20 nucleotides long, which corresponds to five additions of our four-nucleotide-long sub-barcode molecules from our double-stranded sub-barcode library. This is thus the expected and desired result, and indicates that each 'cycle' of: Ligation of Sub-Barcode Library to MlyI-Cleaved Solution, PCR Amplification of the Ligated Library, Uracil Glycosylase Enzyme Digestion, and MlyI Restriction Enzyme Cleavage, was successful and able to efficiently add new four-nucleotide sub-barcode molecules at each cycle, and then was successfully able to amplify and carry these molecules forward through the protocol for continued further processing, including through the five total cycles of sub-barcode addition, to make the final, upstream-adapter-ligated libraries.

We also used this sequence analysis method to quantitate the total number of unique barcodes in total, across all sequenced multimeric barcode molecules: this amounted to 19,953,626 total unique barcodes, which is essentially identical to the 20 million barcodes that would be expected, given that we synthesised 2 million multimeric barcode molecules, each with approximately 10 individual barcode molecules.

Together, this data and analysis thus shows that the methods of creating complex, combinatoric barcodes from sub-barcode sequences is effective and useful for the purpose of synthesising multimeric barcode molecules.

Total Number of Unique Barcode Molecules in Each Multimeric Barcode Molecule

Figure 15:
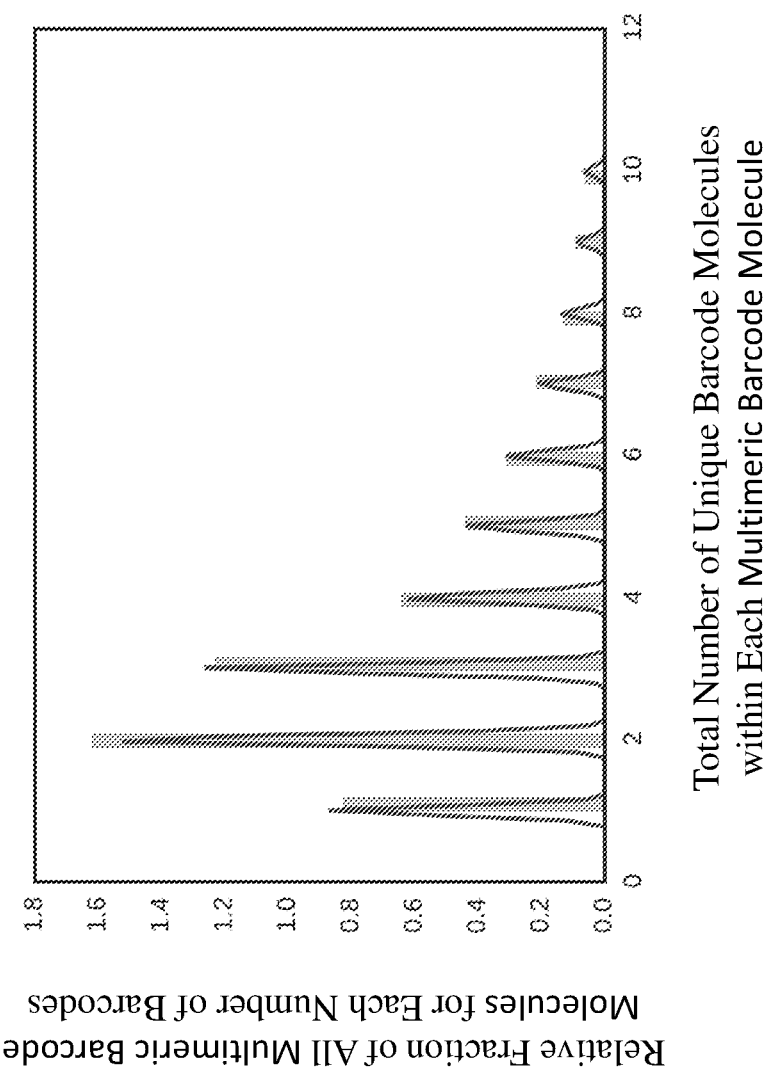
FIG. 15 is a graph showing the total number of unique barcode molecules in each sequenced multimeric barcode molecule.

FIG. 15 shows the results of the quantification of the total number of unique barcode molecules (as determined by their respective barcode sequences) in each sequenced multimeric barcode molecule. As described above, to do this we examined, in the first case, barcode sequences which were present and detected within the same individual molecules sequenced on the sequencer. We then employed an additional step of clustering barcode sequences further, wherein we employed a simple network analysis script (Networkx) which can determine links between individual barcode sequences based both upon explicit knowledge of links (wherein the barcodes are found within the same, contiguous sequenced molecule), and can also determine 'implicit' links, wherein two or more barcodes, which are not sequenced within the same sequenced molecule, instead both share a direct link to a common, third barcode sequence (this shared, common link thus dictating that the two first barcode sequences are in fact located on the same multimeric barcode molecule).

This figure shows that the majority of multimeric barcode molecules sequenced within our reaction have two or more unique barcodes contained therein, thus showing that, through our Overlap-Extension PCR linking process, we are able to link together multiple barcode molecules into multimeric barcode molecules. Whilst we would expect to see more multimeric barcode molecules exhibiting closer to the expected number of barcode molecules (10), we expect that this observed effect is due to insufficiently high sequencing depth, and that with a greater number of sequenced molecules, we would be able to observe a greater fraction of the true links between individual barcode molecules. This data nonetheless suggest that the fundamental synthesis procedure we describe here is efficacious for the intended purpose.

Representative Multimeric Barcode Molecules

Figure 16:
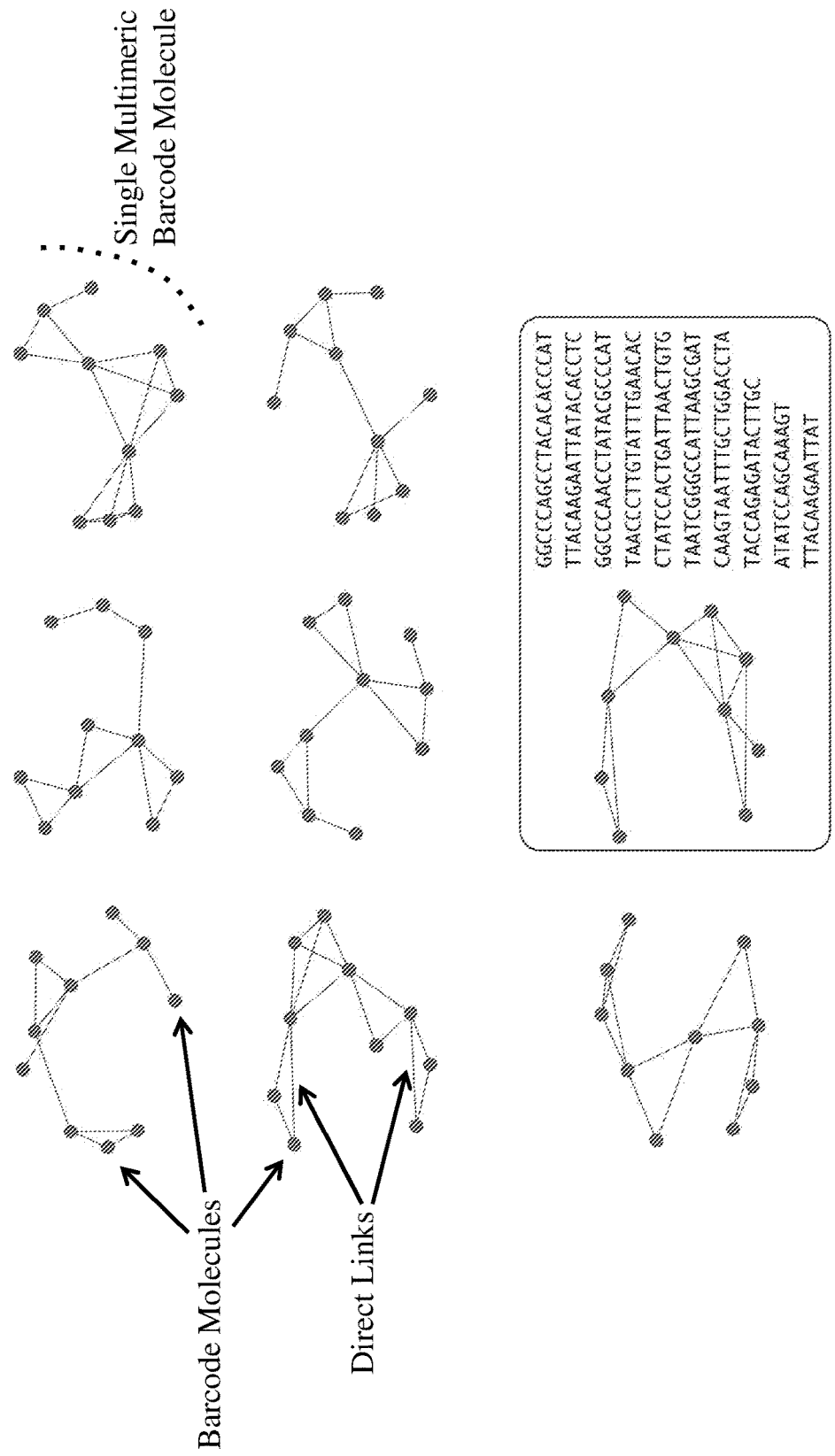
FIG. 16 shows representative multimeric barcode molecules that were detected by the analysis script.

FIG. 16 shows representative multimeric barcode molecules that have been detected by our analysis script. In this figure, each 'node' is a single barcode molecule (from its associated barcode sequence), each line is a 'direct link' between two barcode molecules that have been sequenced at least once in the same sequenced molecule, and each cluster of nodes is an individual multimeric barcode molecule, containing both barcodes with direct links and those within implicit, indirect links as determined by our analysis script. The inset figure includes a single multimeric barcode molecule, and the sequences of its constituent barcode molecules contained therein.

This figure illustrates the our multimeric barcode molecule synthesis procedure: that we are able to construct barcode molecules from sub-barcode molecule libraries, that we are able to link multiple barcode molecules with an overlap-extension PCR reaction, that we are able to isolate a quantitatively known number of individual multimeric barcode molecules, and that we are able to amplify these and subject them to downstream analysis and use.

Barcoding Synthetic DNA Templates of Known Sequence with (i) Multimeric Barcoding Reagents Containing Barcoded Oligonucleotides, and (ii) Multimeric Barcoding Reagents and Separate Adaptor Oligonucleotides Sequence Extraction and Analysis With scripting in Python and implemented in an Amazon Web Services (AWS) framework, for each sequence read following sample-demultiplexing, each barcode region from the given multimeric barcode reagent was isolated from its flanking upstream-adapter and downstream-adapter sequence. Likewise, each molecular sequence identifier region from the given synthetic DNA template molecule was isolated from its flanking upstream and downstream sequences. This process was repeated for each molecule in the sample library; a single filtering step was performed in which individual barcodes and molecular sequence identifiers that were present in only a single read (thus likely to represent either sequencing error or error from the enzymatic sample-preparation process) were censored from the data. For each molecular sequence identifier, the total number of unique (ie with different sequences) barcode regions found associated therewith within single sequence reads was quantitated. A histogram plot was then created to visualize the distribution of this number across all molecular sequence identifiers found in the library.

DISCUSSION

Figure 17:
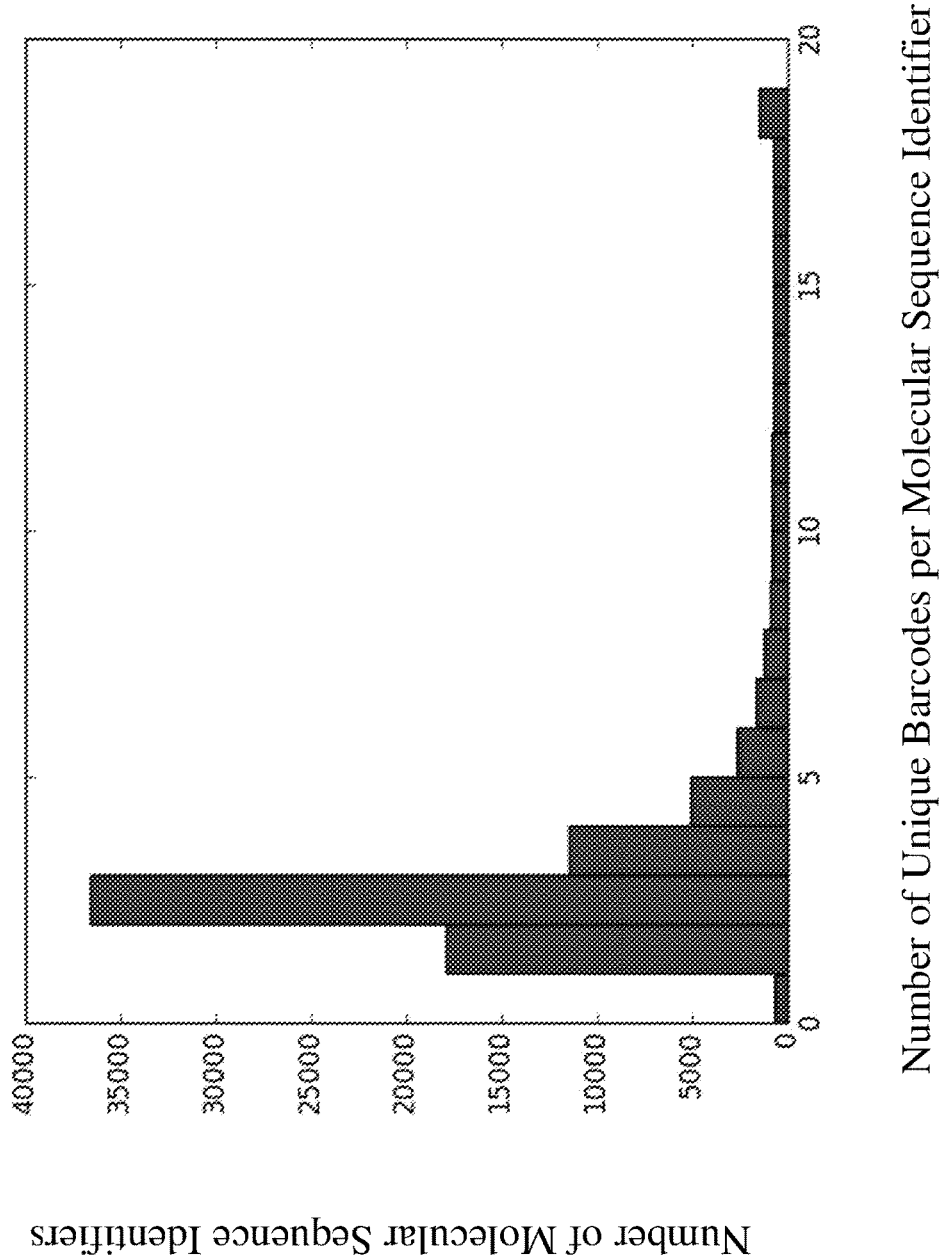
FIG. 17 is a graph showing the number of unique barcodes per molecular sequence identifier against the number of molecular sequence identifiers following the barcoding of synthetic DNA templates of known sequence with multimeric barcoding reagents containing barcoded oligonucleotides.

FIG. 17 shows the results of this analysis for Method 6 (Barcoding Synthetic DNA Templates of Known Sequence with Multimeric Barcoding Reagents Containing Barcoded Oligonucleotides). This figure makes clear that the majority of multimeric barcoding reagents are able to successfully label two or more of the tandemly-repeated copies of each molecular sequence identifier with which they are associated. A distribution from 1 to approximately 5 or 6 'labelling events' is observed, indicating that there may be a degree of stochastic interactions that occur with this system, perhaps due to incomplete enzymatic reactions, or steric hindrance at barcode reagent/synthetic template interface, or other factors.

Figure 18:
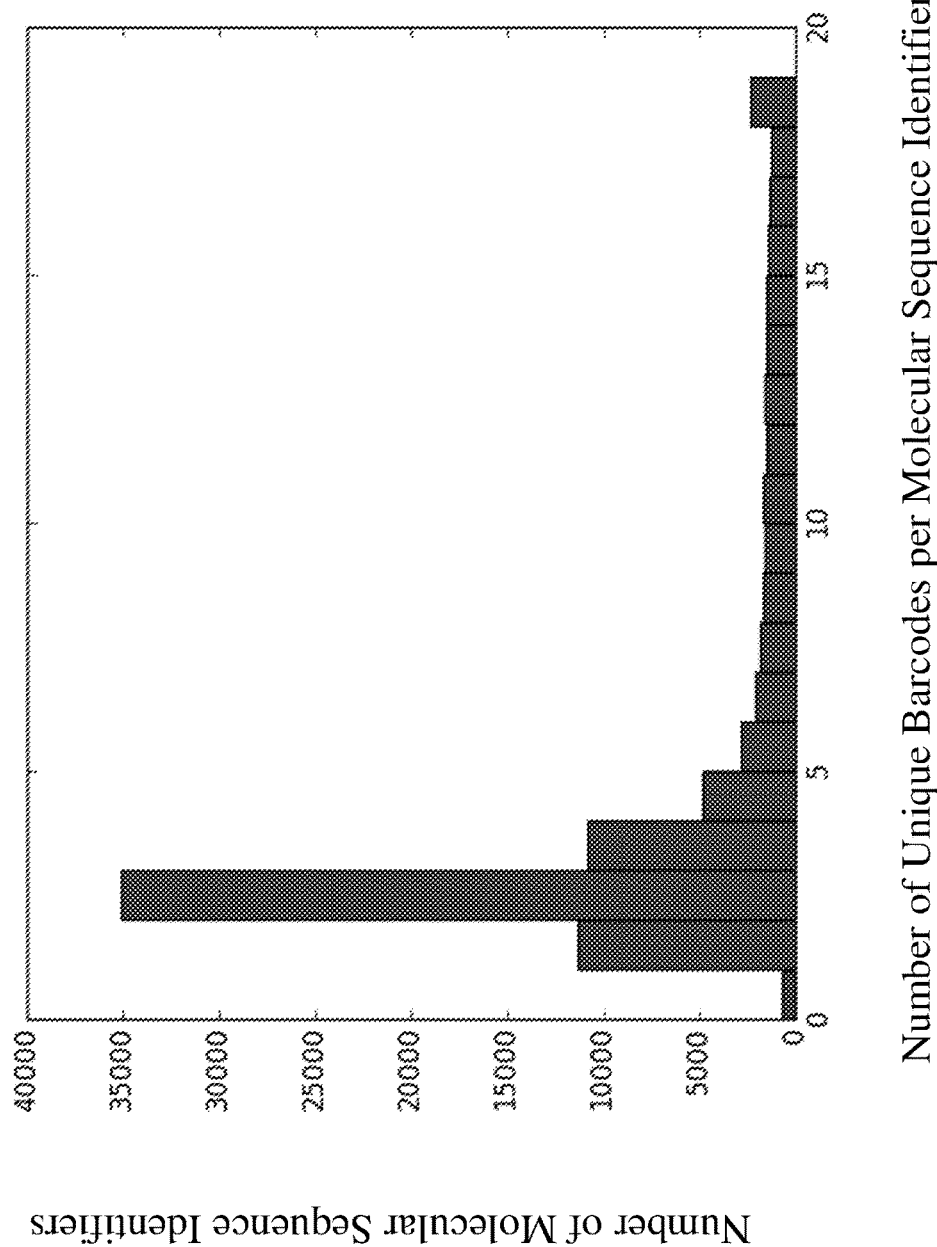
FIG. 18 is a graph showing the number of unique barcodes per molecular sequence identifier against the number of molecular sequence identifiers following the barcoding of synthetic DNA templates of known sequence with multimeric barcoding reagents and separate adaptor oligonucleotides.

FIG. 18 shows the results of this same analysis conducted using Method 7 (Barcoding Oligonucleoitdes Synthetic DNA Templates of Known Sequence with Multimeric Barcode Molecules and Separate Adaptor Oligonucleotides). This figure also clearly shows that the majority of multimeric barcoding reagents are able to successfully label two or more of the tandemly-repeated copies of each molecular sequence identifier with which they are associated, with a similar distribution to that observed for the previous analysis.

Together, these two figures show that this framework for multimeric molecular barcoding is an effective one, and furthermore that the framework can be configured in different methodologic ways. FIG. 17 shows results based on a method in which the framework is configured such that the multimeric barcode reagents already contain barcoded oligonucleotides, prior to their being contacted with a target (synthetic) DNA template. In contrast, FIG. 18 shows results based on an alternative method in which the adaptor oligonucleotides first contact the synthetic DNA template, and then in a subsequent step the adaptor oligonucleotides are barcoded through contact with a multimeric barcode reagent. Together these figures demonstrate both the multimeric barcoding ability of these reagents, and their versatility in different key laboratory protocols.

To analyse whether, and the extent to which, individual multimeric barcoding reagents successfully label two or more sub-sequences of the same synthetic DNA template, the groups of different barcodes on each individual multimeric barcoding reagent in the library (as predicted from the Networkx analysis described in the preceding paragraph and as illustrated in FIG. 16) was compared with the barcodes annealed and extended along single synthetic DNA templates (as described in Method 11). Each group of barcodes found on individual multimeric barcoding reagents was given a numeric 'reagent identifier label'. For each synthetic DNA template molecular sequence identifier (i.e., for each individual synthetic DNA template molecule) that was represented in the sequencing data of Method 11 by two or more barcodes (i.e., wherein two or more sub-sequences of the synthetic template molecule were annealed and extended by a barcoded oligonucleotide), the corresponding 'reagent identifier label' was determined. For each such synthetic template molecule, the total number of multimeric barcodes coming from the same, single multimeric barcoding reagent was then calculated (i.e., the number of different sub-sequences in the synthetic template molecule that were labeled by a different barcoded oligonucleotide but from the same, single multimeric barcoding reagent was calculated). This analysis was then repeated and compared with a 'negative control' condition, in which the barcodes assigned to each 'reagent identifier label' were randomized (i.e. the same barcode sequences remain present in the data, but they no longer correspond to the actual molecular linkage of different barcode sequences across the library of multimeric barcoding reagents).

The data from this analysis is shown in FIG. 21, for both the actual experimental data and for the control data with randomized barcode assignments (note the logarithmic scale of the vertical axis). As this figure shows, though the number of unique barcoding events per target synthetic DNA template molecule is small, they overlap almost perfectly with the known barcode content of individual multimeric barcoding reagents. That is, when compared with the randomized barcode data (which contains essentially no template molecules that appear to be 'multivalently barcoded'), the overwhelming majority (over 99.9%) of template molecules in the actual experiment that appear to be labeled by multiple barcoded oligonucleotides from the same, individual multimeric barcoding reagent, are in fact labeled multiply by the same, single reagents in solution. By contrast, if there were no non-random association between the different barcodes that labelled individual synthetic DNA templates (that is, if FIG. 21 showed no difference between the actual experimental data and the randomized data), then this would have indicated that the barcoding had not occurred in a spatially-constrained manner as directed by the multimeric barcoding reagents. However, as explained above, the data indicates convincingly that the desired barcoding reactions did occur, in which sub-sequences found on single synthetic DNA templates interacted with (and were then barcoded by) only single, individual multimeric barcoding reagents.

Figure 20:
FIG. 20 is a schematic illustration of a sequence read obtained from barcoding genomic DNA loci with multimeric barcoding reagents containing barcoded oligonucleotides.

Barcoding Genomic DNA Loci with Multimeric Barcoding Reagents Containing Barcoded Oligonucleotides Sequence Extraction and Analysis As with other analysis, scripting was composed in Python and implemented in an Amazon Web Services (AWS) framework. For each sequence read following sample-demultiplexing, each barcode region from the given multimeric barcode reagent was isolated from its flanking upstream-adapter and downstream-adapter sequence and recorded independently for further analysis. Likewise, each sequence to the 3' end of the downstream region (representing sequence containing the barcoded oligonucleotide, and any sequences that the oligonucleotide had primed along during the experimental protocol) was isolated for further analysis. Each downstream sequence of each read was analysed for the presence of expected adaptor oligonucleotide sequences (i.e. from the primers corresponding to one of the three genes to which the oligonucleotides were directed) and relevant additional downstream sequences. Each read was then recorded as being either 'on-target' (with sequence corresponding to one of the expected, targeted sequence) or 'off-target'. Furthermore, for each of the targeted regions, the total number of unique multimeric barcodes (i.e. with identical but duplicate barcodes merged into a single-copy representation) was calculated. A schematic of each expected sequence read, and the constituent components thereof, is shown in FIG. 20.

DISCUSSION

FIG. 19 shows the results of this analysis for this method, for four different independent samples. These four samples represent a method wherein the process of annealing the multimeric barcode reagents took place for either 3 hours, or overnight (approximately 12 hours). Further, for each of these two conditions, the method was performed either with the multimeric barcode reagents retained intact as originally synthesized, or with a modified protocol in which the barcode oligonucleotides are first denatured away from the barcode molecules themselves (through a high-temperature melting step). Each row represents a different amplicon target as indicated, and each cell represents the total number of unique barcode found associated with each amplicon in each of the four samples. Also listed is the total proportion of on-target reads, across all targets summed together, for each sample.

As seen in the figure, the majority of reads across all samples are on-target; however there is seen a large range in the number of unique barcode molecules observed for each amplicon target. These trends across different amplicons seem to be consistent across the different experimental conditions, and could be due to different priming (or mis-priming) efficiencies of the different oligonucleotides, or different amplification efficiencies, or different mapping efficiencies, plus potential other factors acting independently or in combination. Furthermore, it is clear that the samples that were annealed for longer have a larger number of barcodes observed, likely due to more complete overall annealing of the multimeric reagents to their cognate genomic targets. And furthermore, the samples where the barcoded oligonucleotides were first denatured from the barcode molecules show lower overall numbers of unique barcodes, perhaps owing to an avidity effect wherein fully assembled barcode molecules can more effectively anneal clusters of primers to nearby genomic targets at the same locus. In any case, taken together, this figure illustrates the capacity of multimeric reagents to label genomic DNA molecules, across a large number of molecules simultaneously, and to do so whether the barcoded oligonucleotides remain bound on the multimeric barcoding reagents or whether they have been denatured therefrom and thus potentially able to diffuse more readily in solution.

| Sequences of nucleic acids used in the methods | | |
|---|---|---|
| Sequence Name | Sequence ID Number | Sequence |
| BC_ADD_TP1 | SEQ ID NO 1 | CTCGATGCTACGTGACTACTGCGTCGAGGAGTCTATCC |
| BC_ANC_TP1 | SEQ ID NO 2 | ATACCTGACTGCTCGTCAGTTGAGCGAATTCCGTATGGGTAGCAAGGTCCAAGAGAGGCTCCATCCTCACTCGCCTGACTACGACAAGACCTACTG |
| BC_ANC_BT1 | SEQ ID NO 3 | TCCAGTAGGTCTTGTCGTAGTCAGGCGAGTGAGGATGGAGCCTCTCTTGGACCTTGCTACCCATACGGAATTCGCTCAACTGACGAGCAGTCAGGTAT |
| BC_FWD_PR1 | SEQ ID NO 4 | CTCGATGCTACGTGACTACTGC |
| BC_REV_PR1 | SEQ ID NO 5 | CAGTAGGTCTTGTCGTAGTCAG |
| BC_USO_TP1 | SEQ ID NO 6 | ATGGTACACACCTACACTACTCGGACGCTCTTCCGATCTTGACCT |
| BC_USO_BT1 | SEQ ID NO 7 | AGGTCAAGATCGGAAGAGCGTCCGAGTAGTGTAGGTGTGTACCA |
| BC_CS_PCR_FWD1 | SEQ ID NO 8 | TGGTACACACCTACACTACTCG |
| BC_CS_PCR_REV1 | SEQ ID NO 9 | CCATACGGAATTCGCTCAAC |
| CS_SPLT_FWD1 | SEQ ID NO 10 | GTTGAGCGAATTCCGTATGGTGGTACACACCTACACTACTCG |
| CS_TERM_FWD1 | SEQ ID NO 11 | TAGGACGATACGAGTGTGTACTCGTGGTACACACCTACACTACTCG |
| CS_SPLT_REV1 | SEQ ID NO 12 | CGAGTAGTGTAGGTGTGTACCACCATACGGAATTCGCTCAAC |
| CS_TERM_REV1 | SEQ ID NO 13 | CTGTCAAGGTAGACTAGCATGCTCCCATACGGAATTCGCTCAAC |
| CS_PCR_FWD1 | SEQ ID NO 14 | TAGGACGATACGAGTGTGTACTCG |
| CS_PCR_REV1 | SEQ ID NO 15 | CTGTCAAGGTAGACTAGCATGCTC |
| CS_SQ_AMP_REV1 | SEQ ID NO 16 | CTCGGCATTCCTGCTGAACCGCTCTTCCGATCTGCTCAACTGACGAGCAGTCAGGT |
| US_PCR_Prm_Only_02 | SEQ ID NO 17 | ACACTCTTTCCCTACACGACGCTCTTCCGATCTTGACCT |
| BC_MX3 | SEQ ID NO 18 to 269 | An equimolar mixture of all sequences in SEQ ID NO 18 to 269 |
| BC_ADD_BT1_AAAC | SEQ ID NO 18 | AAACGGATAGACTCCTCGAC |
| BC_ADD_BT1_AAAG | SEQ ID NO 19 | AAAGGGATAGACTCCTCGAC |

Sequences of nucleic acids used in the methods

| Sequence Name | Sequence ID Number | Sequence |
|---|---|---|
| BC_ADD_BT1_AAAT | SEQ ID NO 20 | AAATGGATAGACTCCTCGAC |
| BC_ADD_BT1_AACA | SEQ ID NO 21 | AACAGGATAGACTCCTCGAC |
| BC_ADD_BT1_AACC | SEQ ID NO 22 | AACCGGATAGACTCCTCGAC |
| BC_ADD_BT1_AACG | SEQ ID NO 23 | AACGGGATAGACTCCTCGAC |
| BC_ADD_BT1_AACT | SEQ ID NO 24 | AACTGGATAGACTCCTCGAC |
| BC_ADD_BT1_AAGA | SEQ ID NO 25 | AAGAGGATAGACTCCTCGAC |
| BC_ADD_BT1_AAGC | SEQ ID NO 26 | AAGCGGATAGACTCCTCGAC |
| BC_ADD_BT1_AAGG | SEQ ID NO 27 | AAGGGGATAGACTCCTCGAC |
| BC_ADD_BT1_AAGT | SEQ ID NO 28 | AAGTGGATAGACTCCTCGAC |
| BC_ADD_BT1_AATA | SEQ ID NO 29 | AATAGGATAGACTCCTCGAC |
| BC_ADD_BT1_AATC | SEQ ID NO 30 | AATCGGATAGACTCCTCGAC |
| BC_ADD_BT1_AATG | SEQ ID NO 31 | AATGGGATAGACTCCTCGAC |
| BC_ADD_BT1_AATT | SEQ ID NO 32 | AATTGGATAGACTCCTCGAC |
| BC_ADD_BT1_ACAA | SEQ ID NO 33 | ACAAGGATAGACTCCTCGAC |
| BC_ADD_BT1_ACAC | SEQ ID NO 34 | ACACGGATAGACTCCTCGAC |
| BC_ADD_BT1_ACAG | SEQ ID NO 35 | ACAGGGATAGACTCCTCGAC |
| BC_ADD_BT1_ACAT | SEQ ID NO 36 | ACATGGATAGACTCCTCGAC |
| BC_ADD_BT1_ACCA | SEQ ID NO 37 | ACCAGGATAGACTCCTCGAC |
| BC_ADD_BT1_ACCC | SEQ ID NO 38 | ACCCGGATAGACTCCTCGAC |
| BC_ADD_BT1_ACCG | SEQ ID NO 39 | ACCGGGATAGACTCCTCGAC |
| BC_ADD_BT1_ACCT | SEQ ID NO 40 | ACCTGGATAGACTCCTCGAC |
| BC_ADD_BT1_ACGA | SEQ ID NO 41 | ACGAGGATAGACTCCTCGAC |
| BC_ADD_BT1_ACGC | SEQ ID NO 42 | ACGCGGATAGACTCCTCGAC |
| BC_ADD_BT1_ACGG | SEQ ID NO 43 | ACGGGGATAGACTCCTCGAC |
| BC_ADD_BT1_ACGT | SEQ ID NO 44 | ACGTGGATAGACTCCTCGAC |
| BC_ADD_BT1_ACTA | SEQ ID NO 45 | ACTAGGATAGACTCCTCGAC |
| BC_ADD_BT1_ACTC | SEQ ID NO 46 | ACTCGGATAGACTCCTCGAC |
| BC_ADD_BT1_ACTG | SEQ ID NO 47 | ACTGGGATAGACTCCTCGAC |
| BC_ADD_BT1_ACTT | SEQ ID NO 48 | ACTTGGATAGACTCCTCGAC |
| BC_ADD_BT1_AGAA | SEQ ID NO 49 | AGAAGGATAGACTCCTCGAC |
| BC_ADD_BT1_AGAC | SEQ ID NO 50 | AGACGGATAGACTCCTCGAC |
| BC_ADD_BT1_AGAG | SEQ ID NO 51 | AGAGGGATAGACTCCTCGAC |
| BC_ADD_BT1_AGAT | SEQ ID NO 52 | AGATGGATAGACTCCTCGAC |
| BC_ADD_BT1_AGCA | SEQ ID NO 53 | AGCAGGATAGACTCCTCGAC |
| BC_ADD_BT1_AGCC | SEQ ID NO 54 | AGCCGGATAGACTCCTCGAC |
| BC_ADD_BT1_AGCG | SEQ ID NO 55 | AGCGGGATAGACTCCTCGAC |
| BC_ADD_BT1_AGCT | SEQ ID NO 56 | AGCTGGATAGACTCCTCGAC |

-continued

| Sequences of nucleic acids used in the methods | | |
|---|---|---|
| Sequence Name | Sequence ID Number | Sequence |
| BC_ADD_BT1_AGGA | SEQ ID NO 57 | AGGAGGATAGACTCCTCGAC |
| BC_ADD_BT1_AGGC | SEQ ID NO 58 | AGGCGGATAGACTCCTCGAC |
| BC_ADD_BT1_AGGG | SEQ ID NO 59 | AGGGGGATAGACTCCTCGAC |
| BC_ADD_BT1_AGGT | SEQ ID NO 60 | AGGTGGATAGACTCCTCGAC |
| BC_ADD_BT1_AGTA | SEQ ID NO 61 | AGTAGGATAGACTCCTCGAC |
| BC_ADD_BT1_AGTC | SEQ ID NO 62 | AGTCGGATAGACTCCTCGAC |
| BC_ADD_BT1_AGTG | SEQ ID NO 63 | AGTGGGATAGACTCCTCGAC |
| BC_ADD_BT1_AGTT | SEQ ID NO 64 | AGTTGGATAGACTCCTCGAC |
| BC_ADD_BT1_ATAA | SEQ ID NO 65 | ATAAGGATAGACTCCTCGAC |
| BC_ADD_BT1_ATAC | SEQ ID NO 66 | ATACGGATAGACTCCTCGAC |
| BC_ADD_BT1_ATAG | SEQ ID NO 67 | ATAGGGATAGACTCCTCGAC |
| BC_ADD_BT1_ATAT | SEQ ID NO 68 | ATATGGATAGACTCCTCGAC |
| BC_ADD_BT1_ATCA | SEQ ID NO 69 | ATCAGGATAGACTCCTCGAC |
| BC_ADD_BT1_ATCC | SEQ ID NO 70 | ATCCGGATAGACTCCTCGAC |
| BC_ADD_BT1_ATCG | SEQ ID NO 71 | ATCGGGATAGACTCCTCGAC |
| BC_ADD_BT1_ATCT | SEQ ID NO 72 | ATCTGGATAGACTCCTCGAC |
| BC_ADD_BT1_ATGA | SEQ ID NO 73 | ATGAGGATAGACTCCTCGAC |
| BC_ADD_BT1_ATGC | SEQ ID NO 74 | ATGCGGATAGACTCCTCGAC |
| BC_ADD_BT1_ATGG | SEQ ID NO 75 | ATGGGGATAGACTCCTCGAC |
| BC_ADD_BT1_ATGT | SEQ ID NO 76 | ATGTGGATAGACTCCTCGAC |
| BC_ADD_BT1_ATTA | SEQ ID NO 77 | ATTAGGATAGACTCCTCGAC |
| BC_ADD_BT1_ATTC | SEQ ID NO 78 | ATTCGGATAGACTCCTCGAC |
| BC_ADD_BT1_ATTG | SEQ ID NO 79 | ATTGGGATAGACTCCTCGAC |
| BC_ADD_BT1_ATTT | SEQ ID NO 80 | ATTTGGATAGACTCCTCGAC |
| BC_ADD_BT1_CAAA | SEQ ID NO 81 | CAAAGGATAGACTCCTCGAC |
| BC_ADD_BT1_CAAC | SEQ ID NO 82 | CAACGGATAGACTCCTCGAC |
| BC_ADD_BT1_CAAG | SEQ ID NO 83 | CAAGGGATAGACTCCTCGAC |
| BC_ADD_BT1_CAAT | SEQ ID NO 84 | CAATGGATAGACTCCTCGAC |
| BC_ADD_BT1_CACA | SEQ ID NO 85 | CACAGGATAGACTCCTCGAC |
| BC_ADD_BT1_CACC | SEQ ID NO 86 | CACCGGATAGACTCCTCGAC |
| BC_ADD_BT1_CACG | SEQ ID NO 87 | CACGGGATAGACTCCTCGAC |
| BC_ADD_BT1_CACT | SEQ ID NO 88 | CACTGGATAGACTCCTCGAC |
| BC_ADD_BT1_CAGA | SEQ ID NO 89 | CAGAGGATAGACTCCTCGAC |
| BC_ADD_BT1_CAGC | SEQ ID NO 90 | CAGCGGATAGACTCCTCGAC |
| BC_ADD_BT1_CAGG | SEQ ID NO 91 | CAGGGGATAGACTCCTCGAC |
| BC_ADD_BT1_CAGT | SEQ ID NO 92 | CAGTGGATAGACTCCTCGAC |
| BC_ADD_BT1_CATA | SEQ ID NO 93 | CATAGGATAGACTCCTCGAC |

-continued

Sequences of nucleic acids used in the methods

| Sequence Name | Sequence ID Number | Sequence |
|---|---|---|
| BC_ADD_BT1_CATC | SEQ ID NO 94 | CATCGGATAGACTCCTCGAC |
| BC_ADD_BT1_CATG | SEQ ID NO 95 | CATGGGATAGACTCCTCGAC |
| BC_ADD_BT1_CATT | SEQ ID NO 96 | CATTGGATAGACTCCTCGAC |
| BC_ADD_BT1_CCAA | SEQ ID NO 97 | CCAAGGATAGACTCCTCGAC |
| BC_ADD_BT1_CCAC | SEQ ID NO 98 | CCACGGATAGACTCCTCGAC |
| BC_ADD_BT1_CCAG | SEQ ID NO 99 | CCAGGGATAGACTCCTCGAC |
| BC_ADD_BT1_CCAT | SEQ ID NO 100 | CCATGGATAGACTCCTCGAC |
| BC_ADD_BT1_CCCA | SEQ ID NO 101 | CCCAGGATAGACTCCTCGAC |
| BC_ADD_BT1_CCCG | SEQ ID NO 102 | CCCGGGATAGACTCCTCGAC |
| BC_ADD_BT1_CCCT | SEQ ID NO 103 | CCCTGGATAGACTCCTCGAC |
| BC_ADD_BT1_CCGA | SEQ ID NO 104 | CCGAGGATAGACTCCTCGAC |
| BC_ADD_BT1_CCGC | SEQ ID NO 105 | CCGCGGATAGACTCCTCGAC |
| BC_ADD_BT1_CCGG | SEQ ID NO 106 | CCGGGGATAGACTCCTCGAC |
| BC_ADD_BT1_CCGT | SEQ ID NO 107 | CCGTGGATAGACTCCTCGAC |
| BC_ADD_BT1_CCTA | SEQ ID NO 108 | CCTAGGATAGACTCCTCGAC |
| BC_ADD_BT1_CCTC | SEQ ID NO 109 | CCTCGGATAGACTCCTCGAC |
| BC_ADD_BT1_CCTG | SEQ ID NO 110 | CCTGGGATAGACTCCTCGAC |
| BC_ADD_BT1_CCTT | SEQ ID NO 111 | CCTTGGATAGACTCCTCGAC |
| BC_ADD_BT1_CGAA | SEQ ID NO 112 | CGAAGGATAGACTCCTCGAC |
| BC_ADD_BT1_CGAC | SEQ ID NO 113 | CGACGGATAGACTCCTCGAC |
| BC_ADD_BT1_CGAG | SEQ ID NO 114 | CGAGGGATAGACTCCTCGAC |
| BC_ADD_BT1_CGAT | SEQ ID NO 115 | CGATGGATAGACTCCTCGAC |
| BC_ADD_BT1_CGCA | SEQ ID NO 116 | CGCAGGATAGACTCCTCGAC |
| BC_ADD_BT1_CGCC | SEQ ID NO 117 | CGCCGGATAGACTCCTCGAC |
| BC_ADD_BT1_CGCG | SEQ ID NO 118 | CGCGGGATAGACTCCTCGAC |
| BC_ADD_BT1_CGCT | SEQ ID NO 119 | CGCTGGATAGACTCCTCGAC |
| BC_ADD_BT1_CGGA | SEQ ID NO 120 | CGGAGGATAGACTCCTCGAC |
| BC_ADD_BT1_CGGC | SEQ ID NO 121 | CGGCGGATAGACTCCTCGAC |
| BC_ADD_BT1_CGGG | SEQ ID NO 122 | CGGGGGATAGACTCCTCGAC |
| BC_ADD_BT1_CGGT | SEQ ID NO 123 | CGGTGGATAGACTCCTCGAC |
| BC_ADD_BT1_CGTA | SEQ ID NO 124 | CGTAGGATAGACTCCTCGAC |
| BC_ADD_BT1_CGTC | SEQ ID NO 125 | CGTCGGATAGACTCCTCGAC |
| BC_ADD_BT1_CGTG | SEQ ID NO 126 | CGTGGGATAGACTCCTCGAC |
| BC_ADD_BT1_CGTT | SEQ ID NO 127 | CGTTGGATAGACTCCTCGAC |
| BC_ADD_BT1_CTAA | SEQ ID NO 128 | CTAAGGATAGACTCCTCGAC |
| BC_ADD_BT1_CTAC | SEQ ID NO 129 | CTACGGATAGACTCCTCGAC |
| BC_ADD_BT1_CTAG | SEQ ID NO 130 | CTAGGGATAGACTCCTCGAC |

-continued

| Sequences of nucleic acids used in the methods | | |
|---|---|---|
| Sequence Name | Sequence ID Number | Sequence |
| BC_ADD_BT1_CTAT | SEQ ID NO 131 | CTATGGATAGACTCCTCGAC |
| BC_ADD_BT1_CTCA | SEQ ID NO 132 | CTCAGGATAGACTCCTCGAC |
| BC_ADD_BT1_CTCC | SEQ ID NO 133 | CTCCGGATAGACTCCTCGAC |
| BC_ADD_BT1_CTCG | SEQ ID NO 134 | CTCGGGATAGACTCCTCGAC |
| BC_ADD_BT1_CTCT | SEQ ID NO 135 | CTCTGGATAGACTCCTCGAC |
| BC_ADD_BT1_CTGA | SEQ ID NO 136 | CTGAGGATAGACTCCTCGAC |
| BC_ADD_BT1_CTGC | SEQ ID NO 137 | CTGCGGATAGACTCCTCGAC |
| BC_ADD_BT1_CTGG | SEQ ID NO 138 | CTGGGGATAGACTCCTCGAC |
| BC_ADD_BT1_CTGT | SEQ ID NO 139 | CTGTGGATAGACTCCTCGAC |
| BC_ADD_BT1_CTTA | SEQ ID NO 140 | CTTAGGATAGACTCCTCGAC |
| BC_ADD_BT1_CTTC | SEQ ID NO 141 | CTTCGGATAGACTCCTCGAC |
| BC_ADD_BT1_CTTG | SEQ ID NO 142 | CTTGGGATAGACTCCTCGAC |
| BC_ADD_BT1_CTTT | SEQ ID NO 143 | CTTTGGATAGACTCCTCGAC |
| BC_ADD_BT1_GAAA | SEQ ID NO 144 | GAAAGGATAGACTCCTCGAC |
| BC_ADD_BT1_GAAC | SEQ ID NO 145 | GAACGGATAGACTCCTCGAC |
| BC_ADD_BT1_GAAG | SEQ ID NO 146 | GAAGGGATAGACTCCTCGAC |
| BC_ADD_BT1_GAAT | SEQ ID NO 147 | GAATGGATAGACTCCTCGAC |
| BC_ADD_BT1_GACA | SEQ ID NO 148 | GACAGGATAGACTCCTCGAC |
| BC_ADD_BT1_GACC | SEQ ID NO 149 | GACCGGATAGACTCCTCGAC |
| BC_ADD_BT1_GACG | SEQ ID NO 150 | GACGGGATAGACTCCTCGAC |
| BC_ADD_BT1_GACT | SEQ ID NO 151 | GACTGGATAGACTCCTCGAC |
| BC_ADD_BT1_GAGA | SEQ ID NO 152 | GAGAGGATAGACTCCTCGAC |
| BC_ADD_BT1_GAGC | SEQ ID NO 153 | GAGCGGATAGACTCCTCGAC |
| BC_ADD_BT1_GAGG | SEQ ID NO 154 | GAGGGGATAGACTCCTCGAC |
| BC_ADD_BT1_GAGT | SEQ ID NO 155 | GAGTGGATAGACTCCTCGAC |
| BC_ADD_BT1_GATA | SEQ ID NO 156 | GATAGGATAGACTCCTCGAC |
| BC_ADD_BT1_GATC | SEQ ID NO 157 | GATCGGATAGACTCCTCGAC |
| BC_ADD_BT1_GATG | SEQ ID NO 158 | GATGGGATAGACTCCTCGAC |
| BC_ADD_BT1_GATT | SEQ ID NO 159 | GATTGGATAGACTCCTCGAC |
| BC_ADD_BT1_GCAA | SEQ ID NO 160 | GCAAGGATAGACTCCTCGAC |
| BC_ADD_BT1_GCAC | SEQ ID NO 161 | GCACGGATAGACTCCTCGAC |
| BC_ADD_BT1_GCAG | SEQ ID NO 162 | GCAGGGATAGACTCCTCGAC |
| BC_ADD_BT1_GCAT | SEQ ID NO 163 | GCATGGATAGACTCCTCGAC |
| BC_ADD_BT1_GCCA | SEQ ID NO 164 | GCCAGGATAGACTCCTCGAC |
| BC_ADD_BT1_GCCC | SEQ ID NO 165 | GCCCGGATAGACTCCTCGAC |
| BC_ADD_BT1_GCCG | SEQ ID NO 166 | GCCGGGATAGACTCCTCGAC |
| BC_ADD_BT1_GCCT | SEQ ID NO 167 | GCCTGGATAGACTCCTCGAC |

-continued

Sequences of nucleic acids used in the methods

| Sequence Name | Sequence ID Number | Sequence |
|---|---|---|
| BC_ADD_BT1_GCGA | SEQ ID NO 168 | GCGAGGATAGACTCCTCGAC |
| BC_ADD_BT1_GCGC | SEQ ID NO 169 | GCGCGGATAGACTCCTCGAC |
| BC_ADD_BT1_GCGG | SEQ ID NO 170 | GCGGGGATAGACTCCTCGAC |
| BC_ADD_BT1_GCGT | SEQ ID NO 171 | GCGTGGATAGACTCCTCGAC |
| BC_ADD_BT1_GCTA | SEQ ID NO 172 | GCTAGGATAGACTCCTCGAC |
| BC_ADD_BT1_GCTC | SEQ ID NO 173 | GCTCGGATAGACTCCTCGAC |
| BC_ADD_BT1_GCTG | SEQ ID NO 174 | GCTGGGATAGACTCCTCGAC |
| BC_ADD_BT1_GCTT | SEQ ID NO 175 | GCTTGGATAGACTCCTCGAC |
| BC_ADD_BT1_GGAA | SEQ ID NO 176 | GGAAGGATAGACTCCTCGAC |
| BC_ADD_BT1_GGAC | SEQ ID NO 177 | GGACGGATAGACTCCTCGAC |
| BC_ADD_BT1_GGAG | SEQ ID NO 178 | GGAGGGATAGACTCCTCGAC |
| BC_ADD_BT1_GGAT | SEQ ID NO 179 | GGATGGATAGACTCCTCGAC |
| BC_ADD_BT1_GGCA | SEQ ID NO 180 | GGCAGGATAGACTCCTCGAC |
| BC_ADD_BT1_GGCC | SEQ ID NO 181 | GGCCGGATAGACTCCTCGAC |
| BC_ADD_BT1_GGCG | SEQ ID NO 182 | GGCGGGATAGACTCCTCGAC |
| BC_ADD_BT1_GGCT | SEQ ID NO 183 | GGCTGGATAGACTCCTCGAC |
| BC_ADD_BT1_GGGA | SEQ ID NO 184 | GGGAGGATAGACTCCTCGAC |
| BC_ADD_BT1_GGGC | SEQ ID NO 185 | GGGCGGATAGACTCCTCGAC |
| BC_ADD_BT1_GGGT | SEQ ID NO 186 | GGGTGGATAGACTCCTCGAC |
| BC_ADD_BT1_GGTA | SEQ ID NO 187 | GGTAGGATAGACTCCTCGAC |
| BC_ADD_BT1_GGTC | SEQ ID NO 188 | GGTCGGATAGACTCCTCGAC |
| BC_ADD_BT1_GGTG | SEQ ID NO 189 | GGTGGGATAGACTCCTCGAC |
| BC_ADD_BT1_GGTT | SEQ ID NO 190 | GGTTGGATAGACTCCTCGAC |
| BC_ADD_BT1_GTAA | SEQ ID NO 191 | GTAAGGATAGACTCCTCGAC |
| BC_ADD_BT1_GTAC | SEQ ID NO 192 | GTACGGATAGACTCCTCGAC |
| BC_ADD_BT1_GTAG | SEQ ID NO 193 | GTAGGGATAGACTCCTCGAC |
| BC_ADD_BT1_GTAT | SEQ ID NO 194 | GTATGGATAGACTCCTCGAC |
| BC_ADD_BT1_GTCA | SEQ ID NO 195 | GTCAGGATAGACTCCTCGAC |
| BC_ADD_BT1_GTCC | SEQ ID NO 196 | GTCCGGATAGACTCCTCGAC |
| BC_ADD_BT1_GTCG | SEQ ID NO 197 | GTCGGGATAGACTCCTCGAC |
| BC_ADD_BT1_GTCT | SEQ ID NO 198 | GTCTGGATAGACTCCTCGAC |
| BC_ADD_BT1_GTGA | SEQ ID NO 199 | GTGAGGATAGACTCCTCGAC |
| BC_ADD_BT1_GTGC | SEQ ID NO 200 | GTGCGGATAGACTCCTCGAC |
| BC_ADD_BT1_GTGG | SEQ ID NO 201 | GTGGGGATAGACTCCTCGAC |
| BC_ADD_BT1_GTGT | SEQ ID NO 202 | GTGTGGATAGACTCCTCGAC |
| BC_ADD_BT1_GTTA | SEQ ID NO 203 | GTTAGGATAGACTCCTCGAC |
| BC_ADD_BT1_GTTC | SEQ ID NO 204 | GTTCGGATAGACTCCTCGAC |

Sequences of nucleic acids used in the methods

| Sequence Name | Sequence ID Number | Sequence |
|---|---|---|
| BC_ADD_BT1_GTTG | SEQ ID NO 205 | GTTGGGATAGACTCCTCGAC |
| BC_ADD_BT1_GTTT | SEQ ID NO 206 | GTTTGGATAGACTCCTCGAC |
| BC_ADD_BT1_TAAA | SEQ ID NO 207 | TAAAGGATAGACTCCTCGAC |
| BC_ADD_BT1_TAAC | SEQ ID NO 208 | TAACGGATAGACTCCTCGAC |
| BC_ADD_BT1_TAAG | SEQ ID NO 209 | TAAGGGATAGACTCCTCGAC |
| BC_ADD_BT1_TAAT | SEQ ID NO 210 | TAATGGATAGACTCCTCGAC |
| BC_ADD_BT1_TACA | SEQ ID NO 211 | TACAGGATAGACTCCTCGAC |
| BC_ADD_BT1_TACC | SEQ ID NO 212 | TACCGGATAGACTCCTCGAC |
| BC_ADD_BT1_TACG | SEQ ID NO 213 | TACGGGATAGACTCCTCGAC |
| BC_ADD_BT1_TACT | SEQ ID NO 214 | TACTGGATAGACTCCTCGAC |
| BC_ADD_BT1_TAGA | SEQ ID NO 215 | TAGAGGATAGACTCCTCGAC |
| BC_ADD_BT1_TAGC | SEQ ID NO 216 | TAGCGGATAGACTCCTCGAC |
| BC_ADD_BT1_TAGG | SEQ ID NO 217 | TAGGGGATAGACTCCTCGAC |
| BC_ADD_BT1_TAGT | SEQ ID NO 218 | TAGTGGATAGACTCCTCGAC |
| BC_ADD_BT1_TATA | SEQ ID NO 219 | TATAGGATAGACTCCTCGAC |
| BC_ADD_BT1_TATC | SEQ ID NO 220 | TATCGGATAGACTCCTCGAC |
| BC_ADD_BT1_TATG | SEQ ID NO 221 | TATGGGATAGACTCCTCGAC |
| BC_ADD_BT1_TATT | SEQ ID NO 222 | TATTGGATAGACTCCTCGAC |
| BC_ADD_BT1_TCAA | SEQ ID NO 223 | TCAAGGATAGACTCCTCGAC |
| BC_ADD_BT1_TCAC | SEQ ID NO 224 | TCACGGATAGACTCCTCGAC |
| BC_ADD_BT1_TCAG | SEQ ID NO 225 | TCAGGGATAGACTCCTCGAC |
| BC_ADD_BT1_TCAT | SEQ ID NO 226 | TCATGGATAGACTCCTCGAC |
| BC_ADD_BT1_TCCA | SEQ ID NO 227 | TCCAGGATAGACTCCTCGAC |
| BC_ADD_BT1_TCCC | SEQ ID NO 228 | TCCCGGATAGACTCCTCGAC |
| BC_ADD_BT1_TCCG | SEQ ID NO 229 | TCCGGGATAGACTCCTCGAC |
| BC_ADD_BT1_TCCT | SEQ ID NO 230 | TCCTGGATAGACTCCTCGAC |
| BC_ADD_BT1_TCGA | SEQ ID NO 231 | TCGAGGATAGACTCCTCGAC |
| BC_ADD_BT1_TCGC | SEQ ID NO 232 | TCGCGGATAGACTCCTCGAC |
| BC_ADD_BT1_TCGG | SEQ ID NO 233 | TCGGGGATAGACTCCTCGAC |
| BC_ADD_BT1_TCGT | SEQ ID NO 234 | TCGTGGATAGACTCCTCGAC |
| BC_ADD_BT1_TCTA | SEQ ID NO 235 | TCTAGGATAGACTCCTCGAC |
| BC_ADD_BT1_TCTC | SEQ ID NO 236 | TCTCGGATAGACTCCTCGAC |
| BC_ADD_BT1_TCTG | SEQ ID NO 237 | TCTGGGATAGACTCCTCGAC |
| BC_ADD_BT1_TCTT | SEQ ID NO 238 | TCTTGGATAGACTCCTCGAC |
| BC_ADD_BT1_TGAA | SEQ ID NO 239 | TGAAGGATAGACTCCTCGAC |
| BC_ADD_BT1_TGAC | SEQ ID NO 240 | TGACGGATAGACTCCTCGAC |
| BC_ADD_BT1_TGAG | SEQ ID NO 241 | TGAGGGATAGACTCCTCGAC |

| | Sequences of nucleic acids used in the methods | |
|---|---|---|
| Sequence Name | Sequence ID Number | Sequence |
| BC_ADD_BT1_TGAT | SEQ ID NO 242 | TGATGGATAGACTCCTCGAC |
| BC_ADD_BT1_TGCA | SEQ ID NO 243 | TGCAGGATAGACTCCTCGAC |
| BC_ADD_BT1_TGCC | SEQ ID NO 244 | TGCCGGATAGACTCCTCGAC |
| BC_ADD_BT1_TGCG | SEQ ID NO 245 | TGCGGGATAGACTCCTCGAC |
| BC_ADD_BT1_TGCT | SEQ ID NO 246 | TGCTGGATAGACTCCTCGAC |
| BC_ADD_BT1_TGGA | SEQ ID NO 247 | TGGAGGATAGACTCCTCGAC |
| BC_ADD_BT1_TGGC | SEQ ID NO 248 | TGGCGGATAGACTCCTCGAC |
| BC_ADD_BT1_TGGG | SEQ ID NO 249 | TGGGGGATAGACTCCTCGAC |
| BC_ADD_BT1_TGGT | SEQ ID NO 250 | TGGTGGATAGACTCCTCGAC |
| BC_ADD_BT1_TGTA | SEQ ID NO 251 | TGTAGGATAGACTCCTCGAC |
| BC_ADD_BT1_TGTC | SEQ ID NO 252 | TGTCGGATAGACTCCTCGAC |
| BC_ADD_BT1_TGTG | SEQ ID NO 253 | TGTGGGATAGACTCCTCGAC |
| BC_ADD_BT1_TGTT | SEQ ID NO 254 | TGTTGGATAGACTCCTCGAC |
| BC_ADD_BT1_TTAA | SEQ ID NO 255 | TTAAGGATAGACTCCTCGAC |
| BC_ADD_BT1_TTAC | SEQ ID NO 256 | TTACGGATAGACTCCTCGAC |
| BC_ADD_BT1_TTAG | SEQ ID NO 257 | TTAGGGATAGACTCCTCGAC |
| BC_ADD_BT1_TTAT | SEQ ID NO 258 | TTATGGATAGACTCCTCGAC |
| BC_ADD_BT1_TTCA | SEQ ID NO 259 | TTCAGGATAGACTCCTCGAC |
| BC_ADD_BT1_TTCC | SEQ ID NO 260 | TTCCGGATAGACTCCTCGAC |
| BC_ADD_BT1_TTCG | SEQ ID NO 261 | TTCGGGATAGACTCCTCGAC |
| BC_ADD_BT1_TTCT | SEQ ID NO 262 | TTCTGGATAGACTCCTCGAC |
| BC_ADD_BT1_TTGA | SEQ ID NO 263 | TTGAGGATAGACTCCTCGAC |
| BC_ADD_BT1_TTGC | SEQ ID NO 264 | TTGCGGATAGACTCCTCGAC |
| BC_ADD_BT1_TTGG | SEQ ID NO 265 | TTGGGGATAGACTCCTCGAC |
| BC_ADD_BT1_TTGT | SEQ ID NO 266 | TTGTGGATAGACTCCTCGAC |
| BC_ADD_BT1_TTTA | SEQ ID NO 267 | TTTAGGATAGACTCCTCGAC |
| BC_ADD_BT1_TTTC | SEQ ID NO 268 | TTTCGGATAGACTCCTCGAC |
| BC_ADD_BT1_TTTG | SEQ ID NO 269 | TTTGGGATAGACTCCTCGAC |
| CS_PCR_FWD1_T7 | SEQ ID NO 270 | TAATACGACTCACTATAGGGAGATAGGACGATACGAGTGTGTACTCG |
| CS_PCR_REV4 | SEQ ID NO 271 | CTGTCAAGGTAGACTAGCATGCTCCCATACG |
| CS_PCR_REV1 | SEQ ID NO 272 | CTGTCAAGGTAGACTAGCATGCTC |
| DS_ST_05 | SEQ ID NO 273 | CCTGACTGCTCGTCAGTTGATTAAGTACTCTGTGAGATGATGATCAGTAGAGCGAGTCGT; 5' phosphate |
| US_PCR_Prm_Only_03 | SEQ ID NO 274 | CACCGAGATCTACACTCTTTCCCTACACGACGCTCTTCCGATCTTGACCT |

-continued

Sequences of nucleic acids used in the methods

| Sequence Name | Sequence ID Number | Sequence |
|---|---|---|
| Syn_Temp_01 | SEQ ID NO 275 | ATGATCAGTAGAGCGAGTCGTNNNNNNNNNN NNNNNNNNNTGCTACGACTTCCGAGTCCA; 5' phosphate; N = fully degenerate nucleotide, any one of (A/T/C/G) with approximately equal likelihoods |
| ST_Splint_02 | SEQ ID NO 276 | GCTCTACTGATCATTGGACTCGGAAGT |
| SynTemp_PE2_B1_Short1 | SEQ ID NO 277 | TCCGATCTTGGACTCGGAAGTCGTAGCA |
| US_PCR_Prm_Only_02 | SEQ ID NO 278 | ACACTCTTTCCCTACACGACGCTCTTCCGAT CTTGACCT |
| BRCA1_SNP1_F2 | SEQ ID NO 279 | CCTGACTGCTCGTCAGTTGATTAAGTACTCT GTGAGATGCTTGGCCCCTCTTCGGTAAC; 5' phosphate |
| BRCA1_SNP6_F2 | SEQ ID NO 280 | CCTGACTGCTCGTCAGTTGATTAAGTACTCT GTGAGATGCTGGGAGCTCAAAAGATGGCT; 5' phosphate |
| BRCA1_SNP7_F2 | SEQ ID NO 281 | CCTGACTGCTCGTCAGTTGATTAAGTACTCT GTGAGATGCAGCTGGGCTCAAAGGACC; 5' phosphate |
| BRCA1_US1_F2 | SEQ ID NO 282 | CCTGACTGCTCGTCAGTTGATTAAGTACTCT GTGAGATGCAGACAAATTCCCCAGCAGGT; 5' phosphate |
| BRCA1_DS1_F2 | SEQ ID NO 283 | CCTGACTGCTCGTCAGTTGATTAAGTACTCT GTGAGATGCATGGTGTGAACCCGGGAG; 5' phosphate |
| BRCA1_AMP6_F2 | SEQ ID NO 284 | CCTGACTGCTCGTCAGTTGATTAAGTACTCT GTGAGATGCCCAAATCCCAAGTCGTGTGT; 5' phosphate |
| BRCA1_AMP7_F2 | SEQ ID NO 285 | CCTGACTGCTCGTCAGTTGATTAAGTACTCT GTGAGATGCTCATCCCTGGTTCCTTGAGG; 5' phosphate |
| HLA-A_E2_F2 | SEQ ID NO 286 | CCTGACTGCTCGTCAGTTGATTAAGTACTCT GTGAAAACGGCCTCTGTGGGAGAAGCAA; 5' phosphate |
| HLA-A_E3_F2 | SEQ ID NO 287 | CCTGACTGCTCGTCAGTTGATTAAGTACTCT GTGAGATGCACTGGGCTGACCGTGGGGT; 5' phosphate |
| HLA-A_E4_F2 | SEQ ID NO 288 | CCTGACTGCTCGTCAGTTGATTAAGTACTCT GCCTGAATGWTCTGACTCTTCCCGTMAGA; 5' phosphate |
| DQB1_E2_F2 | SEQ ID NO 289 | CCTGACTGCTCGTCAGTTGATTAAGTACTCT GGGATCCCCGCAGAGGATTCGTGTACCA; 5' phosphate |
| DQB1_E3_F2 | SEQ ID NO 290 | CCTGACTGCTCGTCAGTTGATTAAGTACTCT GTGAGATGGAGCCCACAGTGACCATCTCC; 5' phosphate |
| BRCA1_SNP1_R3 | SEQ ID NO 291 | CGGTCTCGGCATTCCTGCTGAACCGCTCTTC CGATCTGTTCTGAGACACCTGATGACCTG |
| BRCA1_SNP6_R3 | SEQ ID NO 292 | CGGTCTCGGCATTCCTGCTGAACCGCTCTTC CGATCTTGAACCCAGGAGTTTGAGGC |
| BRCA1_SNP7_R3 | SEQ ID NO 293 | CGGTCTCGGCATTCCTGCTGAACCGCTCTTC CGATCTTGGAGCTTTATCTGCTCTGTGAT |
| BRCA1_US1_R3 | SEQ ID NO 294 | CGGTCTCGGCATTCCTGCTGAACCGCTCTTC CGATCTTTCACTGTGATGGCCAGGAT |

Sequences of nucleic acids used in the methods

| Sequence Name | Sequence ID Number | Sequence |
|---|---|---|
| BRCA1_DS1_R3 | SEQ ID NO 295 | CGGTCTCGGCATTCCTGCTGAACCGCTCTTC CGATCTTGACCCAAGCAAGCCTAAAG |
| BRCA1_AMP6_R3 | SEQ ID NO 296 | CGGTCTCGGCATTCCTGCTGAACCGCTCTTC CGATCTTGCCACAGTAGATGCTCAGT |
| BRCA1_AMP7_R3 | SEQ ID NO 297 | CGGTCTCGGCATTCCTGCTGAACCGCTCTTC CGATCTCCCAGCAACCATTTCATTTCA |
| HLA-A_E2_R3 | SEQ ID NO 298 | CGGTCTCGGCATTCCTGCTGAACCGCTCTTC CGATCTTGGATCTCGGACCCGGAGACTGT |
| HLA-A_E3_R3 | SEQ ID NO 299 | CGGTCTCGGCATTCCTGCTGAACCGCTCTTC CGATCTCCCTGGTACCVGTGCGCTGCA |
| HLA-A_E4_R3A | SEQ ID NO 300 | CGGTCTCGGCATTCCTGCTGAACCGCTCTTC CGATCTGACCCTGCTAAAGGTCTCCAGAG |
| HLA-A_E4_R3B | SEQ ID NO 301 | CGGTCTCGGCATTCCTGCTGAACCGCTCTTC CGATCTGACCCTGCTAAAGGTCAGAG |
| DQB1_E2_R3 | SEQ ID NO 302 | CGGTCTCGGCATTCCTGCTGAACCGCTCTTC CGATCTAGGACGCTCACCTCTCCGCTGCA |
| DQB1_E3_R3 | SEQ ID NO 303 | CGGTCTCGGCATTCCTGCTGAACCGCTCTTC CGATCTCTGGGGTGCTCCACGTGGCA |

The invention claimed is:

1. A method of generating a synthetic long read from a target nucleic acid comprising the steps of:
   a) preparing a nucleic acid sample for sequencing using a multimeric barcode molecule, wherein the nucleic acid sample comprises a target nucleic acid, wherein the multimeric barcode molecule comprises first, second, and third barcode regions, and wherein preparing the nucleic acid sample for sequencing comprises producing first, second, and third barcoded target nucleic acid molecules, wherein the first barcoded target nucleic acid molecule comprises a first sub-sequence of the target nucleic acid and the nucleic acid sequence or complement thereof of the first barcode region, wherein the second barcoded target nucleic acid molecule comprises a second sub-sequence of the target nucleic acid and the nucleic acid sequence or complement thereof of the second barcode region, and wherein the third barcoded target nucleic acid molecule comprises a third sub-sequence of the target nucleic acid and the nucleic acid sequence or complement thereof of the third barcode region;
   b) sequencing the sample, wherein the step of sequencing comprises sequencing at least part of the first barcoded target nucleic acid molecule to generate a first sequence read, sequencing at least part of the second barcoded target nucleic acid molecule to generate a second sequence read, and sequencing at least part of the third barcoded target nucleic acid molecule to generate a third sequence read; and c) processing the sequence data obtained by step (b) to generate a synthetic long read from the target nucleic acid, wherein the processing comprises:
  i. identifying for each sequence read the sequence of the barcode region and the sequence from the target nucleic acid; and
  ii. using the information from step (i) to determine a group of sequences from the target nucleic acid that were labelled with barcode regions from the same multimeric barcode molecule;

and wherein the synthetic long read comprises at least one nucleotide corresponding to the target nucleic acid from each of the first, second, and third sequence reads.

2. The method of claim 1, wherein the barcode regions uniquely identify each of the barcoded target nucleic acid molecules.

3. The method of claim 1, wherein the multimeric barcode molecule comprises at least 5, at least 10, at least 20, at least 25, at least 50, at least 75, or at least 100 barcode regions.

4. The method of claim 1, wherein step (a) comprises preparing the nucleic acid sample for sequencing using a library of multimeric barcode molecules, wherein the library of multimeric barcode molecules comprises at least 2, at least 5, at least 10, at least 20, at least 25, at least 50, at least 75, at least 100, at least 250, at least 500, at least $10^3$, at least $10^4$, at least $10^5$, at least $10^6$, at least $10^7$, or at least $10^8$ multimeric barcode molecules, and wherein each of the multimeric barcode molecules is as defined in claim 1.

5. The method of claim 1, wherein step (a) comprises preparing the nucleic acid sample for sequencing using a library of multimeric barcode molecules, wherein the library of multimeric barcode molecules comprises at least 2, at least 5, at least 10, at least 20, at least 25, at least 50, at least 75, at least 100, at least 250, at least 500, at least $10^3$, at least $10^4$, at least $10^5$, at least $10^6$, at least $10^7$ or at least $10^8$ multimeric barcode molecules, wherein each of the multimeric barcode molecules is as defined in claim 1, and wherein the barcode regions of each multimeric barcode molecule are different to the barcode regions of at least 1, at least 4, at least 9, at least 19, at least 24, at least 49, at least 74, at least 99, at least 249, at least 499, at least $10^3$-1, at least $10^4$-1, at least $10^5$-1, at least $10^6$-1, at least $10^7$-1, or at least $10^8$-1 other multimeric barcode molecules in the library.

6. The method of claim 1, wherein step (a) comprises preparing the nucleic acid sample for sequencing using a library of multimeric barcode molecules, wherein the library of multimeric barcode molecules comprises at least 2, at least 5, at least 10, at least 20, at least 25, at least 50, at least 75, at least 100, at least 250, at least 500, at least $10^3$, at least $10^4$, at least $10^5$, at least $10^6$, at least $10^7$, or at least $10^8$ multimeric barcode molecules, and wherein each of the multimeric barcode molecules is as defined in claim 1, and wherein the method generates a synthetic long read from each of at least 2, at least 5, at least 10, at least 20, at least 25, at least 50, at least 75, at least 100, at least 250, at least 500, at least $10^3$, at least $10^4$, at least $10^5$, at least $10^6$, at least $10^7$, or at least $10^8$ target nucleic acids.

7. The method of claim 1, wherein the synthetic long read comprises at least 50, at least 100, at least 250, at least 500, at least 750, at least 1000, or at least 2000 nucleotides corresponding to the target nucleic acid.

* * * * *

SEQUENCE LISTING

<160> NUMBER OF SEQ ID NOS: 303

<210> SEQ ID NO 1
<211> LENGTH: 38
<212> TYPE: DNA
<213> ORGANISM: Artificial Sequence
<220> FEATURE:
<223> OTHER INFORMATION: Primer

<400> SEQUENCE: 1
ctcgatgcta cgtgactact gcgtcgagga gtctatcc                            38

<210> SEQ ID NO 2
<211> LENGTH: 96
<212> TYPE: DNA
<213> ORGANISM: Artificial Sequence
<220> FEATURE:
<223> OTHER INFORMATION: Primer

<400> SEQUENCE: 2
atacctgact gctcgtcagt tgagcgaatt ccgtatgggt agcaaggtcc aagagaggct    60
ccatcctcac tcgcctgact acgacaagac ctactg                              96

<210> SEQ ID NO 3
<211> LENGTH: 98
<212> TYPE: DNA
<213> ORGANISM: Artificial Sequence
<220> FEATURE:
<223> OTHER INFORMATION: Primer

<400> SEQUENCE: 3
tccagtaggt cttgtcgtag tcaggcgagt gaggatggag cctctcttgg accttgctac    60
ccatacggaa ttcgctcaac tgacgagcag tcaggtat                            98

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ctcgatgcta cgtgactact gc                                    22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
cagtaggtct tgtcgtagtc ag                                    22

<210> SEQ ID NO 6
<211> LENGTH: 45
<212> TYPE: DNA
<213> ORGANISM: Artificial Sequence
<220> FEATURE:
<223> OTHER INFORMATION: Primer

<400> SEQUENCE: 6
atggtacaca cctacactac tcggacgctc ttccgatctt gacct           45

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
aggtcaagat cggaagagcg tccgagtagt gtaggtgtgt acca            44

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tggtacacac ctacactact cg                                    22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccatacggaa ttcgctcaac                                       20

<210> SEQ ID NO 10
<211> LENGTH: 42
<212> TYPE: DNA
<213> ORGANISM: Artificial Sequence
<220> FEATURE:
<223> OTHER INFORMATION: Primer

<400> SEQUENCE: 10
gttgagcgaa ttccgtatgg tggtacacac ctacactact cg                42

<210> SEQ ID NO 11
<211> LENGTH: 46
<212> TYPE: DNA
<213> ORGANISM: Artificial Sequence
<220> FEATURE:
<223> OTHER INFORMATION: Primer

<400> SEQUENCE: 11
taggacgata cgagtgtgta ctcgtggtac acacctacac tactcg            46

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12
cgagtagtgt aggtgtgtac caccatacgg aattcgctca ac                42

<210> SEQ ID NO 13
<211> LENGTH: 44
<212> TYPE: DNA
<213> ORGANISM: Artificial Sequence
<220> FEATURE:
<223> OTHER INFORMATION: Primer

<400> SEQUENCE: 13
ctgtcaaggt agactagcat gctcccatac ggaattcgct caac              44

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
taggacgata cgagtgtgta ctcg                                    24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ctgtcaaggt agactagcat gctc                                    24

<210> SEQ ID NO 16
<211> LENGTH: 56
<212> TYPE: DNA
<213> ORGANISM: Artificial Sequence
<220> FEATURE:
<223> OTHER INFORMATION: Primer

<400> SEQUENCE: 16
ctcggcattc ctgctgaacc gctcttccga tctgctcaac tgacgagcag tcaggt  56

<210> SEQ ID NO 17

```
<211> LENGTH: 39
<212> TYPE: DNA
<213> ORGANISM: Artificial Sequence
<220> FEATURE:
<223> OTHER INFORMATION: Primer

<400> SEQUENCE: 17
acactctttc cctacacgac gctcttccga tcttgacct                              39

<210> SEQ ID NO 18
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 18
aaacggatag actcctcgac                                                   20

<210> SEQ ID NO 19
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 19
aaagggatag actcctcgac                                                   20

<210> SEQ ID NO 20
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 20
aaatggatag actcctcgac                                                   20

<210> SEQ ID NO 21
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 21
aacaggatag actcctcgac                                                   20

<210> SEQ ID NO 22
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 22
aaccggatag actcctcgac                                                   20

<210> SEQ ID NO 23
<211> LENGTH: 20
<212> TYPE: DNA
```

```
<213> ORGANISM: Artificial Sequence
<220> FEATURE:
<223> OTHER INFORMATION: Sequence used in the synthesis of sub-barcode
      molecule library

<400> SEQUENCE: 23
aacgggatag actcctcgac                                                    20

<210> SEQ ID NO 24
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 24
aactggatag actcctcgac                                                    20

<210> SEQ ID NO 25
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 25
aagaggatag actcctcgac                                                    20

<210> SEQ ID NO 26
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 26
aagcggatag actcctcgac                                                    20

<210> SEQ ID NO 27
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 27
aaggggatag actcctcgac                                                    20

<210> SEQ ID NO 28
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 28
aagtggatag actcctcgac                                                    20

<210> SEQ ID NO 29
<211> LENGTH: 20
<212> TYPE: DNA
<213> ORGANISM: Artificial Sequence
```

```
<220> FEATURE:
<223> OTHER INFORMATION: Sequence used in the synthesis of sub-barcode
      molecule library

<400> SEQUENCE: 29
aataggatag actcctcgac                                                    20

<210> SEQ ID NO 30
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 30
aatcggatag actcctcgac                                                    20

<210> SEQ ID NO 31
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 31
aatgggatag actcctcgac                                                    20

<210> SEQ ID NO 32
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 32
aattggatag actcctcgac                                                    20

<210> SEQ ID NO 33
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 33
acaaggatag actcctcgac                                                    20

<210> SEQ ID NO 34
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 34
acacggatag actcctcgac                                                    20

<210> SEQ ID NO 35
<211> LENGTH: 20
<212> TYPE: DNA
<213> ORGANISM: Artificial Sequence
<220> FEATURE:
```

```
<223> OTHER INFORMATION: Sequence used in the synthesis of sub-barcode
      molecule library

<400> SEQUENCE: 35
acagggatag actcctcgac                                               20

<210> SEQ ID NO 36
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 36
acatggatag actcctcgac                                               20

<210> SEQ ID NO 37
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 37
accaggatag actcctcgac                                               20

<210> SEQ ID NO 38
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 38
acccggatag actcctcgac                                               20

<210> SEQ ID NO 39
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 39
accgggatag actcctcgac                                               20

<210> SEQ ID NO 40
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 40
acctggatag actcctcgac                                               20

<210> SEQ ID NO 41
<211> LENGTH: 20
<212> TYPE: DNA
<213> ORGANISM: Artificial Sequence
<220> FEATURE:
<223> OTHER INFORMATION: Sequence used in the synthesis of sub-barcode
``` molecule library

<400> SEQUENCE: 41
acgaggatag actcctcgac                                                                       20

<210> SEQ ID NO 42
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 42
acgcggatag actcctcgac                                                                       20

<210> SEQ ID NO 43
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 43
acggggatag actcctcgac                                                                       20

<210> SEQ ID NO 44
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 44
acgtggatag actcctcgac                                                                       20

<210> SEQ ID NO 45
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 45
actaggatag actcctcgac                                                                       20

<210> SEQ ID NO 46
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 46
actcggatag actcctcgac                                                                       20

<210> SEQ ID NO 47
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 47
actgggatag actcctcgac                                              20

<210> SEQ ID NO 48
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 48
acttggatag actcctcgac                                              20

<210> SEQ ID NO 49
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 49
agaaggatag actcctcgac                                              20

<210> SEQ ID NO 50
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 50
agacggatag actcctcgac                                              20

<210> SEQ ID NO 51
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 51
agagggatag actcctcgac                                              20

<210> SEQ ID NO 52
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 52
agatggatag actcctcgac                                              20

<210> SEQ ID NO 53
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 53
agcaggatag actcctcgac                                                    20

<210> SEQ ID NO 54
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 54
agccggatag actcctcgac                                                    20

<210> SEQ ID NO 55
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 55
agcgggatag actcctcgac                                                    20

<210> SEQ ID NO 56
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 56
agctggatag actcctcgac                                                    20

<210> SEQ ID NO 57
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 57
aggaggatag actcctcgac                                                    20

<210> SEQ ID NO 58
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 58
aggcggatag actcctcgac                                                    20

<210> SEQ ID NO 59
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 59 aggggggatag actcctcgac        20

<210> SEQ ID NO 60
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 60
aggtggatag actcctcgac        20

<210> SEQ ID NO 61
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 61
agtaggatag actcctcgac        20

<210> SEQ ID NO 62
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 62
agtcggatag actcctcgac        20

<210> SEQ ID NO 63
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 63
agtgggatag actcctcgac        20

<210> SEQ ID NO 64
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 64
agttggatag actcctcgac        20

<210> SEQ ID NO 65
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 65
ataaggatag actcctcgac                                              20

<210> SEQ ID NO 66
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 66
atacggatag actcctcgac                                              20

<210> SEQ ID NO 67
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 67
atagggatag actcctcgac                                              20

<210> SEQ ID NO 68
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 68
atatggatag actcctcgac                                              20

<210> SEQ ID NO 69
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 69
atcaggatag actcctcgac                                              20

<210> SEQ ID NO 70
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 70
atccggatag actcctcgac                                              20

<210> SEQ ID NO 71
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 71
atcgggatag actcctcgac                                              20

<210> SEQ ID NO 72
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 72
atctggatag actcctcgac                                                 20

<210> SEQ ID NO 73
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 73
atgaggatag actcctcgac                                                 20

<210> SEQ ID NO 74
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 74
atgcggatag actcctcgac                                                 20

<210> SEQ ID NO 75
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 75
atggggatag actcctcgac                                                 20

<210> SEQ ID NO 76
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 76
atgtggatag actcctcgac                                                 20

<210> SEQ ID NO 77
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 77
attaggatag actcctcgac                                                 20

```
<210> SEQ ID NO 78
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 78
attcggatag actcctcgac                                            20

<210> SEQ ID NO 79
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 79
attgggatag actcctcgac                                            20

<210> SEQ ID NO 80
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 80
atttggatag actcctcgac                                            20

<210> SEQ ID NO 81
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 81
caaaggatag actcctcgac                                            20

<210> SEQ ID NO 82
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 82
caacggatag actcctcgac                                            20

<210> SEQ ID NO 83
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 83
caagggatag actcctcgac                                            20
```

```
<210> SEQ ID NO 84
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 84
caatggatag actcctcgac                                                   20

<210> SEQ ID NO 85
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 85
cacaggatag actcctcgac                                                   20

<210> SEQ ID NO 86
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 86
caccggatag actcctcgac                                                   20

<210> SEQ ID NO 87
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 87
cacgggatag actcctcgac                                                   20

<210> SEQ ID NO 88
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 88
cactggatag actcctcgac                                                   20

<210> SEQ ID NO 89
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 89
cagaggatag actcctcgac                                                   20

<210> SEQ ID NO 90
```

```
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 90
cagcggatag actcctcgac                                              20

<210> SEQ ID NO 91
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 91 cagggatag actcctcgac                                               20

<210> SEQ ID NO 92
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 92
cagtggatag actcctcgac                                              20

<210> SEQ ID NO 93
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 93
cataggatag actcctcgac                                              20

<210> SEQ ID NO 94
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 94
catcggatag actcctcgac                                              20

<210> SEQ ID NO 95
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 95
catgggatag actcctcgac                                              20

<210> SEQ ID NO 96
<211> LENGTH: 20
```

```
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 96
cattggatag actcctcgac                                            20

<210> SEQ ID NO 97
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 97
ccaaggatag actcctcgac                                            20

<210> SEQ ID NO 98
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 98
ccacggatag actcctcgac                                            20

<210> SEQ ID NO 99
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 99
ccagggatag actcctcgac                                            20

<210> SEQ ID NO 100
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 100
ccatggatag actcctcgac                                            20

<210> SEQ ID NO 101
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 101
cccaggatag actcctcgac                                            20

<210> SEQ ID NO 102
<211> LENGTH: 20
<212> TYPE: DNA
```

<213> ORGANISM: Artificial Sequence
<220> FEATURE:
<223> OTHER INFORMATION: Sequence used in the synthesis of sub-barcode
      molecule library

<400> SEQUENCE: 102
cccgggatag actcctcgac                                              20

<210> SEQ ID NO 103
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 103
ccctggatag actcctcgac                                              20

<210> SEQ ID NO 104
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 104
ccgaggatag actcctcgac                                              20

<210> SEQ ID NO 105
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 105
ccgcggatag actcctcgac                                              20

<210> SEQ ID NO 106
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 106
ccggggatag actcctcgac                                              20

<210> SEQ ID NO 107
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 107
ccgtggatag actcctcgac                                              20

<210> SEQ ID NO 108
<211> LENGTH: 20
<212> TYPE: DNA
<213> ORGANISM: Artificial Sequence

```
<220> FEATURE:
<223> OTHER INFORMATION: Sequence used in the synthesis of sub-barcode
      molecule library

<400> SEQUENCE: 108
cctaggatag actcctcgac                                                    20

<210> SEQ ID NO 109
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 109
cctcggatag actcctcgac                                                    20

<210> SEQ ID NO 110
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 110
cctgggatag actcctcgac                                                    20

<210> SEQ ID NO 111
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 111
ccttggatag actcctcgac                                                    20

<210> SEQ ID NO 112
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 112
cgaaggatag actcctcgac                                                    20

<210> SEQ ID NO 113
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 113
cgacggatag actcctcgac                                                    20

<210> SEQ ID NO 114
<211> LENGTH: 20
<212> TYPE: DNA
<213> ORGANISM: Artificial Sequence
<220> FEATURE:
```

<223> OTHER INFORMATION: Sequence used in the synthesis of sub-barcode
      molecule library

<400> SEQUENCE: 114
cgagggatag actcctcgac                                                   20

<210> SEQ ID NO 115
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 115
cgatggatag actcctcgac                                                   20

<210> SEQ ID NO 116
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 116
cgcaggatag actcctcgac                                                   20

<210> SEQ ID NO 117
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 117
cgccggatag actcctcgac                                                   20

<210> SEQ ID NO 118
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 118
cgcgggatag actcctcgac                                                   20

<210> SEQ ID NO 119
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 119
cgctggatag actcctcgac                                                   20

<210> SEQ ID NO 120
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 120
cggaggatag actcctcgac                                              20

<210> SEQ ID NO 121
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 121
cggcggatag actcctcgac                                              20

<210> SEQ ID NO 122
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 122
cgggggatag actcctcgac                                              20

<210> SEQ ID NO 123
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 123
cggtggatag actcctcgac                                              20

<210> SEQ ID NO 124
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 124
cgtaggatag actcctcgac                                              20

<210> SEQ ID NO 125
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 125
cgtcggatag actcctcgac                                              20

<210> SEQ ID NO 126
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 126
cgtgggatag actcctcgac                                          20

<210> SEQ ID NO 127
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 127
cgttggatag actcctcgac                                          20

<210> SEQ ID NO 128
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 128
ctaaggatag actcctcgac                                          20

<210> SEQ ID NO 129
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 129
ctacggatag actcctcgac                                          20

<210> SEQ ID NO 130
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 130
ctagggatag actcctcgac                                          20

<210> SEQ ID NO 131
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 131
ctatggatag actcctcgac                                          20

<210> SEQ ID NO 132
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

```
<400> SEQUENCE: 132
ctcaggatag actcctcgac                                              20

<210> SEQ ID NO 133
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 133
ctccggatag actcctcgac                                              20

<210> SEQ ID NO 134
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 134
ctcgggatag actcctcgac                                              20

<210> SEQ ID NO 135
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 135
ctctggatag actcctcgac                                              20

<210> SEQ ID NO 136
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 136
ctgaggatag actcctcgac                                              20

<210> SEQ ID NO 137
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 137
ctgcggatag actcctcgac                                              20

<210> SEQ ID NO 138
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 138
```
ctggggatag actcctcgac                                              20

<210> SEQ ID NO 139
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 139
ctgtggatag actcctcgac                                              20

<210> SEQ ID NO 140
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 140
cttaggatag actcctcgac                                              20

<210> SEQ ID NO 141
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 141
cttcggatag actcctcgac                                              20

<210> SEQ ID NO 142
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 142
cttgggatag actcctcgac                                              20

<210> SEQ ID NO 143
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 143
ctttggatag actcctcgac                                              20

<210> SEQ ID NO 144
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 144

-continued gaaaggatag actcctcgac					20

<210> SEQ ID NO 145
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 145
gaacggatag actcctcgac					20

<210> SEQ ID NO 146
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 146
gaagggatag actcctcgac					20

<210> SEQ ID NO 147
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 147
gaatggatag actcctcgac					20

<210> SEQ ID NO 148
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 148
gacaggatag actcctcgac					20

<210> SEQ ID NO 149
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 149
gaccggatag actcctcgac					20

<210> SEQ ID NO 150
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 150
gacgggatag actcctcgac					20

<210> SEQ ID NO 151
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 151
gactggatag actcctcgac                                              20

<210> SEQ ID NO 152
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 152
gagaggatag actcctcgac                                              20

<210> SEQ ID NO 153
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 153
gagcggatag actcctcgac                                              20

<210> SEQ ID NO 154
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 154
gaggggatag actcctcgac                                              20

<210> SEQ ID NO 155
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 155
gagtggatag actcctcgac                                              20

<210> SEQ ID NO 156
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 156
gataggatag actcctcgac                                              20

```
<210> SEQ ID NO 157
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 157
gatcggatag actcctcgac                                                    20

<210> SEQ ID NO 158
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 158
gatgggatag actcctcgac                                                    20

<210> SEQ ID NO 159
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 159
gattggatag actcctcgac                                                    20

<210> SEQ ID NO 160
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 160
gcaaggatag actcctcgac                                                    20

<210> SEQ ID NO 161
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 161
gcacggatag actcctcgac                                                    20

<210> SEQ ID NO 162
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 162
gcagggatag actcctcgac                                                    20
```

<210> SEQ ID NO 163
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 163
gcatggatag actcctcgac                                                     20

<210> SEQ ID NO 164
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 164
gccaggatag actcctcgac                                                     20

<210> SEQ ID NO 165
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 165
gcccggatag actcctcgac                                                     20

<210> SEQ ID NO 166
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 166
gccgggatag actcctcgac                                                     20

<210> SEQ ID NO 167
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 167
gcctggatag actcctcgac                                                     20

<210> SEQ ID NO 168
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 168
gcgaggatag actcctcgac                                                     20

<210> SEQ ID NO 169

```
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 169
gcgcggatag actcctcgac                                              20

<210> SEQ ID NO 170
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 170
gcggggatag actcctcgac                                              20

<210> SEQ ID NO 171
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 171
gcgtggatag actcctcgac                                              20

<210> SEQ ID NO 172
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 172
gctaggatag actcctcgac                                              20

<210> SEQ ID NO 173
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 173
gctcggatag actcctcgac                                              20

<210> SEQ ID NO 174
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 174
gctgggatag actcctcgac                                              20

<210> SEQ ID NO 175
<211> LENGTH: 20
```

```
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 175
gcttggatag actcctcgac                                              20

<210> SEQ ID NO 176
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 176
ggaaggatag actcctcgac                                              20

<210> SEQ ID NO 177
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 177
ggacggatag actcctcgac                                              20

<210> SEQ ID NO 178
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 178
ggagggatag actcctcgac                                              20

<210> SEQ ID NO 179
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 179
ggatggatag actcctcgac                                              20

<210> SEQ ID NO 180
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 180
ggcaggatag actcctcgac                                              20

<210> SEQ ID NO 181
<211> LENGTH: 20
<212> TYPE: DNA
```

<213> ORGANISM: Artificial Sequence
<220> FEATURE:
<223> OTHER INFORMATION: Sequence used in the synthesis of sub-barcode
      molecule library

<400> SEQUENCE: 181
ggccggatag actcctcgac                                              20

<210> SEQ ID NO 182
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 182
ggcgggatag actcctcgac                                              20

<210> SEQ ID NO 183
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 183
ggctggatag actcctcgac                                              20

<210> SEQ ID NO 184
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 184
gggaggatag actcctcgac                                              20

<210> SEQ ID NO 185
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 185
gggcggatag actcctcgac                                              20

<210> SEQ ID NO 186
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 186
gggtggatag actcctcgac                                              20

<210> SEQ ID NO 187
<211> LENGTH: 20
<212> TYPE: DNA
<213> ORGANISM: Artificial Sequence

```
<220> FEATURE:
<223> OTHER INFORMATION: Sequence used in the synthesis of sub-barcode
      molecule library

<400> SEQUENCE: 187
ggtaggatag actcctcgac                                                   20

<210> SEQ ID NO 188
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 188
ggtcggatag actcctcgac                                                   20

<210> SEQ ID NO 189
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 189
ggtgggatag actcctcgac                                                   20

<210> SEQ ID NO 190
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 190
ggttggatag actcctcgac                                                   20

<210> SEQ ID NO 191
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 191
gtaaggatag actcctcgac                                                   20

<210> SEQ ID NO 192
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 192
gtacggatag actcctcgac                                                   20

<210> SEQ ID NO 193
<211> LENGTH: 20
<212> TYPE: DNA
<213> ORGANISM: Artificial Sequence
<220> FEATURE:
```

-continued

<223> OTHER INFORMATION: Sequence used in the synthesis of sub-barcode
      molecule library

<400> SEQUENCE: 193
gtagggatag actcctcgac                                              20

<210> SEQ ID NO 194
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 194
gtatggatag actcctcgac                                              20

<210> SEQ ID NO 195
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 195
gtcaggatag actcctcgac                                              20

<210> SEQ ID NO 196
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 196
gtccggatag actcctcgac                                              20

<210> SEQ ID NO 197
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 197
gtcgggatag actcctcgac                                              20

<210> SEQ ID NO 198
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 198
gtctggatag actcctcgac                                              20

<210> SEQ ID NO 199
<211> LENGTH: 20
<212> TYPE: DNA
<213> ORGANISM: Artificial Sequence
<220> FEATURE:
<223> OTHER INFORMATION: Sequence used in the synthesis of sub-barcode -continued molecule library

<400> SEQUENCE: 199
gtgaggatag actcctcgac                                              20

<210> SEQ ID NO 200
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 200
gtgcggatag actcctcgac                                              20

<210> SEQ ID NO 201
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 201
gtggggatag actcctcgac                                              20

<210> SEQ ID NO 202
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 202
gtgtggatag actcctcgac                                              20

<210> SEQ ID NO 203
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 203
gttaggatag actcctcgac                                              20

<210> SEQ ID NO 204
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 204
gttcggatag actcctcgac                                              20

<210> SEQ ID NO 205
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

```
<400> SEQUENCE: 205
gttgggatag actcctcgac                                              20

<210> SEQ ID NO 206
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 206
gtttggatag actcctcgac                                              20

<210> SEQ ID NO 207
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 207
taaaggatag actcctcgac                                              20

<210> SEQ ID NO 208
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 208
taacggatag actcctcgac                                              20

<210> SEQ ID NO 209
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 209
taagggatag actcctcgac                                              20

<210> SEQ ID NO 210
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 210
taatggatag actcctcgac                                              20

<210> SEQ ID NO 211
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library
```

```
<400> SEQUENCE: 211
tacaggatag actcctcgac                                                    20

<210> SEQ ID NO 212
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 212
taccggatag actcctcgac                                                    20

<210> SEQ ID NO 213
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 213
tacgggatag actcctcgac                                                    20

<210> SEQ ID NO 214
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 214
tactggatag actcctcgac                                                    20

<210> SEQ ID NO 215
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 215
tagaggatag actcctcgac                                                    20

<210> SEQ ID NO 216
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 216
tagcggatag actcctcgac                                                    20

<210> SEQ ID NO 217
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 217
``` tagggggatag actcctcgac                                                    20

<210> SEQ ID NO 218
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 218
tagtggatag actcctcgac                                                     20

<210> SEQ ID NO 219
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 219
tataggatag actcctcgac                                                     20

<210> SEQ ID NO 220
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 220
tatcggatag actcctcgac                                                     20

<210> SEQ ID NO 221
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 221
tatgggatag actcctcgac                                                     20

<210> SEQ ID NO 222
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 222
tattggatag actcctcgac                                                     20

<210> SEQ ID NO 223
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 223
tcaaggatag actcctcgac        20

<210> SEQ ID NO 224
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 224
tcacggatag actcctcgac        20

<210> SEQ ID NO 225
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 225
tcagggatag actcctcgac        20

<210> SEQ ID NO 226
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 226
tcatggatag actcctcgac        20

<210> SEQ ID NO 227
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 227
tccaggatag actcctcgac        20

<210> SEQ ID NO 228
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 228
tcccggatag actcctcgac        20

<210> SEQ ID NO 229
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 229
tccgggatag actcctcgac        20

<210> SEQ ID NO 230
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 230
tcctggatag actcctcgac                                                      20

<210> SEQ ID NO 231
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 231
tcgaggatag actcctcgac                                                      20

<210> SEQ ID NO 232
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 232
tcgcggatag actcctcgac                                                      20

<210> SEQ ID NO 233
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 233
tcggggatag actcctcgac                                                      20

<210> SEQ ID NO 234
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 234
tcgtggatag actcctcgac                                                      20

<210> SEQ ID NO 235
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 235
tctaggatag actcctcgac                                                      20

<210> SEQ ID NO 236
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 236
tctcggatag actcctcgac    20

<210> SEQ ID NO 237
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 237
tctgggatag actcctcgac    20

<210> SEQ ID NO 238
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 238
tcttggatag actcctcgac    20

<210> SEQ ID NO 239
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 239
tgaaggatag actcctcgac    20

<210> SEQ ID NO 240
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 240
tgacggatag actcctcgac    20

<210> SEQ ID NO 241
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 241
tgagggatag actcctcgac    20

```
<210> SEQ ID NO 242
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 242
tgatggatag actcctcgac                                                    20

<210> SEQ ID NO 243
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 243
tgcaggatag actcctcgac                                                    20

<210> SEQ ID NO 244
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 244
tgccggatag actcctcgac                                                    20

<210> SEQ ID NO 245
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 245
tgcgggatag actcctcgac                                                    20

<210> SEQ ID NO 246
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 246
tgctggatag actcctcgac                                                    20

<210> SEQ ID NO 247
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 247
tggaggatag actcctcgac                                                    20

<210> SEQ ID NO 248
```

```
<210> SEQ ID NO 248
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 248
tggcggatag actcctcgac                                                 20

<210> SEQ ID NO 249
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 249
tgggggatag actcctcgac                                                 20

<210> SEQ ID NO 250
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 250
tggtggatag actcctcgac                                                 20

<210> SEQ ID NO 251
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 251
tgtaggatag actcctcgac                                                 20

<210> SEQ ID NO 252
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 252
tgtcggatag actcctcgac                                                 20

<210> SEQ ID NO 253
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 253
tgtgggatag actcctcgac                                                 20

<210> SEQ ID NO 254
<211> LENGTH: 20
```

```
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 254
tgttggatag actcctcgac                                               20

<210> SEQ ID NO 255
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 255
ttaaggatag actcctcgac                                               20

<210> SEQ ID NO 256
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 256
ttacggatag actcctcgac                                               20

<210> SEQ ID NO 257
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 257
ttagggatag actcctcgac                                               20

<210> SEQ ID NO 258
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 258
ttatggatag actcctcgac                                               20

<210> SEQ ID NO 259
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 259
ttcaggatag actcctcgac                                               20

<210> SEQ ID NO 260
<211> LENGTH: 20
<212> TYPE: DNA
```

```
<213> ORGANISM: Artificial Sequence
<220> FEATURE:
<223> OTHER INFORMATION: Sequence used in the synthesis of sub-barcode
      molecule library

<400> SEQUENCE: 260
ttccggatag actcctcgac                                                  20

<210> SEQ ID NO 261
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 261
ttcgggatag actcctcgac                                                  20

<210> SEQ ID NO 262
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 262
ttctggatag actcctcgac                                                  20

<210> SEQ ID NO 263
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 263
ttgaggatag actcctcgac                                                  20

<210> SEQ ID NO 264
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 264
ttgcggatag actcctcgac                                                  20

<210> SEQ ID NO 265
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 265
ttggggatag actcctcgac                                                  20

<210> SEQ ID NO 266
<211> LENGTH: 20
<212> TYPE: DNA
<213> ORGANISM: Artificial Sequence
```

<220> FEATURE:
<223> OTHER INFORMATION: Sequence used in the synthesis of sub-barcode
      molecule library

<400> SEQUENCE: 266
ttgtggatag actcctcgac                                                    20

<210> SEQ ID NO 267
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 267
tttaggatag actcctcgac                                                    20

<210> SEQ ID NO 268
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 268
tttcggatag actcctcgac                                                    20

<210> SEQ ID NO 269
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 269
tttgggatag actcctcgac                                                    20

<210> SEQ ID NO 270
<211> LENGTH: 47
<212> TYPE: DNA
<213> ORGANISM: Artificial Sequence
<220> FEATURE:
<223> OTHER INFORMATION: Primer

<400> SEQUENCE: 270
taatacgact cactataggg agataggacg atacgagtgt gtactcg                      47

<210> SEQ ID NO 271
<211> LENGTH: 31
<212> TYPE: DNA
<213> ORGANISM: Artificial Sequence
<220> FEATURE:
<223> OTHER INFORMATION: Primer

<400> SEQUENCE: 271
ctgtcaaggt agactagcat gctcccatac g                                       31

<210> SEQ ID NO 272
<211> LENGTH: 24
<212> TYPE: DNA
<213> ORGANISM: Artificial Sequence
<220> FEATURE:
<223> OTHER INFORMATION: Primer

<400> SEQUENCE: 272
ctgtcaaggt agactagcat gctc                                          24

<210> SEQ ID NO 273
<211> LENGTH: 60
<212> TYPE: DNA
<213> ORGANISM: Artificial Sequence
<220> FEATURE:
<223> OTHER INFORMATION: Adaptor oligonucleotide

<400> SEQUENCE: 273
cctgactgct cgtcagttga ttaagtactc tgtgagatga tgatcagtag agcgagtcgt    60

<210> SEQ ID NO 274
<211> LENGTH: 50
<212> TYPE: DNA
<213> ORGANISM: Artificial Sequence
<220> FEATURE:
<223> OTHER INFORMATION: Primer

<400> SEQUENCE: 274
caccgagatc tacactcttt ccctacacga cgctcttccg atcttgacct               50

<210> SEQ ID NO 275
<211> LENGTH: 59
<212> TYPE: DNA
<213> ORGANISM: Artificial Sequence
<220> FEATURE:
<223> OTHER INFORMATION: Synthetic template
<220> FEATURE:
<221> NAME/KEY: misc_feature
<222> LOCATION: (22)..(39)
<223> OTHER INFORMATION: n is a, c, g, or t

<400> SEQUENCE: 275
atgatcagta gagcgagtcg tnnnnnnnnn nnnnnnnnnt gctacgactt ccgagtcca     59

<210> SEQ ID NO 276
<211> LENGTH: 27
<212> TYPE: DNA
<213> ORGANISM: Artificial Sequence
<220> FEATURE:
<223> OTHER INFORMATION: Primer

<400> SEQUENCE: 276
gctctactga tcattggact cggaagt                                       27

<210> SEQ ID NO 277
<211> LENGTH: 28
<212> TYPE: DNA
<213> ORGANISM: Artificial Sequence
<220> FEATURE:
<223> OTHER INFORMATION: Primer

<400> SEQUENCE: 277
tccgatcttg gactcggaag tcgtagca                                      28

<210> SEQ ID NO 278
<211> LENGTH: 39
<212> TYPE: DNA
<213> ORGANISM: Artificial Sequence
<220> FEATURE:
<223> OTHER INFORMATION: Primer

<400> SEQUENCE: 278 acactcttc cctacacgac gctcttccga tcttgacct                           39

<210> SEQ ID NO 279
<211> LENGTH: 59
<212> TYPE: DNA
<213> ORGANISM: Artificial Sequence
<220> FEATURE:
<223> OTHER INFORMATION: BRCA1 adaptor oligonucleotide

<400> SEQUENCE: 279
cctgactgct cgtcagttga ttaagtactc tgtgagatgc ttggcccctc ttcggtaac    59

<210> SEQ ID NO 280
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 280
cctgactgct cgtcagttga ttaagtactc tgtgagatgc tgggagctca aaagatggct   60

<210> SEQ ID NO 281
<211> LENGTH: 58
<212> TYPE: DNA
<213> ORGANISM: Artificial Sequence
<220> FEATURE:
<223> OTHER INFORMATION: BRCA1 adaptor oligonucleotide

<400> SEQUENCE: 281
cctgactgct cgtcagttga ttaagtactc tgtgagatgc agctgggctc aaaggacc     58

<210> SEQ ID NO 282
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 282
cctgactgct cgtcagttga ttaagtactc tgtgagatgc agacaaattc cccagcaggt   60

<210> SEQ ID NO 283
<211> LENGTH: 58
<212> TYPE: DNA
<213> ORGANISM: Artificial Sequence
<220> FEATURE:
<223> OTHER INFORMATION: BRCA1 adaptor oligonucleotide

<400> SEQUENCE: 283
cctgactgct cgtcagttga ttaagtactc tgtgagatgc atggtgtgaa cccgggag     58

<210> SEQ ID NO 284
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 284
cctgactgct cgtcagttga ttaagtactc tgtgagatgc ccaaatccca agtcgtgtgt   60

<210> SEQ ID NO 285
<211> LENGTH: 60
<212> TYPE: DNA
<213> ORGANISM: Artificial Sequence
<220> FEATURE:

<223> OTHER INFORMATION: BRCA1 adaptor oligonucleotide

<400> SEQUENCE: 285
cctgactgct cgtcagttga ttaagtactc tgtgagatgc tcatccctgg ttccttgagg     60

<210> SEQ ID NO 286
<211> LENGTH: 60
<212> TYPE: DNA
<213> ORGANISM: Artificial Sequence
<220> FEATURE:
<223> OTHER INFORMATION: HLA-A adaptor oligonucleotide

<400> SEQUENCE: 286
cctgactgct cgtcagttga ttaagtactc tgtgaaaacg gcctctgtgg ggagaagcaa     60

<210> SEQ ID NO 287
<211> LENGTH: 59
<212> TYPE: DNA
<213> ORGANISM: Artificial Sequence
<220> FEATURE:
<223> OTHER INFORMATION: HLA-A adaptor oligonucleotide

<400> SEQUENCE: 287
cctgactgct cgtcagttga ttaagtactc tgtgagatgc actgggctga ccgtggggt     59

<210> SEQ ID NO 288
<211> LENGTH: 60
<212> TYPE: DNA
<213> ORGANISM: Artificial Sequence
<220> FEATURE:
<223> OTHER INFORMATION: HLA-A adaptor oligonucleotide

<400> SEQUENCE: 288
cctgactgct cgtcagttga ttaagtactc tgcctgaatg wtctgactct tcccgtmaga     60

<210> SEQ ID NO 289
<211> LENGTH: 60
<212> TYPE: DNA
<213> ORGANISM: Artificial Sequence
<220> FEATURE:
<223> OTHER INFORMATION: DQB1 adaptor oligonucleotide

<400> SEQUENCE: 289
cctgactgct cgtcagttga ttaagtactc tgggatcccc gcagaggatt tcgtgtacca     60

<210> SEQ ID NO 290
<211> LENGTH: 60
<212> TYPE: DNA
<213> ORGANISM: Artificial Sequence
<220> FEATURE:
<223> OTHER INFORMATION: DQB1 adaptor oligonucleotide

<400> SEQUENCE: 290
cctgactgct cgtcagttga ttaagtactc tgtgagatgg agcccacagt gaccatctcc     60

<210> SEQ ID NO 291
<211> LENGTH: 60
<212> TYPE: DNA
<213> ORGANISM: Artificial Sequence
<220> FEATURE:
<223> OTHER INFORMATION: BRCA1 reverse primer

<400> SEQUENCE: 291
cggtctcggc attcctgctg aaccgctctt ccgatctgtt ctgagacacc tgatgacctg     60

```
<210> SEQ ID NO 292
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 292
cggtctcggc attcctgctg aaccgctctt ccgatcttga acccaggagt ttgaggc        57

<210> SEQ ID NO 293
<211> LENGTH: 60
<212> TYPE: DNA
<213> ORGANISM: Artificial Sequence
<220> FEATURE:
<223> OTHER INFORMATION: BRCA1 reverse primer

<400> SEQUENCE: 293
cggtctcggc attcctgctg aaccgctctt ccgatcttgg agctttatct gctctgtgat     60

<210> SEQ ID NO 294
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 294
cggtctcggc attcctgctg aaccgctctt ccgatctttc actgtgatgg ccaggat        57

<210> SEQ ID NO 295
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 295
cggtctcggc attcctgctg aaccgctctt ccgatcttga cccaagcaag cctaaag        57

<210> SEQ ID NO 296
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 296
cggtctcggc attcctgctg aaccgctctt ccgatcttgc cacagtagat gctcagt        57

<210> SEQ ID NO 297
<211> LENGTH: 58
<212> TYPE: DNA
<213> ORGANISM: Artificial Sequence
<220> FEATURE:
<223> OTHER INFORMATION: BRCA1 reverse primer

<400> SEQUENCE: 297
cggtctcggc attcctgctg aaccgctctt ccgatctccc agcaaccatt tcatttca       58

<210> SEQ ID NO 298
<211> LENGTH: 60
<212> TYPE: DNA
<213> ORGANISM: Artificial Sequence
<220> FEATURE:
<223> OTHER INFORMATION: HLA-A reverse primer
```

```
<400> SEQUENCE: 298
cggtctcggc attcctgctg aaccgctctt ccgatcttgg atctcggacc cggagactgt        60

<210> SEQ ID NO 299
<211> LENGTH: 58
<212> TYPE: DNA
<213> ORGANISM: Artificial Sequence
<220> FEATURE:
<223> OTHER INFORMATION: HLA-A reverse primer

<400> SEQUENCE: 299
cggtctcggc attcctgctg aaccgctctt ccgatctccc tggtaccvgt gcgctgca         58

<210> SEQ ID NO 300
<211> LENGTH: 60
<212> TYPE: DNA
<213> ORGANISM: Artificial Sequence
<220> FEATURE:
<223> OTHER INFORMATION: HLA-A reverse primer

<400> SEQUENCE: 300
cggtctcggc attcctgctg aaccgctctt ccgatctgac cctgctaaag gtctccagag        60

<210> SEQ ID NO 301
<211> LENGTH: 57
<212> TYPE: DNA
<213> ORGANISM: Artificial Sequence
<220> FEATURE:
<223> OTHER INFORMATION: HLA-A reverse primer

<400> SEQUENCE: 301
cggtctcggc attcctgctg aaccgctctt ccgatctgac cctgctaaag gtcagag           57

<210> SEQ ID NO 302
<211> LENGTH: 60
<212> TYPE: DNA
<213> ORGANISM: Artificial Sequence
<220> FEATURE:
<223> OTHER INFORMATION: DQB1 reverse primer

<400> SEQUENCE: 302
cggtctcggc attcctgctg aaccgctctt ccgatctagg acgctcacct ctccgctgca        60

<210> SEQ ID NO 303
<211> LENGTH: 57
<212> TYPE: DNA
<213> ORGANISM: Artificial Sequence
<220> FEATURE:
<223> OTHER INFORMATION: DQB1 reverse primer

<400> SEQUENCE: 303
cggtctcggc attcctgctg aaccgctctt ccgatctctg gggtgctcca cgtggca           57
```